United States Patent
Han et al.

(10) Patent No.: US 11,474,100 B2
(45) Date of Patent: Oct. 18, 2022

(54) CHROMOPHORE-LABELED OLIGOSACCHARIDE MARKERS AND METHODS OF USE THEREOF

(71) Applicant: Hong Kong Baptist University, Hong Kong (HK)

(72) Inventors: Quanbin Han, Hong Kong (HK); Lifeng Li, Hong Kong (HK); Tin Long Wong, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 283 days.

(21) Appl. No.: 16/871,188

(22) Filed: May 11, 2020

(65) Prior Publication Data
US 2020/0363404 A1     Nov. 19, 2020

Related U.S. Application Data

(60) Provisional application No. 62/871,205, filed on Jul. 8, 2019, provisional application No. 62/847,912, filed on May 14, 2019.

(51) Int. Cl.
| | | |
|---|---|---|
| *G01N 33/50* | (2006.01) | |
| *G01N 33/58* | (2006.01) | |
| *G01N 1/40* | (2006.01) | |

(52) U.S. Cl.
CPC ....... *G01N 33/5097* (2013.01); *G01N 1/4055* (2013.01); *G01N 33/58* (2013.01); *G01N 2333/415* (2013.01); *G01N 2400/10* (2013.01)

(58) Field of Classification Search
CPC .. G01N 33/5097; G01N 1/4055; G01N 33/58; G01N 2333/415; G01N 2400/10; G01N 33/532; G01N 33/5308
See application file for complete search history.

(56) References Cited

PUBLICATIONS

Nakajima et al., "Time-resolved fluorometric analysis of carbohydrates labeled with amino-aromatic compounds by reductive amination," Analyst, May 27, 2002, Iss. 7, pp. 972-976, DOI: 10.1039/b202950b. (Year: 2002).*
Neville et al., "Hydrophilic interaction liquid chromatography of anthranilic acid-labelled oligosaccharides with a 4-aminobenzoic acid ethyl ester-labelled dextran hydrolysate internal standard," Journal of Chromatography A, Apr. 13, 2012, vol. 1233, pp. 66-70, DOI: 10.1016/j.chroma.2012.02.007. (Year: 2012).*
Li et al., "Carbohydrates analysis in herbal glycomics," TrAC Trends in Analytical Chemistry, 2013, vol. 52, pp. 155-169, DOI: 10.1016/j.trac.2013.05.020. (Year: 2013).*
Lorenz et al., "A new method for the quantification of monosaccharides, uronic acids and oligosaccharides in partially hydrolyzed xylans by HPAEC-UV/VIS," Carbohydrate Polymers, vol. 140, pp. 181-187, DOI: 10.1016/j.carbpol.2015.12.027. (Year: 2016).*

(Continued)

*Primary Examiner* — Jennifer Wecker
*Assistant Examiner* — Michael Paul Shimek
(74) *Attorney, Agent, or Firm* — S&F/WEHRW

(57) ABSTRACT

Provided herein are compositions and methods useful for the analysis and authentication of polysaccharide-rich herbs, such as *Dendrobium officinale*, Radix Astragali, Radix Angelica Sinensis, and related herbal products.

5 Claims, 83 Drawing Sheets

(56) References Cited

PUBLICATIONS

Wong et al., "Oligosaccharide-marker approach for the qualitative and quantitative analysis of specific polysaccharide in herb formula . . . Dendrobium officinale, a case study," Journal of Chromatography A, Dec. 6, 2019, vol. 160, pp. 1-9, DOI: 10.1016/j.chroma.2019.460388. (Year: 2019).*

LGC Standards, "Reference Material Certificate: 4-Aminobenzoic acid-ethyl ester," Jul. 5, 2021, <https://assets.lgcstandards.com/sys-master%2Fpdfs%2Fhaf%2Fh9f%2F10374912540702%2FCOA_DRE-C10171450_ST-WB-CERT-3562656-1-1-1.PDF?_ga=2.94877146.773480620.1649968396-955964665.1649792772>. (Year: 2021).*

Chen et al., "Traditional Uses, Phytochemistry, Pharmacology, and Quality Control of Dendrobium officinale Kimura et. Migo," Frontiers in Pharmacology, Aug. 6, 2021, vol. 12, pp. 18-19, DOI: 10.3389/fphar.2021.726528. (Year: 2021).*

International Search Report and Written Opinion of PCT application No. PCT/CN2020/089893 issued from the International Search Authority dated Aug. 21, 2020.

Li et al.; Carbohydrates analysis in herbal glycomics; Trends in Analytical Chemistry; 2013; vol. 52; pp. 155-169.

Neville et al.; Hydrophilic interaction liquid chromatography of anthranilic acid-labelled oligosaccharides with a 4-aminobenzoic acid ethyl ester-labelled dextran hydrolysate internal standard; Journal of Chromatography A; 2012; vol. 1233; pp. 66-70.

* cited by examiner

Am-1

Am-2

Table 1

| Sample code | Locality | Type | Molecular weight[a] | Sugar content[b] | DOP |
|---|---|---|---|---|---|
| HGR-D1 | Yunna, China | Dry powdered | 750kDa | 72.05% | 261.29 |
| HGR-D2 | Yunna, China | Dry powdered | 770kDa | 72.94% | 459.51 |
| HGR-D3 | Yunna, China | Dry powdered | 790kDa | 72.79% | 220.11 |
| TFC-T1 | Guangdong, China | Fresh pulp | 800kDa | 67.91% | 161.47 |
| TFC-T2 | Guangdong, China | Fresh pulp | 770kDa | 71.10% | 236.61 |
| TFC-B1 | Zhejing, China | Fresh pulp | 770kDa | 75.44% | 120.99 |
| DOP standard | NA | NA | 770kDa | 92.65% | NA |

FIG. 23

Table 2

| Oligosaccharide | Mass | | Error (ppm) | DP | Monosaccharides composition | | Residue linkage Peak area percentage | |
|---|---|---|---|---|---|---|---|---|
| | Observed | Calculated | | | Man | Glu | T-Man$p$ | 1,4-linked-Man$p$ |
| Di-Man-ABEE | 490.1880 | 490.193 | -10.2 | 2 | 96.76 | 3.24 | NA | NA |
| Tri-Man-ABEE | 652.2444 | 652.2458 | -2.15 | 3 | 95.23 | 4.77 | 43.36 | 56.64 |
| Te-Man-ABEE | 814.2974 | 814.2986 | -1.47 | 4 | 96.91 | 3.09 | 29.39 | 70.61 |
| Pen-Man-ABEE | 976.3520 | 976.3515 | 0.51 | 5 | 96.71 | 3.29 | 26.57 | 73.43 |
| Hex-Man-ABEE | 1138.3909 | 1138.4043 | -11.77 | 6 | 96.4 | 3.6 | 20.54 | 79.46 |
| Hept-Man-ABEE | 1300.4585 | 1300.4571 | 1.08 | 7 | 97.15 | 2.85 | 16.91 | 83.09 |
| Oct-Man-ABEE | 1462.5226 | 1462.5099 | 8.68 | 8 | 97.83 | 2.17 | 13.69 | 86.31 |
| Nona-Man-ABEE | 1624.4835 | 1624.4628 | 12.7 | 9 | 96.89 | 3.11 | NA | NA |
| Deca-Man-ABEE | 1787.6407 | 1787.6156 | 14.0 | 10 | 97.60 | 2.40 | NA | NA |

FIG. 24

Table 3

| Saccharide | Chemical shift ($^1$H/$^{13}$C, in ppm) | | | | | | |
|---|---|---|---|---|---|---|---|
| | 1 | 2 | 3 | 4 | 5 | 6 | 7 |
| Man | 5.18/96.88 | 3.94/74.06 | 3.66/75.89 | 3.52/69.45 | 3.58/79.01 | 3.75,3.82/63.82 | |
| Man-ABEE | | | | | | | |
| a (ABEE) | 172.3 | 120.13 | 7.84/134.45 | 6.81/115.41 | 156.16 | 4.32/64.85 | 1.35/16.65 |
| r Man | 3.27,3.67/48.83 | 3.82/73.49 | 3.79/73.72 | 3.92/72.01 | 3.84/72.13 | 3.68,3.89/66.09 | |
| Di-Man-ABEE | | | | | | | |
| a (ABEE) | 172.16 | 120.19 | 7.80/134.27 | 6.76/115.27 | 156.06 | 4.28/64.45 | 1.34/16.36 |
| i Man | 4.77/102.81 | 4.11/71.59 | 3.67/75.82 | 3.50/70.04 | 3.40/78.82 | 3.56,3.89/64.39 | |
| r Man | 3.22,3.66/48.69 | 4.12/73.42 | 3.78/73.89 | 4.11/79.74 | 3.94/73.50 | 3.71,3.86/65.28 | |
| Tri-Man-ABEE | | | | | | | |
| a (ABEE) | 172.2 | 120.26 | 7.83/134.35 | 6.80/115.39 | 156.07 | 4.30/64.48 | 1.35/16.47 |
| i Man | 4.79/102.82 | 4.14/73.05 | 3.65/75.68 | 3.57/69.55 | 3.39/79.30 | 3.55,3.93/63.71 | |
| ii Man | 4.63/103.08 | 4.02/73.36 | 3.61/75.68 | 3.72/80.03 | 3.51/77.60 | 3.74/3.81/63.78 | |
| r Man | 3.22,3.69/48.68 | 4.13/71.46 | 3.78/74.18 | 4.11/80.05 | 3.94/73.48 | 3.68,3.85/65.35 | |

FIG. 25

Table 3 (Continued)

| Saccharide | Chemical shift ($^1$H/$^{13}$C, in ppm) | | | | | | |
|---|---|---|---|---|---|---|---|
| | 1 | 2 | 3 | 4 | 5 | 6 | 7 |
| Man | 5.18/96.88 | 3.94/74.06 | 3.66/75.89 | 3.52/69.45 | 3.58/79.01 | 3.75,3.82/63.82 | |
| Man-ABEE | | | | | | | |
| a (ABEE) | 172.3 | 120.13 | 7.84/134.45 | 6.81/115.41 | 156.16 | 4.32/64.85 | 1.35/16.65 |
| r Man | 3.27,3.67/48.83 | 3.82/73.49 | 3.79/73.72 | 3.92/72.01 | 3.84/72.13 | 3.68,3.89/66.09 | |
| Di-Man-ABEE | | | | | | | |
| a (ABEE) | 172.16 | 120.19 | 7.80/134.27 | 6.76/115.27 | 156.06 | 4.28/64.45 | 1.34/16.36 |
| i Man | 4.77/102.81 | 4.11/71.59 | 3.67/75.82 | 3.50/70.04 | 3.40/78.82 | 3.56,3.89/64.39 | |
| r Man | 3.22,3.66/48.69 | 4.12/73.42 | 3.78/73.89 | 4.11/79.74 | 3.94/73.50 | 3.71,3.86/65.28 | |
| Tri-Man-ABEE | | | | | | | |
| a (ABEE) | 172.2 | 120.26 | 7.83/134.35 | 6.80/115.39 | 156.07 | 4.30/64.48 | 1.35/16.47 |
| i Man | 4.79/102.82 | 4.14/73.05 | 3.65/75.68 | 3.57/69.55 | 3.39/79.30 | 3.55,3.93/63.71 | |
| ii Man | 4.63/103.08 | 4.02/73.36 | 3.61/75.68 | 3.72/80.03 | 3.51/77.60 | 3.74/3.81/63.78 | |
| r Man | 3.22,3.69/48.68 | 4.13/71.46 | 3.78/74.18 | 4.11/80.05 | 3.94/73.48 | 3.68,3.85/65.35 | |

FIG. 25 (Continued)

Table 3 (Continued)

| Saccharide | Chemical shift ($^1$H/$^{13}$C, in ppm) | | | | | | |
|---|---|---|---|---|---|---|---|
| | 1 | 2 | 3 | 4 | 5 | 6 | 7 |
| Te-Man-ABEE | | | | | | | |
| a (ABEE) | 172.18 | 120.23 | 7.83/134.36 | 6.79/115.38 | 156.06 | 4.31/64.51 | 1.35/16.40 |
| i Man | 4.79/102.82 | 4.15/73.02 | 3.65/75.74 | 3.58/69.63 | 3.45/79.26 | 3.52,3.94/63.69 | |
| ii Man | 4.73/103.05 | 4.08/72.86 | 3.81/74.29 | 3.83/79.40 | 3.52/77.71 | 3.75,3.90/63.36 | |
| iii Man | 4.64/103.03 | 4.07/73.21 | 3.78/74.13 | 3.72/79.91 | 3.50/77.75 | 3.81,3.93/63.42 | |
| r Man | 3.22,3.69/48.85 | 4.13/71.53 | 3.78/74.13 | 4.09/79.93 | 3.94/73.43 | 3.69,3.85/65.39 | |
| Pen-Man-ABEE | | | | | | | |
| a (ABEE) | 172.01 | 122.52 | 7.89/134.72 | 6.80/117.19 | 153.98 | 4.31/65.00 | 1.35/16.50 |
| i Man | 4.88/103.11 | 4.13/73.08 | 3.64/76.04 | 3.57/69.93 | 3.44/79.56 | 3.52,3.97/64.06 | |
| ii Man | 4.74/103.34 | 4.06/73.53 | 3.81/74.60 | 3.82/79.67 | 3.64/76.04 | ~3.76/63.92 | |
| iii Man | 4.73/103.40 | 4.08/73.53 | 3.76/74.39 | 3.81/79.71 | 3.52/78.03 | ~3.76/63.92 | |
| iv-Man | 3.65/103.37 | 4.08/73.06 | 3.76/74.47 | 3.71/80.17 | 3.50/78.03 | ~3.76/63.92 | |
| r Man | 3.26,3.72/50.36 | 4.13/71.44 | 3.78/74.44 | 4.07/80.04 | 3.92/73.65 | 3.67,3.83/65.64 | |

FIG. 25 (Continued)

Table 3 (Continued)

| Saccharide | Chemical shift ($^1$H/$^{13}$C, in ppm) | | | | | | |
|---|---|---|---|---|---|---|---|
| | 1 | 2 | 3 | 4 | 5 | 6 | 7 |
| a (ABEE) | 172.21 | 120.27 | 7.85/134.33 | 6.80.115.41 | 156.08 | 4.31/64.63 | 1.34/16.43 |
| i Man | 4.78/102.80 | 4.14/72.74 | 3.65/75.66 | 3.58/69.54 | 3.45/79.21 | 3.52,3.97/63.60 | |
| ii Man | 4.76/102.95 | 4.08/72.95 | 3.79.74.16 | 3.82/79.34 | 3.57/77.78 | ~3.76/63.92 | |
| iii Man | 4.74/103.00 | 4.08/72.95 | 3.79.74.16 | 3.82/79.34 | 3.57/77.78 | ~3.76/63.92 | |
| iv Man | 4.76/102.96 | 4.08/72.95 | 3.79.74.16 | 3.82/79.34 | 3.57/77.78 | ~3.76/63.92 | |
| v Man | 4.65/102.99 | 4.08/72.95 | 3.79.74.16 | 3.72/79.84 | 3.57/77.78 | 3.76/63.92 | |
| r Man | 3.22,3.69/48.59 | 4.13/71.47 | 3.79.74.16 | 4.08/79.91 | 3.94/73.34 | 3.68,3.85/65.27 | |
| Hept-Man-ABEE | | | | | | | |
| a (ABEE) | 172.22 | 120.27 | 7.86/134.35 | 6.82/115.41 | 156.08 | 4.32/64.55 | 1.37/16.36 |
| i Man | 4.78/102.78 | 4.13/72.72 | 3.65/75.88 | 3.58/69.67 | 3.45/79.26 | 3.52,4.02/63.43 | |
| ii Man | 4.76/103.01 | 4.08/73.09 | 3.80/74.34 | 3.83/79.33 | 3.56/77.92 | ~3.75/63.64 | |
| iii Man | 4.76/103.01 | 4.08/73.09 | 3.80/74.34 | 3.83/79.33 | 3.56/77.92 | ~3.75/63.64 | |
| iv Man | 4.76/103.01 | 4.08/73.09 | 3.80/74.34 | 3.83/79.33 | 3.56/77.92 | ~3.75/63.64 | |
| v Man | 4.76/103.01 | 4.08/73.09 | 3.80/74.34 | 3.83/79.33 | 3.56/77.92 | ~3.75/63.64 | |
| vi Man | 4.66/103.05 | 4.08/73.09 | 3.80/74.34 | 3.72/80.05 | 3.56/77.92 | ~3.75/63.64 | |
| r Man | 3.22,3.69/48.91 | 4.13/72.72 | 3.80/74.34 | 4.10/79.88 | 3.94/73.52 | 3.67,3.84/65.32 | |

FIG. 25 (Continued)

Table 3 (Continued)

| Saccharide | Chemical shift ($^1$H/$^{13}$C, in ppm) | | | | | | |
|---|---|---|---|---|---|---|---|
| | 1 | 2 | 3 | 4 | 5 | 6 | 7 |
| a (ABEE) | 172.2 | 120.26 | 7.83/134.35 | 6.80/115.39 | 156.07 | 4.30/64.48 | 1.35/16.47 |
| i Man | 4.79/102.83 | 4.15/72.86 | 3.66/75.76 | 3.59/69.61 | 3.46/79.25 | 3.53,4.06/63.14 | |
| ii Man | 4.75/103.00 | 4.08/73.19 | 3.80/74.28 | 3.83/79.39 | 3.58/77.91 | ~3.77/63.46 | |
| iii Man | 4.75/103.00 | 4.08/73.19 | 3.80/74.28 | 3.83/79.39 | 3.58/77.91 | ~3.77/63.46 | |
| iv Man | 4.75/103.00 | 4.08/73.19 | 3.80/74.28 | 3.83/79.39 | 3.58/77.91 | ~3.77/63.46 | |
| v Man | 4.75/103.00 | 4.08/73.19 | 3.80/74.28 | 3.83/79.39 | 3.58/77.91 | ~3.77/63.46 | |
| vi Man | 4.75/103.00 | 4.08/73.19 | 3.80/74.28 | 3.83/79.39 | 3.58/77.91 | ~3.77/63.46 | |
| vii Man | 4.66/103.03 | 4.08/73.19 | 3.80/74.28 | 3.73/79.84 | 3.58/77.91 | ~3.77/63.46 | |
| r Man | 3.23,3.70/48.83 | 4.15/71.56 | 3.80/74.28 | 4.09/79.95 | 3.94/73.32 | 3.70,3.86/65.34 | |

FIG. 25 (Continued)

Table 4

| Oligosaccharide markers | Linearity | | $R^2$ |
|---|---|---|---|
| | Range (mg/mL) | Equation | |
| Te-Man-ABEE | 0.34-8.01 | y = 1164589x + 194721.9 | 0.997 |
| Pen-Man-ABEE | 0.34-8.01 | y = 629621x + 172565 | 0.997 |

FIG. 26

Table 5

| Analyte | Oligosaccharide markers | Repeatability (RSD, %) | | Spike recovery % (RSD, n=3) | | |
|---|---|---|---|---|---|---|
| | | Intra-day (n=6) | Inter-day (n=3) | Low | Middle | High |
| Dendrobium offcinale water extract | Te-Man-ABEE | 2.31 | 4.49 | 93.30 (4.05) | 117.86 (1.41) | 104.79 (0.74) |
| | Pen-Man-ABEE | 3.04 | 5.50 | 98.19 (0.83) | 118.30 (2.80) | 107.75 (0.87) |
| TVC | Te-Man-ABEE | 4.76 | 6.67 | 102.24 (6.88) | 100.05 (8.09) | 91.41 (7.38) |
| | Pen-Man-ABEE | 3.66 | 5.23 | 103.62 (7.94) | 117.04 (4.40) | 96.47 (5.39) |
| GD | Te-Man-ABEE | 2.11 | 5.30 | 112.91 (5.16) | 99.50 (5.19) | 100.05 (3.79) |
| | Pen-Man-ABEE | 2.14 | 6.91 | 109.20 (2.80) | 97.71 (7.37) | 98.99 (6.01) |

FIG. 27

Table 6

| Type | Conc. of *Dendrobium officinale* water extract (mg/g) | | | | | | Conc. of TVC (mg/g) | | | | Conc. Of GD (mg/g) |
|---|---|---|---|---|---|---|---|---|---|---|---|
| Analyte | HGR-D1 | HGR-D2 | HGR-D3 | TFC-T1 | TFC-T2 | TFC-B1 | 1 | 2 | 3 | 4 | 1 |
| Te-Man-ABEE | 245.12(1.32) | 401.38(0.13) | 208.00(0.28) | 148.48(0.97) | 205.78(0.30) | 110.77(0.20) | 0.20 (6.50) | 0.28 (1.13) | 0.28 (1.10) | 0.28 (2.87) | 32.55 (2.37) |
| Pen-Man-ABEE | 248.98(0.78) | 382.02(0.89) | 198.13(0.61) | 150.14(1.02) | 213.63(1.92) | 122.32(0.99) | 0.19 (5.53) | 0.29 (3.04) | 0.29 (3.02) | 0.28 (3.48) | 31.88 (2.57) |
| RSD between two markers | 1.11 | 3.5 | 3.44 | 0.79 | 2.65 | 7.01 | 3.72 | 1.36 | 0.55 | 1.47 | 1.48 |

FIG. 28

Table 7

| Marker | Sugar Residues | Chemical shift | | | | | | |
|---|---|---|---|---|---|---|---|---|
| | | H-1/C-1 | H-2/C-2 | H-3/C-3 | H-4/C-4 | H-5/C-5 | H-6/C-6 | OCH$_3$ |
| Rm-1 | B:4)-α-D-Glcp-(1-ABEE | 3.41,3.36/ 48.3 | 4.03/ 72.1 | 3.99/ 75.4 | 3.92/ 85.1 | 3.94/ 74 | 3.67,3.78/ 65.1 | / |
| | C: α-D-Glcp-(1 | 5.14/ 103.4 | 3.62/ 74.5 | 3.78/ 75.8 | 3.46/ 72.3 | 3.90/ 75.4 | 3.81,3.88/ 63.3 | / |
| Rm-2 | B:4)-α-D-Glcp-(1-ABEE | 3.36,3.42/ 48.4 | 4.02/ 72 | 3.96/ 75.6 | 3.90/ 85 | 3.99/ 74 | 3.64,3.73/ 65 | / |
| | C: 4)-α-D-Glcp-(1 | 5.13/ 103.2 | 3.59/ 74.7 | 4.01/ 76.3 | 3.67/ 79.6 | 3.93/ 73.9 | 3.78,3.88/ 63.4 | / |
| | D: α-D-Glcp-(1 | 5.41/ 102.6 | 3.58/ 74.3 | 3.72/ 75.8 | 3.43/ 72.2 | 3.96/ 75.4 | 3.75,3.84/ 63.3 | / |
| Rm-3 | B:4)-α-D-Glcp-(1-ABEE | 3.35,3.43/ 48.4 | 4.04/ 72.1 | 3.94/ 75.6 | 3.90/ 85.1 | 4.00/ 73.9 | 3.65,3.73/ 65 | / |
| | C: 4)-α-D-Glcp-(1 | 5.13/ 103.2 | 3.63/ 74.4 | 3.94/ 76.8 | 3.65/ 79.8 | 3.92/ 74.2 | 3.83/ 63.3 | / |
| | D: 4)-α-D-Glcp-(1 | 5.36/ 102.7 | 3.63/ 74.4 | 3.94/ 76.8 | 3.65/ 80.1 | 3.82/ 74 | 3.83/ 63.3 | / |
| | E: α-D-Glcp-(1 | 5.36/ 102.6 | 3.57/ 74.6 | 3.69/ 75.8 | 3.43/ 72.1 | 3.94/ 75.3 | 3.83/ 63.3 | / |

FIG. 29

Table 7 (Continued)

| Marker | Sugar Residues | Chemical shift | | | | | | |
|---|---|---|---|---|---|---|---|---|
| | | H-1/C-1 | H-2/C-2 | H-3/C-3 | H-4/C-4 | H-5/C-5 | H-6/C-6 | OCH$_3$ |
| Am-1 | B:6)-β-D-Gal$p$-(1-ABEE | 3.41/ | 4.14/ | 3.76/ | 3.70/ | 4.16/ | 3.73,3.98/ | / |
| | | 49.7 | 70.5 | 72.5 | 72.9 | 70.5 | 74.9 | |
| | C:β-4-O-Me-D-GalA$p$-(1 | 4.51/ | 3.38/ | 3.60/ | 3.34/ | 3.92/ | 176.3 | 3.51/63.1 |
| | | 105.6 | 75.8 | 77.8 | 84.6 | 76.8 | | |
| Am-2 | B:6)-β-D-Gal$p$-(1-ABEE | 3.44/ | 4.16/ | 3.75/ | 3.72/ | 4.17/ | 3.79,4.03/ | / |
| | | 49.6 | 70.5 | 72.5 | 72.9 | 71.6 | 74.9 | |
| | C: 6)-β-D-Gal$p$-(1 | 4.41/ | 3.57/ | 3.65/ | 3.95/ | 3.88/ | 3.88,4.01/ | / |
| | | 106.3 | 73.8 | 75.5 | 71.7 | 76.7 | 72.5 | |
| | D: β-4-O-Me-D-GalA$p$-(1 | 4.52/ | 3.38/ | 3.60/ | 3.35/ | 3.92/ | 176.3 | 3.51/ |
| | | 105.7 | 75.8 | 77.9 | 84.5 | 77 | | 63.1 |
| | ABEE Residues | C-1' | H-2',6'/C-2',6' | H-3',5'/C-3',5' | C-4' | C-7' | H-8''/C-8'' | H-9''/C-9' |
| Rm-1, Rm-2, Rm-3 | A: ABEE | 155.8 | 6.76/ 114.9 | 7.85/ 134.5 | 120.1 | 172.1 | 4.31/ 64.5 | 1.35/ 16.5 |
| Am-1, Am-2 | A: ABEE | 154.2 | 6.83/ 116.3 | 7.85/ 134.5 | 121.8 | 172.1 | 4.30/ 64.7 | 1.35/ 16.5 |

FIG. 29 (Continued)

Table 8

| PMAA | Linkage pattern | Molar ratio [a] | Ion fragmentation (m/z) |
|---|---|---|---|
| 2,3,4,6-Me4-Glc$p$ | 1-linked Glc$p$ | 1 | 43, 71, 87, 101, 117, 129, 145, 161, 205 |
| 2,3,6-Me3-Glc$p$ | 1,4-linked Glc$p$ | 6 | 43, 71, 101, 113, 117, 131, 143, 173, 233 |

FIG. 30

Table 9

| Polysaccharide | Molecular weight [a] | Sugar content [b] | Uronic acid content [c] | Protein content [d] | Monosaccharide composition [e] |
|---|---|---|---|---|---|
| RAP | 113±3 kDa | 88.03±3.51% | 4.21±0.21% | 2.90±0.16% | Glc: GalA: Gal: Ara=94:2.8:2.5:1.0 |
| ASP | 136±5 kDa | 66.3±1.46% | 37.1±0.88% | 4.65±0.28% | GalA: Gal: Glc: Ara=1.9:1.2:1.2:1.0 |

FIG. 31

Table 10

| Polysaccharides | Analytes | Repeatability (RSD%) | | LOQ [d] (μg/mL) | LOD [d] (μg/mL) | Spike recovery % (RSD% n=3) | | | | | |
|---|---|---|---|---|---|---|---|---|---|---|---|
| | | Intra-day (n=6) | Inter-day (n=3) | | | Low | RSD | Middle | RSD | High | RSD |
| RAP | RAW [a] | 4.81% | 5.79% | 0.5 | 0.25 | 96.2 | 3.62 | 86.7 | 6.36 | 84.9 | 5.21 |
| | DBT [b] | 4.21% | 4.74% | | | 87.2 | 5.44 | 83.3 | 4.98 | 86.2 | 3.24 |
| ASP | ASW [c] | 5.24% | 7.39% | 0.05 | 0.02 | 85.9 | 7.12 | 83.2 | 5.49 | 79.8 | 6.72 |
| | DBT [b] | 5.65% | 8.31% | | | 86.3 | 6.41 | 84.5 | 6.23 | 81.2 | 5.98 |

FIG. 32

Table 11

| | Peak No. | Rt (min) | m/z | H-ASP | H-DBTS |
|---|---|---|---|---|---|
| H-RAP | 1 | 11.63 | 490.1959 | + | + |
| | 2 | 11.07 | 652.249 | + | + |
| | 3 | 10.35 | 814.3058 | + | + |
| | 4 | 9.63 | 976.3611 | + | + |
| | 5 | 9.04 | 1138.411 | - | + |
| | 6 | 8.56 | 1300.463 | - | + |
| | 7* | 8.23 | 1462.518 | - | - |
| | 8 | 7.99 | 1624.553 | - | - |
| | 9 | 7.26 | 892.8162 ($^{2-}$) | - | - |
| | Peak No. | Rt (min) | m/z | H-RAP | H-DBTS |
| H-ASP | 1 | 11.65 | 490.1959 | + | + |
| | 2# | 11.03 | 680.2459 | - | - |
| | 3 | 10.73 | 518.1491 | - | - |
| | 4 | 10.26 | 814.3058 | + | + |
| | 5 | 9.48 | 976.3611 | + | + |
| | 6 | 8.95 | 652.249 | - | + |
| | 7 | 8.29 | 814.3027 | - | - |
| | 8 | 7.81 | 1138.421 | - | - |
| | 9 | 7.51 | 1300.475 | - | - |

FIG. 33

CHROMOPHORE-LABELED OLIGOSACCHARIDE MARKERS AND METHODS OF USE THEREOF

CROSS REFERENCE TO RELATED APPLICATIONS

This application claims priority to U.S. Provisional Patent Application Ser. No. 62/847,912 filed on May 14, 2019 and Ser. No. 62/871,205 filed on Jul. 8, 2019, which are hereby incorporated by reference in their entirety.

TECHNICAL FIELD

The present disclosure relates to a series of labeled oligosaccharide markers derived from the partial acid hydrolysis of polysaccharides in *Dendrobium officinale*, Radix Astragali, and Radix Angelica Sinensis and the method of using these markers in qualitative and quantitative authentication of herbs, such as *Dendrobium officinale*, Radix Astragali, and Radix Angelica Sinensis. The methods described herein can also be applied to the qualitative and quantitative analysis of polysaccharides in other natural materials and related products.

BACKGROUND

Qualitative and quantitative analysis of polysaccharides in herbal materials and Chinese medicine formulations remains a challenge due to the complexity and diversity of naturally occurring polysaccharides as well as the limited number of analytical methods that can be used with large molecular weight analytes.

At present, polysaccharides are typically analyzed using monosaccharide composition analysis or high-performance gel permeation chromatography (HPGPC) analysis of polysaccharide markers. As for monosaccharide composition, it is mainly based on the acid hydrolysis of the polysaccharides so as to obtain monosaccharide residues and their ratios. However, this method lacks specificity as similar monosaccharides compositions could be found in different polysaccharides. As for the method based on polysaccharide markers, though it works for certain herbs, other herbs do not contain such a symmetric and well-separated polysaccharide marker peaks in their HPGPC chromatogram. Furthermore, these polysaccharides can overlap together once herbs are mixed in a formulation, therefore resulting in a loss of specificity. Consequently, researchers have focused attention on developing oligosaccharides produced by hydrolysis of polysaccharides as a quality control strategy, because the generated oligosaccharides can retain part of the structural information of the original polysaccharide, and they are more specific when compared to monosaccharide analysis. However, there is huge difficulty in both detection and separation of oligosaccharides as they do not absorb ultraviolet wavelengths, which can complicate detection and have similar polarity and chromatographic behavior. Therefore, common separation techniques such as silica-gel chromatography, reverse-phase chromatography and gel permeation chromatography cannot be applied easily or directly.

*Dendrobium officinale*, Radix Astragali, and Radix Angelica Sinensis are herbs in many Chinese traditional formulas. Polysaccharides are the major components. Current pharmacology studies show that polysaccharides from the two herbs have wide bioactivities including immunomodulation, antitumor, anti-diabetes, etc.

However, until now, the quality control of herbal polysaccharides remains a difficulty blocking the research and development of polysaccharide-based products. Due to the large molecular mass, structural diversity and complexity, getting information from intact polysaccharides is hard. Methylation analysis, NMR analysis, and phenol-sulphuric acid method are commonly used in qualitative and quantitative analysis of polysaccharides, but none of them is able to determine specific polysaccharides in herb mixture.

As such, there still exists a need for improved quality control and autentication methods of polysaccharides in herbs, such as *Dendrobium officinale*, Radix Astragali, and *Radix Angelica Sinensis*.

SUMMARY

The challenges of separating and detecting polysaccharides in herbs and herbal products are herein overcome by derivatization of the polysaccharide hydrolysates with a multi-functional label, such as 2-aminobenzamide (2-AB), 2-aminopyridine (2-AP), PMP and 4-aminobenzoic acid ethyl ester (ABEE), which not only makes the labeled oligosaccharide markers UV-detectable, but also improves the separation of the of the labeled oligosaccharide markers.

Provided herein are ABEE labeled oligosaccharides useful for the qualitative and quantitative analysis of polysaccharides in *Dendrobium officinale*, Radix Astragali, and Radix Angelica Sinensis and other herbs or mixtures of herbs, and methods of use thereof.

It is a further objective of this disclosure to provide ABEE-labeled oligosaccharide markers produced from the partial acid hydrolysis of *Dendrobium officinale* polysaccharides (DOP), radix *Astragali polysaccharides* (RAP) and *Radix Angelica Sinensis* (ASP) polysaccharides useful for qualitative and quantitative analysis of DOP, RAP, ASP in herbal formulation by using the oligosaccharide markers.

In a first aspect, provided herein is a method for analyzing polysaccharide content in a test sample comprising at least one herb, the method comprising: providing a saccharide sample comprising oligosaccharides and monosaccharides obtained by partial acid hydrolysis of polysaccharides in the test sample; contacting the saccharide sample with 4-aminobenzoic acid ethyl ester (ABEE) or an analog thereof and a reducing agent thereby forming an ABEE labeled saccharide sample comprising one or more ABEE labeled saccharides; and analyzing the ABEE labeled saccharide sample using at least one analytical method thereby providing test sample polysaccharide content related data.

In a first embodiment of the first aspect, provided herein is the method of the first aspect wherein, the at least one herb is selected from the group consisting of *Dendrobium officinale*, Radix Astragali, and *Radix Angelica Sinensis*.

In a second embodiment of the first aspect, provided herein is the method of the first aspect further comprising the step of comparing the test sample polysaccharide content related data with one or more calibration curves prepared by using the interrelation between known concentrations of the one or more ABEE labeled saccharides in standard samples; and determining the concentration of at least one polysaccharide in the test sample.

In a third embodiment of the first aspect, provided herein is the method of the first aspect, wherein the polysaccharide content related data is used to authenticate the quality or the identity of the at least one herb.

In a fourth embodiment of the first aspect, provided herein is the method of the first aspect, wherein the at least one analytical method is selected from the group consisting of high performance liquid chromatography (HPLC), liquid chromatography-mass spectrometry (LC-MS) high-performance gel permeation chromatography (HPGPC).

In a fifth embodiment of the first aspect, provided herein is the method of the first aspect, wherein the analog of ABEE has the structure:

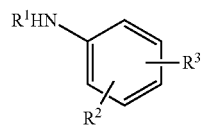

wherein $R^1$ is hydrogen or alkyl; $R^2$ is hydrogen, alkyl, cyano, alkoxyl, hydroxyl, dialkyl amine, ester, amide, urea; and $R^3$ is hydrogen, alkyl, cycloalkyl, heterocycloalkyl aryl, heteroaryl, amine, amide, urea, or $CO_2R^4$, wherein $R^4$ is hydrogen, alkyl, cycloalkyl, heterocycloalkyl aryl, or heteroaryl.

In a sixth embodiment of the first aspect, provided herein is the method of the first aspect, wherein the one or more ABEE labeled saccharides is selected from the group consisting of: ABEE labeled galacturonic acid (ABEE-GalA); ABEE labeled glucuronic acid (ABEE-GluA); ABEE labeled galactose (ABEE-Gal); ABEE labeled mannose (ABEE-Man); ABEE labeled glucose (ABEE-Glc); ABEE labeled arabinose (ABEE-Ara); ABEE labeled rhamnose (ABEE-Rha); ABEE labeled xylose (ABEE-Xyl); ABEE labeled fucose (ABEE-Fuc);

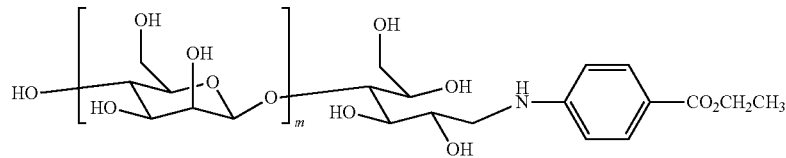

wherein m is a whole number selected from 0-10;

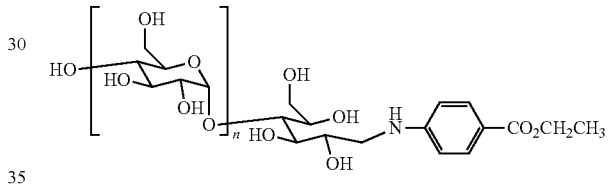

wherein n is a whole number selected from 0-10; and

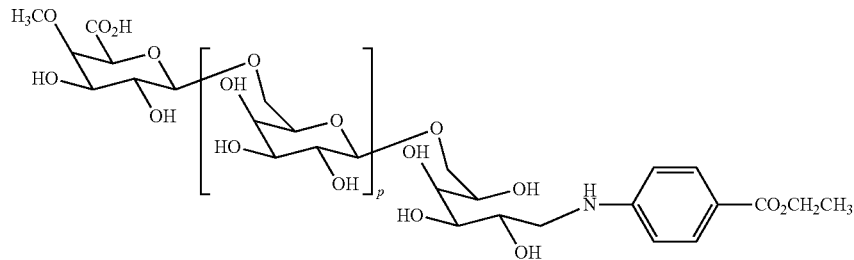

wherein p is a whole number selected from 0-10.

In a seventh embodiment of the first aspect, provided herein is the method of the first aspect, wherein the one or more ABEE labeled saccharides is selected from the group consisting of:

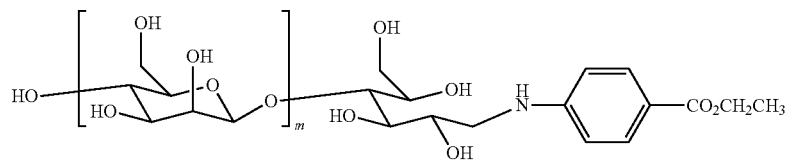

wherein m is a whole number selected from 3-9;

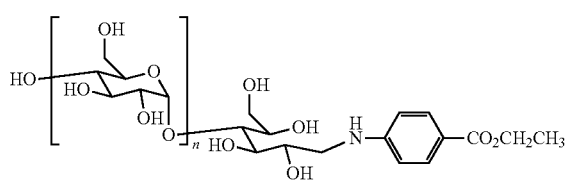

wherein n is 1, 2, or 7; and

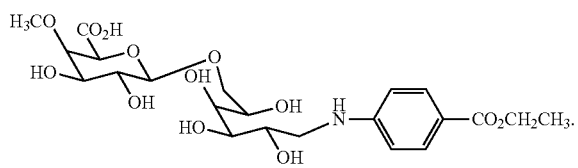

In an eighth embodiment of the first aspect, provided herein is the method of the first aspect, wherein the at least one herb is *Dendrobium officinale* and the one or more ABEE labeled saccharides is:

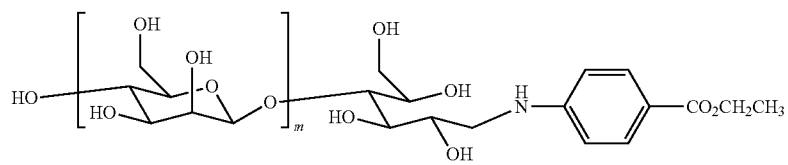

wherein m is a whole number selected from 3 or 4; or the at least one herb is selected from the group consisting of *Radix Astragali, Radix Angelica Sinensis*, and combinations thereof; and the one or more ABEE labeled saccharides is selected from the group consisting of:

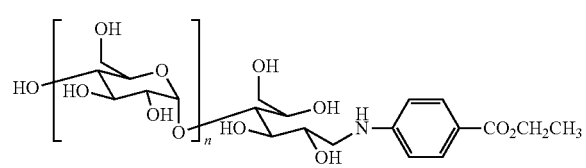

wherein n is 7; and

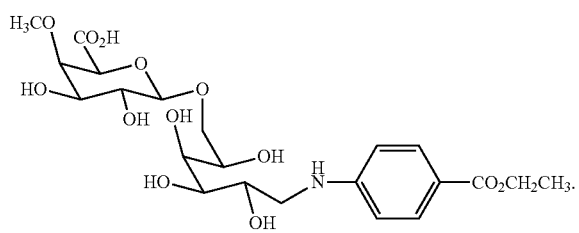

In a ninth embodiment of the first aspect, provided herein is the method of the first aspect, wherein the reducing agent is $NaBH_4$, $NaBH_3CN$, or $NaBH(OAc)_3$.

In a tenth embodiment of the first aspect, provided herein is the method of the first aspect, further comprising the step of contacting the test sample with a solvent thereby forming a polysaccharide sample.

In an eleventh embodiment of the first aspect, provided herein is the method of the tenth embodiment of first aspect, wherein the solvent comprises water.

In a twelfth embodiment of the first aspect, provided herein is the method of the tenth embodiment of first aspect further comprising the step of contacting the polysaccharide sample with an acid and water thereby forming the saccharide sample.

In a thirteenth embodiment of the first aspect, provided herein is the method of the twelfth embodiment of first aspect, wherein the acid is trifluoroacetic acid.

In a fourteenth embodiment of the first aspect, provided herein is the method of the thirteenth embodiment of first aspect, wherein at least 10% of the polysaccharides in the test sample are partially hydrolyzed.

In a second aspect, provided herein is a method for analyzing polysaccharide content in a test sample comprising at least one herb selected from the group consisting of *Dendrobium officinale*, Radix Astragali, and Radix Angelica Sinensis, the method comprising: contacting the test sample with a solvent comprising water thereby forming a polysaccharide sample; contacting the polysaccharide sample with a trifluoroacetic acid and water thereby forming a saccharide sample comprising oligosaccharides and monosaccharides; contacting the saccharide sample with 4-aminobenzoic acid ethyl ester (ABEE) and a reducing agent selected from the group consisting of $NaBH_4$ and $NaBH_3CN$ thereby forming an ABEE labeled saccharide sample comprising one or more ABEE labeled saccharides selected from the group consisting of:

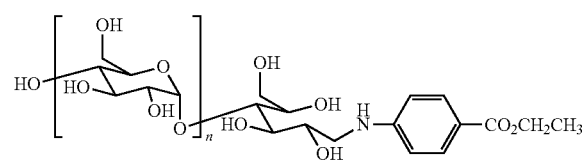

wherein n is 7;

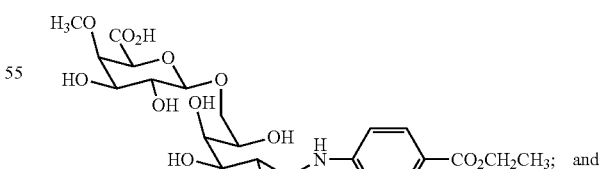

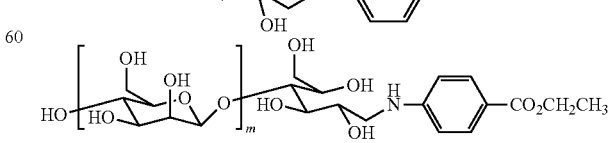

wherein m is a whole number selected from 3 or 4; and analyzing the ABEE labeled saccharide sample using at least one analytical method selected from the group consisting of LC-MS and HPGPC thereby providing test sample polysaccharide content related data.

In a first embodiment of the second aspect, provided herein is the method of second aspect, wherein the at least one herb is *Dendrobium officinale* and the one or more ABEE labeled saccharides is:

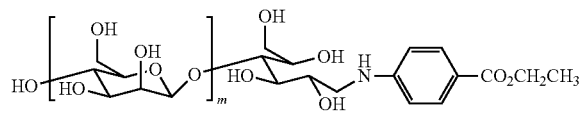

wherein m is a whole number selected from 3 or 4; or the at least one herb is selected from the group consisting of *Radix Astragali, Radix Angelica Sinensis*, and combinations thereof; and the one or more ABEE labeled saccharides is selected from the group consisting of:

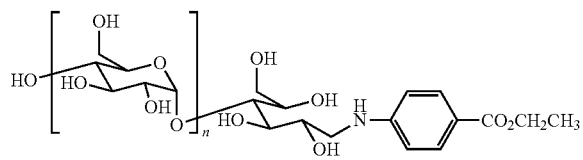

wherein n is 7; and

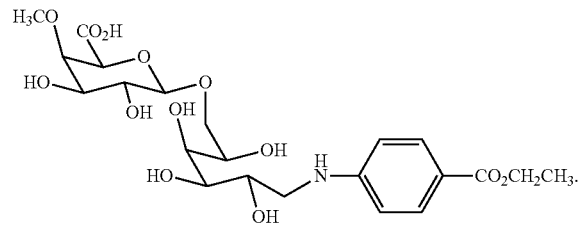

In a second embodiment of the second aspect, provided herein is the method of second aspect further comprising the step of comparing the test sample polysaccharide content related data with one or more calibration curves prepared by using the interrelation between known concentrations of the one or more ABEE labeled saccharides in standard samples; and determining the concentration of at least one polysaccharide in the test sample.

In a third embodiment of the second aspect, provided herein is the method of second aspect, wherein the polysaccharide content related data is used to authenticate the quality or the identity of the at least one herb.

Also provided herein are a series of labeled oligosaccharide markers and the use of these labeled oligosaccharide markers in the methods described herein. These oligosaccharides can be prepared from the saccharides and oligosaccharides in Radix Astragali and Radix Angelica Sinensis after partial acid hydrolysis and ABEE (or an analog thereof) label derivatization, comprising: separating the common and dominant component of the carbohydrates in samples according to the molecular distribution pattern. The sample have a number of polysaccharides, where the dominant polysaccharide component is the component of the samples having a largest number of polysaccharides in said sample; mildly hydrolyzing the dominant polysaccharide component by acid, releasing oligo/monosaccharides; and labeling the hydrolysates with a label, such as ABEE; and isolating the representative oligosaccharide markers; and elucidating the structure.

In certain embodiments, the step of providing generally chemical molecule distribution profiles includes performing the size exclusion chromatography through high performance gel permeation chromatography coupled with a charged aerosol detector (HPGPC-CAD).

In certain embodiments, separating the dominant polysaccharide is conducted by simply one-step precipitation using 10-90% v/v ethanol, resulting in a crude polysaccharide.

In certain embodiments, hydrolyzing the separated polysaccharide by mild acid, releasing the free oligosaccharides and the released oligosaccharides are labelled with ABEE or an analog thereof, resulting in stable labeled-oligosaccharides.

In certain embodiments, the acid used for partial acid hydrolysis is trifluoroacetic acid (TFA).

In certain embodiments, representative labeled-oligosaccharide markers are isolated using C18 preparative/semi-preparative columns.

In certain embodiments, the structure of isolated markers is elucidated by combination analysis of MS, monosaccharide composition, methylation and NMR.

Those skilled in the art will appreciate that the invention described herein is susceptible to variations and modifications other than those specifically described.

The present invention includes all such variation and modifications. The invention also includes all of the steps and features referred to or indicated in the specification, individually or collectively, and any and all combination or any two or more of the steps or features.

Throughout the present specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the invention belongs.

Other aspects and advantages of the present invention will be apparent to those skilled in the art from a review of the ensuing description.

BRIEF DESCRIPTION OF THE DRAWINGS

The above and other objects and features of the present disclosure will become apparent from the following description of the invention, when taken in conjunction with the accompanying drawings, in which:

FIG. 23 shows Table 1 that presents the quantitative results of carbohydrate components in the investigated *Dendrobium officinale* samples (mg/g) based on sugar composition analysis and HPGPC analysis. Note: $^a$ Molecular weight was determined by HPGPC-CAD using the established molecular weight-retention time calibration curve; $^b$ sugar content was determined by phenol-sulfuric acid method; $^c$ DOP content was determined by DOP standard calibration curve by HPGPC-CAD.

FIG. 24 shows Table 2 that lists the molecular weight, DP value, monosaccharide composition and glycosidic linkage of the oligosaccharide markers.

FIG. 25 shows Table 3 that lists the chemical shift assignments of $^1$H-NMR and $^{13}$C-NMR spectra of all the oligosaccharide markers based on HSQC, $^1$H-$^1$H COSY and HMBC spectra.

FIG. 26 shows Table 4 that lists the linearity range and linearity coefficient of Te-Man and Pen-Man FIG. 27 shows Table 5 that lists the repeatability and accuracy of *Dendrobium officinale* water extract, Tonic Vitality Confection (TVC) and Granule Dendrobii (GD).

FIG. 28 shows Table 6 that lists the content of DOP (mg/g) in *Dendrobium officinale* water extracts, Tonic Vitality Confection (TVC) and Granule Dendrobii (GD). % content of DOP=concentration of DOP in sample/10×100%.

FIG. 29 shows Table 7 that shows chemical shift assignments of $^1$H-NMR and $^{13}$C-NMR spectra of Rm-1, Rm-2 and Rm-3, Am-1 and Am-2 based on HSQC, $^1$H-$^1$H COSY, DEPT-135 and HMBC spectra.

FIG. 30 shows Table 8 that shows the linkage analysis of Rm-3 by methylation and GC-MS. Note: $^a$ The molar ratios of residues were estimated by the integration of their peak areas in total ion chromatograms.

FIG. 31 shows Table 9 that shows the basic chemical characteristics of the standard polysaccharide. Note: The data was obtained by determining three batches of standard polysaccharide prepared from individual herbs. The data was shown as Mean±SD (n=3). Note: $^a$ Molecular weight was determined by HPGPC-CAD using the established molecular weight-retention time calibration curve; $^b$ sugar content was determined by phenol-sulfuric acid method; $^c$ uronic acid content was determined by M-phenyl phenol method; $^d$ protein content was obtained by BCA method; $^e$ monosaccharide composition was determined after ethyl p-aminobenzoate (ABEE) derivatization; the ratio was calculated according to the peak area percentage.

FIG. 32 shows Table 10 that shows the validation result of established quantitative method. Note: $^a$ Radix Astragali water extract (RAW), $^b$ Radix Angelica sinensis water extract (ASW) and $^c$ Danggui Buxue Tang (DBT) (1:1) were used in method validation. $^d$ The limits of detection (LOD) and limits of quantitation (LOQ) of Rm and Am under the present conditions were determined at an S/N (signal to noise) of about 3 and 10.

FIG. 33 shows Table 11 shows the oligosaccharides marker selection based on the retention time and mass-to-charge ratio. Note: 1) RAP: Radix Astragali polysaccharide; ASP: Radix Angelica Sinensis polysaccharide; DBTS: Danggui Buxue Tang (Radix Astragali: Radix Angelica Sinensis=5:1) without RAP and ASP; H: partial acid hydrolysis catalyzed by 1.0 mol/L TFA at 80° C. for 2 h; 2) The ABEE-labeled oligosaccharides detected in the sample was marked as "+", otherwise as "−"; 3) The ABEE-labeled oligosaccharides which can be used for discriminate RAP and ASP in DBT are in bolded font; 4) The final markers used for RAP and ASP were marked by asterisk (*) and hash symbol (#), respectively.

DETAILED DESCRIPTION

Figure 1:
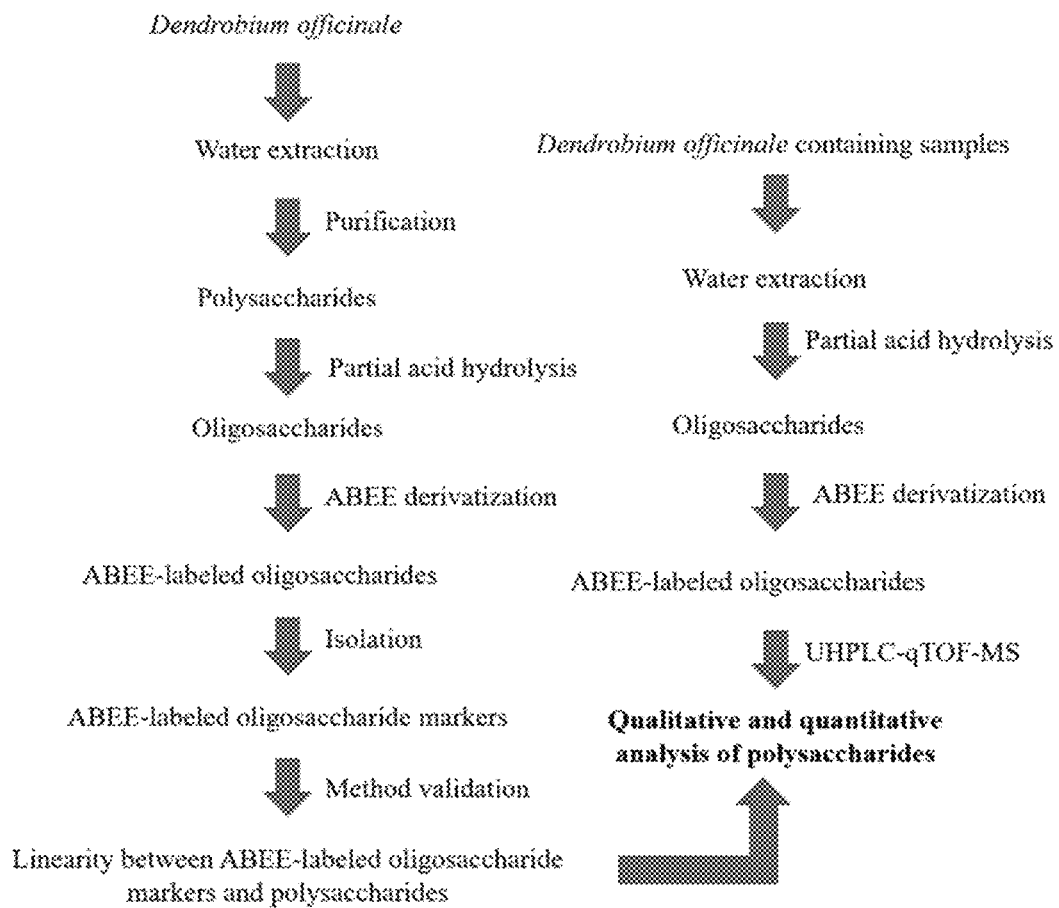
FIG. 1 is a flowchart shows the utilization of fluorescence-labeled oligosaccharide markers derived from *Dendrobium officinale* polysaccharide to determine the content of *Dendrobium officinale* polysaccharide in *Dendrobium officinale* containing herb formula.

The methods described herein have several advantages when compared with the current analytical methods. First, the labeled oligosaccharides and saccharides described herein are unique chemical markers of herbs, such as DOP, RAP, and ASP, which are not naturally occurring, but are created based on the polysaccharide itself. Therefore, they are able to represent the characteristics of DOP, RAP, and ASP in both qualitative and quantitative analysis. Second, labeling can provide UV absorption and increase the polarity difference between the chains of oligosaccharide markers. This can improve the isolation efficiency to obtain the markers. Third, labeling the oligosaccharides and saccharides can improve the ionization efficiency in the mass spectrometer detector. As a result, the quantitative detection limit can be greatly improved.

The present disclosure provides a general method for analyzing polysaccharides in herbs. While the methods described herein are exemplified using the model herbs *Dendrobium officinale*, Radix Astragali, Radix Angelica Sinensis, and combinations thereof, the present disclosure contemplates application of the methods described herein to all polysaccharide containing herbs.

Provided herein is a method for analyzing polysaccharide content in a test sample comprising at least one herb, the method comprising: providing a saccharide sample comprising oligosaccharides and monosaccharides obtained by partial acid hydrolysis of polysaccharides in the test sample; contacting the saccharide sample with 4-aminobenzoic acid ethyl ester (ABEE) or an analog thereof and a reducing agent thereby forming an ABEE labeled saccharide sample comprising one or more ABEE labeled saccharides; and analyzing the ABEE labeled saccharide sample using at least one analytical method thereby providing test sample polysaccharide content related data.

The method provided herein produces polysaccharide content related data that can provide e.g., directly or indirectly, at least one of: identification of one or more polysaccharides present in the herb, the concentration of one or more polysaccharides present in the herb, the identity of the herb, the quality of the herb, the identity of one or more herbs in an herbal product, the concentration of one or more herbs in an herbal product, the quality of an herbal product.

The methods provided herein can be applied to any herb comprising one or more polysaccharides. In certain embodiments, the at least one herb is selected from the group consisting of *Dendrobium officinale*, Radix Astragali, Radix Angelica Sinensis, combinations thereof, and related herbal products. Related herbal products can comprise Danggui Buxue Tang (DBT) prepared by mixing Radix Astragali and Radix Angelica Sinensis.

The test sample comprising at least one herb can be prepared by extraction to yield the polysaccharide sample, which can then be treated to partial acid hydrolysis to yield the saccharide sample.

Extraction of the test sample comprising at least one herb can be accomplished using any solvent in which the polysaccharides present in the test sample are at least partially soluble. In certain embodiments, the solvent used for extraction is water, an alcohol, an ether, or combinations thereof. Exemplary solvents that are useful of extraction of the polysaccharides present in the test sample include, but are not limited to water, methanol, ethanol, 1-propanol, 2-propanol, glycerol, glycol, ethylene glycol dimethyl ether, diglyme, polyethylene glycol, polyethylene glycol dimethyl ether, and combinations thereof. In certain embodiments, the extraction solvent is water.

Extraction of the test sample can be conducted at a temperature between 20° C. to 120° C. In certain embodiments, the extraction is conducted at a temperature between 20° C. to 100° C.; 50° C. to 100° C.; 70° C. to 100° C.; 80° C. to 100° C.; or 90° C. to 100° C.

The acid used for the partial acid hydrolysis of the polysaccharide sample is not limited to any particular type of acid. Suitable acids may comprise relatively non-reactive anion(s) (e.g., anions that are not a strong oxidants and/or nucleophiles). Exemplary acids include, but are not limited to, HCl, $H_2SO_4$, $HSO_4^-$, $H_3PO_4$, $H_2PO_4^-$, $MeS_2OH$, $CF_3SO_2OH$, $PhSO_2OH$, $TolSO_2OH$, TFA, fumaric acid, maleic acid, succinic acid, benzoic acid, acetic acid, citric acid, tartaric acid, and combinations thereof.

The partial acid hydrolysis of the polysaccharide sample can be conducted in any solvent. In certain embodiments, the partial acid hydrolysis is conducted in a polar protic solvent, such as water, an alcohol, an ether, or combinations thereof. Exemplary solvents include, but are not limited to water, methanol, ethanol, 1-propanol, 2-propanol, glycerol, glycol, ethylene glycol dimethyl ether, diglyme, polyethylene glycol, polyethylene glycol dimethyl ether, and combinations thereof.

In certain embodiments, the partial acid hydrolysis of the polysaccharide sample is conducted in a solvent comprising alcohol and water. The alcohol and water can be present in any ratio. In certain embodiments, the alcohol is present with water at a concentration between 10% and 99%, 20% and 99%, 30% and 99%, 40% and 99%, 50% and 99%, 50% and 90%, 50% and 80%, 50% and 70%, or 55% and 65%. In certain embodiments, the partial acid hydrolysis of the polysaccharide sample is conducted in a solvent comprising methanol is present with water at a concentration between 50% and 70%.

The partial acid hydrolysis of the polysaccharide sample can be conducted at a temperature between 20° C. to 120° C. In certain embodiments, the partial acid hydrolysis of the polysaccharide is conducted at a temperature between 20° C. to 100° C.; 50° C. to 100° C.; 60° C. to 100° C.; 60° C. to 90° C.; 65° C. to 85° C.; or 70° C. to 85° C.

The polysaccharide sample can be subjected to the partial acid hydrolysis between 10 minutes and 3 hours. In certain embodiments, the polysaccharide sample is subjected to the partial acid hydrolysis between 0.5-3 hours; 1-3 hours; or 2-3 hours.

Partial acid hydrolysis of the polysaccharide sample yields at least some oligosaccharides with a reduced molecular weight resulting from chain scission caused during hydrolysis of the polysaccharides present in the polysaccharide sample. In certain embodiments partial acid hydrolysis of the polysaccharide sample results in the partial hydrolysis of at least 1%, at least 5%, at least 10%, at least 20%, at least 30%, at least 40%, at least 50%, at least 60%, at least 70%, at least 80%, at least 90%, at least 95%, or more of the polysaccharides in the polysaccharide sample is converted to oligosaccharides or monosaccharides.

In order to improve the visualization and the chromatographic separation of the oligosaccharides and monosaccharides in the saccharide sample 4-aminobenzoic acid ethyl ester (ABEE) or an analog thereof is covalently bonded to the oligosaccharides and monosaccharides in the saccharide sample by a reductive amination reaction.

Analogs of ABEE that are suitable for use in the methods described herein can be represented by the structure:

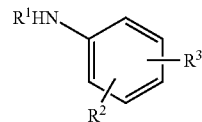

wherein $R^1$ is hydrogen or alkyl; $R^2$ is hydrogen, alkyl, cyano, alkoxyl, hydroxyl, dialkyl amine, ester, amide, urea; and $R^3$ is hydrogen, alkyl, cycloalkyl, heterocycloalkyl aryl, heteroaryl, amine, amide, urea, or $CO_2R^4$, wherein $R^4$ is hydrogen, alkyl, cycloalkyl, heterocycloalkyl aryl, or heteroaryl.

In certain embodiments, $R^1$ is hydrogen, methyl, or ethyl. In certain embodiments, $R^2$ is hydrogen or alkyl. In certain embodiments, $R^3$ is $CO_2R^4$, wherein $R^4$ is alkyl. In certain embodiments, $R^1$ is hydrogen; $R^2$ is hydrogen or alkyl; and $R^3$ is $CO_2R^4$, wherein $R^4$ is alkyl.

When the saccharide sample is contacted with ABEE or an analog thereof and a reducing agent a reductive coupling reaction can occur resulting in the covalent conjugation of the ABEE or an analog thereof with the oligosaccharides and saccharides present in the saccharide sample thereby yielding an ABEE labeled saccharide sample comprising one or more ABEE labeled saccharides.

Numerous methodologies for accomplishing reductive amination reactions are known in the art. While borohydride reductive amination is exemplified herein, the present disclosure contemplates any suitable method for accomplishing the reductive amination including both metal catalyzed, metal mediated, and other non-metal catalyzed methods. The selection of a suitable reductive amination method is well within the skill of a person of ordinary skill in the art.

In certain embodiments, the reductive amination is accomplished using a reducing agent selected from $NaBH_4$, $NaBH_3CN$, and $NaBH(OAc)_3$. In certain embodiments, the reducing agent is $NaBH_4$ or $NaBH_3CN$.

The reductive amination can occur in any solvent. In certain embodiments, the solvent is water, an alcohol, an ether, or combinations thereof. Exemplary solvents include, but are not limited to water, methanol, ethanol, 1-propanol, 2-propanol, glycerol, glycol, ethylene glycol dimethyl ether, diglyme, polyethylene glycol, polyethylene glycol dimethyl ether, tetrahydrofurn, dioxane, tetrahydropyran, and combinations thereof.

The reductive amination can be conducted at a temperature between 20° C. to 120° C. In certain embodiments, the reductive amination of the saccharide is conducted at a temperature between 20° C. to 100° C.; 50° C. to 100° C.; 50° C. to 90° C.; 50° C. to 80° C.; 50° C. to 70° C.; or 60° C. to 70° C.

The one or more ABEE (or an analog thereof) labeled saccharides products of the reductive amination reaction can comprise the ABEE label (or an analog thereof) covalently bonded to the C1 carbon of the reducing end of the oligosaccharide or saccharide as exemplified below:

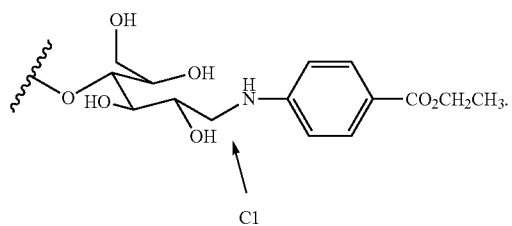

The ABEE (or an analog thereof) labeled saccharide sample can comprise one or more ABEE (or an analog thereof) labeled saccharides resulting from the reductive amination of the oligosaccharide or monosaccharide partial hydrolysis product of any naturally occurring polysaccharide present in herbs.

The ABEE (or an analog thereof) labeled saccharide sample can comprise one or more ABEE (or an analog thereof) labeled monosaccharides and/or one or more ABEE (or an analog thereof) labeled oligosaccharides.

The one or more ABEE labeled saccharides can be selected from the group consisting of: ABEE labeled galacturonic acid (ABEE-GalA); ABEE labeled glucuronic acid (ABEE-GluA); ABEE labeled galactose (ABEE-Gal); ABEE labeled mannose (ABEE-Man); ABEE labeled glucose (ABEE-Glc); ABEE labeled arabinose (ABEE-Ara); ABEE labeled rhamnose (ABEE-Rha); ABEE labeled xylose (ABEE-Xyl); ABEE labeled fucose (ABEE-Fuc);

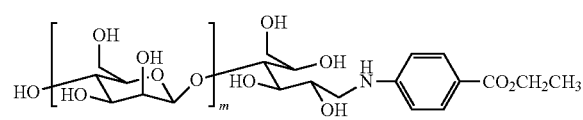

wherein m is a whole number selected from 0-10, 1-10, 2-10, 3-10, or 3-9;

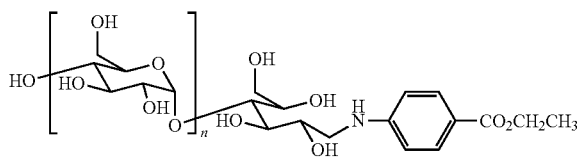

wherein n is a whole number selected from 0-10, 1-10, 1-9, 1-8, 1-7, 2-7, or 1-2; and

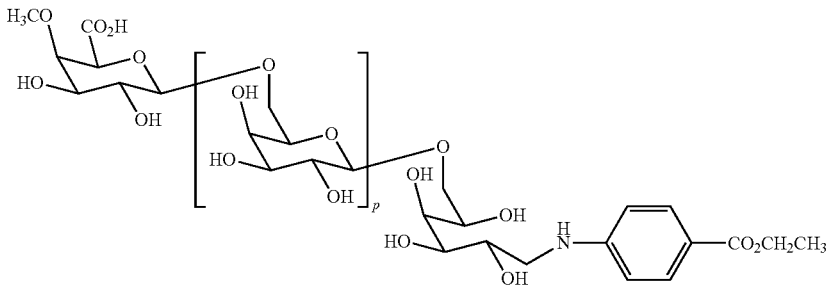

wherein p is a whole number selected from 0-10, 0-9, 0-8, 0-7, 0-6, 0-5, 0-4, 0-3, 0-2, or 0-1.

In certain embodiments, the one or more ABEE labeled saccharides is selected from the group consisting of:

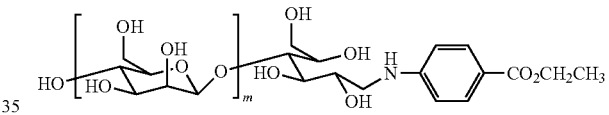

wherein m is a whole number selected from 3-9;

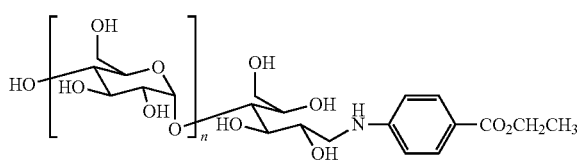

wherein n is 1, 2, or 7; and

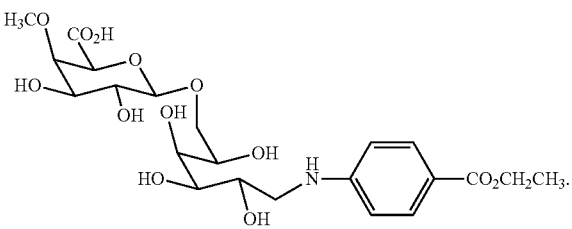

The resulting ABEE labeled saccharide sample can then be analyzed using at least one analytical method thereby providing test sample polysaccharide content related data.

The test sample polysaccharide content related data can comprise one or more of the following parameters: liquid chromatography retention time, liquid chromatography peak area, mass fragmentation (mass, fragment patterns, and mass peak intensity), optical absorption (e.g., UV absorption).

Any analytical method can be used to analyze the ABEE labeled saccharide sample. In certain embodiments, the at least one analytical method is selected from the group consisting of microscopy, macroscopy, spectrometry, spectroscopy, chromatography, and combinations thereof. Exemplary analytical methods include, but are not limited to, mass spectrometry, high performance thin layer chromatography, Fourier transform infrared spectroscopy, ultraviolet-visible spectroscopy, thin layer chromatography, gas-liquid chromatography (GC), high-performance liquid chromatography (HPLC), liquid chromatography-mass spectrometry (LC-MS), gas chromatography-mass spectrometry (GC-MS), nuclear magnetic resonance (NMR), antibody detection methods, Raman spectroscopy, capillary electrophoresis, liquid chromatography, gel permeation chromatography, ion chromatography, and combinations thereof. In certain embodiments, the at least one analytical method is selected from the group consisting of HPLC, LC-MS, and HPGPC. In instances in which the ABEE labeled saccharide sample comprises a mixture of ABEE labeled saccharides, the analytical method can comprise one or more analytical methods that are capable of physically separating the components of the mixture, such as an analytical method comprising chromatography.

In instances in which the method is used to quantify the concentration of one or more polysaccharides present in the at least one herb, the method can further comprise comparing the test sample polysaccharide content related data with one or more calibration curves prepared by using the interrelation between known concentrations of the one or more ABEE labeled saccharides in standard samples; and determining the concentration of at least one polysaccharide in the test sample.

Taking *Dendrobium officinale* as a model herb, to demonstrates how to utilize the oligosaccharide markers produced from DOP to develop a quality control method for the qualitative and quantitative analysis of DOP in the commercial products and Chinese medicine decoction. The present method can involve several steps. As shown in FIG. 1, at the beginning, DOP can be subjected to partial acid hydrolysis so as to produce the oligosaccharide markers. The oligosaccharide markers can then be labeled with ABEE so that they can be analyzed by UHPLC-qTOF-MS-DAD and isolated by the preparative HPLC-DAD. After that, the linearity relationship between the oligosaccharide markers and DOP can be developed by method validation. Thus, this method has been validated in order to ensure the accuracy of the analytical results.

The present disclosure provides a method for authenticating a sample of herbal material from *Dendrobium officinale*, comprising: providing a chemical fingerprint of the oligosaccharide fragments of the polysaccharides in the sample upon partial acid hydrolysis; identifying one or more dominant oligosaccharide markers from the partial acid hydrolysis of polysaccharide (DOP) by labeling them with fluorescent tag ABEE so as to be analyzed UHPLC-qTOF-MS-DAD; isolating the oligosaccharide markers by preparative HPLC; authenticating said sample of herbal material using the oligosaccharide markers.

The LC-MS results can provide identification of oligosaccharide markers based on retention time and mass spectrum.

The methods disclosed herein are capable of authenticating herbs in a test sample using the one or more oligosaccharide markers is conducted by analyzing the partial hydrolysis of the sample and labeling with ABEE, followed by LC-MS detection.

It provides the method wherein the isolation of labeled oligosaccharide markers includes the precipitation and filtration of the polysaccharides (DOP) in priority.

It provides the method wherein the filtration is performed by an ultracentrifugal filtration while the precipitation is conducted by using 60% (v/v) ethanol.

It provides a method of preparing the oligosaccharide markers for use in qualitative and quantitative authentication of a sample of an herbal material from *Dendrobium officinale*, comprising: providing a chemical fingerprint of the carbohydrates in the sample based on partial acid hydrolysis; identifying one or more oligosaccharide markers in the sample, where the one or more oligosaccharide markers represents the existence of the specific polysaccharides in the sample; analyzing the oligosaccharide markers in qualitative and quantitative authentication of said sample.

Material and Chemicals

Six batches of authentic *Dendrobium officinale* samples were purchased from certified production areas of different companies and were from different provinces in mainland China (Table 1, FIG. 23). The voucher specimens were deposited at School of Chinese Medicine, Hong Kong Baptist University, Hong Kong, China. Four samples of confection (Tonic Vitality Confection, TVC) were collected from Hogor Zhuangyuan Co., Ltd. (Yunnan Province, China), while one sample of granules (Granule Dendrobii, GD) was purchased from Zhejiang Tianhuang Pharmaceutical Co., Ltd. (Zhejing Province, China).

Reference standard of D-glucose (Glc) and D-mannose (Man) were purchased from Sigma (St. Louis, USA). All of them were confirmed by their MS spectra before use. p-aminobenzoic acid ethyl ester (ABEE) and sodium cyanoborohydride for oligosaccharide derivatization were bought from Sigma (St. Louis, Mo., USA). Trifluoroacetic acid (TFA), glacial acetic acid and formic acid (analytical grade) were also obtained from Sigma (St. Louis, USA). Methanol (HPLC grade), acetonitrile (HPLC grade), diethyl ether (HPLC grade) were purchased from RCI Labscan Ltd. (Bangkok, Thailand) while ethanol (ACS grade) was acquired from Merck (Darmstadt, Germany). Deionized water was prepared by Millipore Milli Q-Plus system (Millipore, Bedford, Mass., USA).

The dried powder (1.5 g) or fresh pulp (3 g) were treated twice with 10 mL of deionized water at 100° C. for 2 hours and filtered. The combined extracts were centrifuged at 4000 rpm, 10 min and the supernatant were obtained. They were then concentrated on a rotary evaporator under reduced pressure at 55° C. After that, the concentrated solution was precipitated using a 60% ethanol solution in water with vigorous stirring. The solution was allowed to stay overnight at 4° C., and the precipitate was obtained by centrifugation at 4000 rpm, 10 min. The precipitate was then washed with 80% ethanol in water to remove any impurities. Finally, the precipitate was placed in the vacuum dryer to remove solvent.

Partial Acid Hydrolysis and ABEE Derivatization

The precipitate obtained from water extraction and ethanol precipitation was then subjected to partial acid hydrolysis by dissolving all of the precipitate yielded from the extraction step in 2 mL 1M TFA aqueous solution and placed in 75° C. hot water bath for 2 hr. TFA was removed from the hydrolyzed sample under the assist of methanol by rotatory evaporator afterwards.

ABEE labeling was conducted by dissolving the all of the product collected in the partial hydrolysis step into 1 mL of deionized water. 200 μL of the solution was transferred into to 2 mL centrifuged tube followed by 80 μL acetic acid, 80 μL of a 1.4 M aqueous solution of sodium cyanoborohydride (NaBH$_3$CN) and 400 μL of a 0.6 M ABEE in methanol. The solution was then placed in 65° C. hot water bath for 2 hours. After that, 300 μL deionized water was added for the purpose of precipitating excess ABEE reagent. The mixture was then extracted 5 times with 700 μL of diethyl ether and the upper layer was discarded to remove the excess ABEE reagent. Finally, the water layer was dried by by using a vacuum dryer. The dried solid was then redissolved in 300 μL 60% methanol in water and was subjected to UPLC-qTOF-MS-DAD analysis.

UHPLC-Q-TOF-MS-DAD Analysis

The acid hydrolysates were separated and detected on an ultra-high performance liquid chromatography-quadrupole time-of-flight mass spectrometry technique. UHPLC data were produced on an Agilent 1290 UHPLC system (Agilent Technologies, Santa Clara, USA) equipped with a binary pump, a thermostatic column compartment, an auto-sampler, and a degasser and a diode-array detector (DAD). The system was controlled with Mass Hunter B.06 software. The chromatographic column Waters ACQUITY UPLC BEH C18 column (2.1×100 mm, 1,7 μm) was used and eluted with a gradient elution of 0.1% formic acid in water (A) and 0.1% formic acid in acetonitrile (B) 0-5 min: 90% A; 5-18 min: 90-82% A; 18-23 min: 82-75% A; 23-26 min: 75-0% A; 26-29 min: 0% A; 29-29.1 min: 0-90% A; 29.1-34 min: 90% A. The flow rate was at 0.3 mL/min. The temperature was at 30° C. The injection volume was 2 μL. The MS condition was in negative mode. The optimized operating parameters in the negative ion mode were as follows: nebulizing gas (N$_2$) flow rate, 8.0 L/min; nebulizing gas temperature, 300° C.; Jet Stream gas flow, 8 L/min; sheath gas temperature, 350° C.; nebulizer, 45 psi; capillary, 3500 V; skimmer, 65 V; Oct RFV, 600 V; and fragmentor voltage, 150 V. Dry temperature was set to 180° C. Quadrupole ion energy was set to 3 eV as well as the collision cell collision energy. The analysis was also monitor at the wavelength of 305 nm by DAD.

Fractionation of Oligosaccharide Markers by Preparative HPLC C18-UV

For the sake of isolating the target oligosaccharides from the hydrolysate mixture produced from the partial acid hydrolysis, preparative HPLC was used to separate the hydrolysate into three fractions. The separation was achieved on the Waters 2545 Quaternary Gradient Module equipped with an autosampler and the 2489 TUV Detector. Samples were fractionated through a GROM Saphir 110 C18 column (300×40 mm, 12 μm) (Grace, Columbia, Md., USA). The mobile phase compromised of water (A) and acetonitrile (B) with gradient 0-30 min, 85% A; 30-50 min, 85% A-80% A; 50-60 min, 80% A-70% A; 60-80 min, 70% A-0% A; 80-100 min, 0% A. In order to facilitate the isolation and purification of the target oligosaccharide markers, the chromatogram has been divided into three fractions.

Purification of the Oligosaccharide Markers

The fractionated HDOP will be further purified through HPLC-DAD system. The purification was achieved through an Agilent 1100 series HPLC system (Agilent, Palo Alto, Calif., USA.) equipped with a binary pump, a thermostatic column compai intent, an auto-sampler, and a degasser and a diode-array detector (DAD). Each time, samples at the concentration of 40 mg/mL was purified through Alltima C$_{18}$ column (240×10 mm, 10 μm) (Grace, Columbia, Md., USA). The mobile phase compromised of water with 0.1% formic acid (A) and acetonitrile (B) with an isocratic elution at the flow rate 2.3 mL/min. The column temperature was set to 30° C. The purification process was monitor under UV detector at the wavelength of 305 nm.

Sequence Determination of Oligosaccharide Markers

After the oligosaccharide markers has been isolated and purified, they will be subjected to sequence determination to reveal the connection of the saccharide units. In the determination, about 1 mg of the labeled oligosaccharides marker was needed to undergo partial acid hydrolysis. In detail, 1 mL of 1M TFA was added and mixed well with the sample. After that, the reaction mixture was placed in a 100° C. dry bath heater for 2 hours. After cooling to room temperature, TFA was removed using a rotatory evaporator with the help of methanol. Afterwards, the reaction mixture was redissolved in 200 μL 60% methanol in water and analyzed by UHPLC-qTOF-MS. For the first analysis, the saccharide unit on reducing end of the oligosaccharide marker can be interpreted as only the reducing end was attached with ABEE label while the dissociated part cannot be observed in the UPLC-MS chromatogram. In order to recognize the dissociated part, the solution will be re-labeled with ABEE reagents again following the aforementioned method and analyzed by UHPLC-qTOF-MS again. After the UHPLC-qTOF-MS, some new peaks would appear when compared to the first chromatogram. By aligning with the known sequence, it is able to determine the unknown dissociated part sequence referring to the retention time and the mass spectrum. This sequencing analysis has to be done from the lower degree of polymerization markers to the higher degree one so as to establish a profile of oligosaccharide database regarding the retention time and the mass spectrum information.

Glycosidic Linkage by Methylation Reaction and GC-MS Analysis

In order to investigate the glycosidic linkages of the oligosaccharide markers, methylation reaction was needed. In this study, the methylation method was referred to the method of Needs and Selvendran el al., 1993 with some modification. Generally, dried sample (about 3-4 mg) was fully dissolved in 4 Å molecular sieve-dried DMSO (2 mL) and incubated with NaOH dry fine powder (20 mg) for 1 hour. Subsequently, 0.8 mL methyl iodide was added slowly into the sample which was placed in an ice bath. After the addition of methyl iodide, the reaction mixture was allowed to stand for 30 min. The reaction was then quenched by the addition of 1 mL deionized water. Excess methyl iodide was removed by rotary evaporator before the methylate was hydrolyzed by a 4 mL 2M solution of TFA in water at 110° C. for 2 hours in an oven. After the acid hydrolysis, the acid was removed and the hydrolysate was allowed to undergo reduction reaction for 3 hours by the addition of 30 mg NaBH$_4$. Then, the reaction mixture was acetylated by adding 3 mL acetic anhydride for 1.5 hours at 100° C. followed by evaporation with toluene to remove excess reaction reagents. Finally, the sample was partitioned with deionized water-chloroform (1:1, v/v) and the water layer was discarded before analyzing the contents of the organic layer by GC-MS.

Nuclear Magnetic Resonance (NMR) Spectroscopy

The sample for NMR spectroscopy was prepared by dissolving about 15-20 mg of isolated oligosaccharide in 0.5 mL $D_2O$ and was transferred to a regular 5 nm NMR tube. The $^1H$ and $^{12}C$ NMR spectra of these purified oligosaccharides were obtained via Bruker Avance 400 spectrometer (Bruker Co., Germany) at 25° C., at 400 and 100 MHz respectively. Water suppression experiment was performed. Chemical shifts were expressed in ppm and calibrated by reference shift: 0 ppm for $^{13}C$ NMR (TMS) while 4.80 ppm for $^1H$ NMR (HDO). All the data was evaluated by MestReNova. 2D $^1H$-$^1H$ correlation NMR spectroscopy (COSY), 2D $^1H$-$^{13}C$ heteronuclear multiple-bond NMR spectroscopy (HMBC) and 2D $^1H$-$^{13}C$ heteronuclear single-quantum coherence spectroscopy (HSQC) were also conducted following the standard Bruker pulse sequences.

UHPLC-qTOF-MS Quantitative Method Validation

The UHPLC-qTOF-MS method for quantitative analysis of the isolated oligosaccharide markers and the relationship of their content to the content of polysaccharides were validated in terms of linearity, sensitivity, precision, accuracy and stability. Aqueous stock solution of each of the oligosaccharide markers were diluted to appropriate concentrations by 60% methanol for the construction of calibration curve. Six concentrations of the marker solution were analyzed in triplicates, and the calibration curve were constructed by plotting the instrumental responsive signals versus the concentrations of the analyte. The linearity was evaluated by regression coefficient (r) or determination coefficient ($R^2$) of the calibration curves. The precision of the analytical method was determined by evaluating intra-day and inter-day variations. The analysis was repeated six times in the same day and additionally on three consecutive days to define intra-day precision and inter-day precision, respectively. Variation was expressed by the relative standard deviations (RSD)=(standard deviation/mean)×100%. The stability test was performed by analyzing *Dendrobium officinale* water extract sample (HGR-D1) and Chinese medicine formulation samples (TVC-2 and GD) over period of 0, 4, 16, 24, 36, 48 h and measured based on the RSD for the responsive signals. Accuracy was determined from spiking recoveries carried out at the 80%, 100% and 120% levels. Recovery testing was accomplished by adding DOP standard at three different concentration levels (high, middle and low levels) to the HGR-D1, TVC-1 and GD in which the content of DOP was known. Then, the samples were then undergone partial acid hydrolysis and ABEE derivatization. Finally, by determining the oligosaccharide markers, the spiked content of DOP in the sample can be calculated. The spike recovery test was analyzed in triplicates at each level. The spike recoveries were calculated by the following equation: Spike recovery (%)=(total amount of oligosaccharide marker detected−original converted amount of oligosaccharide marker)/converted spiked amount of oligosaccharide marker×100%.

Results

Structural Characteristics of *Dendrobium officinale* Polysaccharides

Figure 2A:
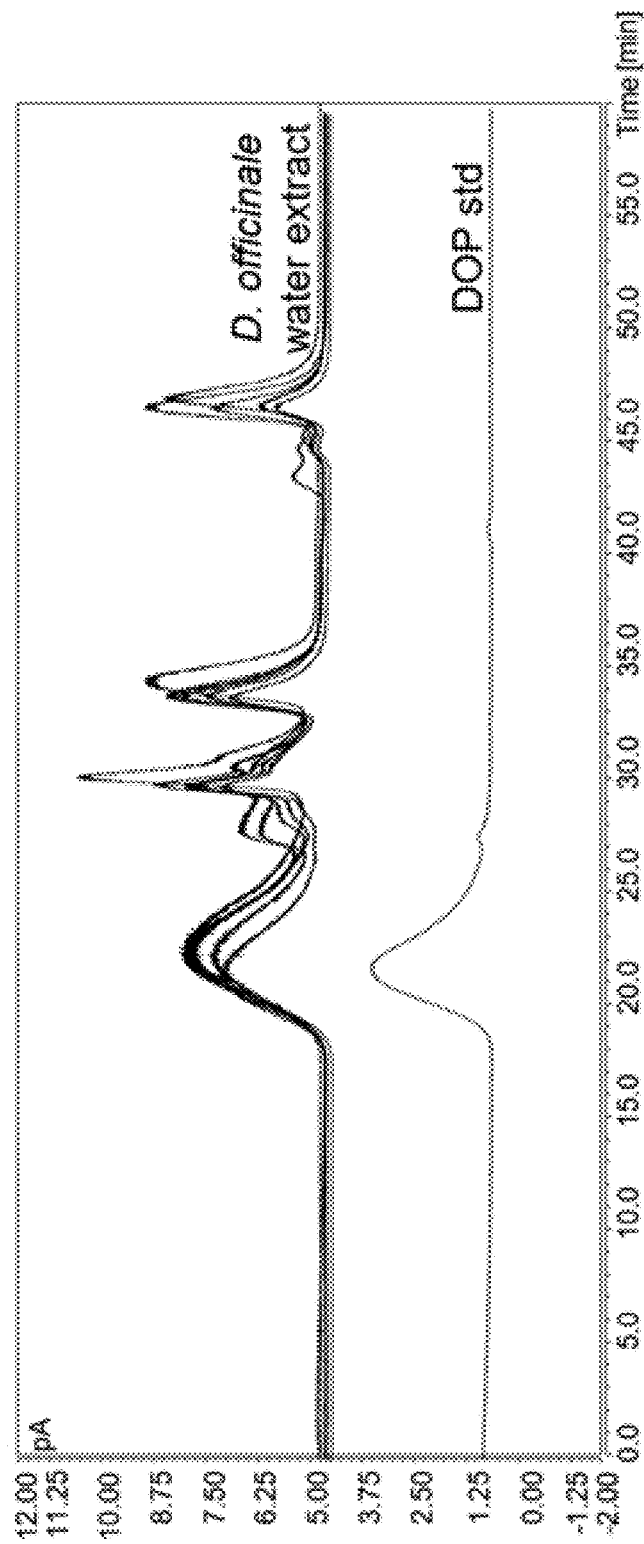
FIG. 2A shows highly consistent HPGPC chromatograms of different batches of *Dendrobium officinale* water extracts and *Dendrobium officinale* polysaccharide standard (DOP std).
Figure 2B:
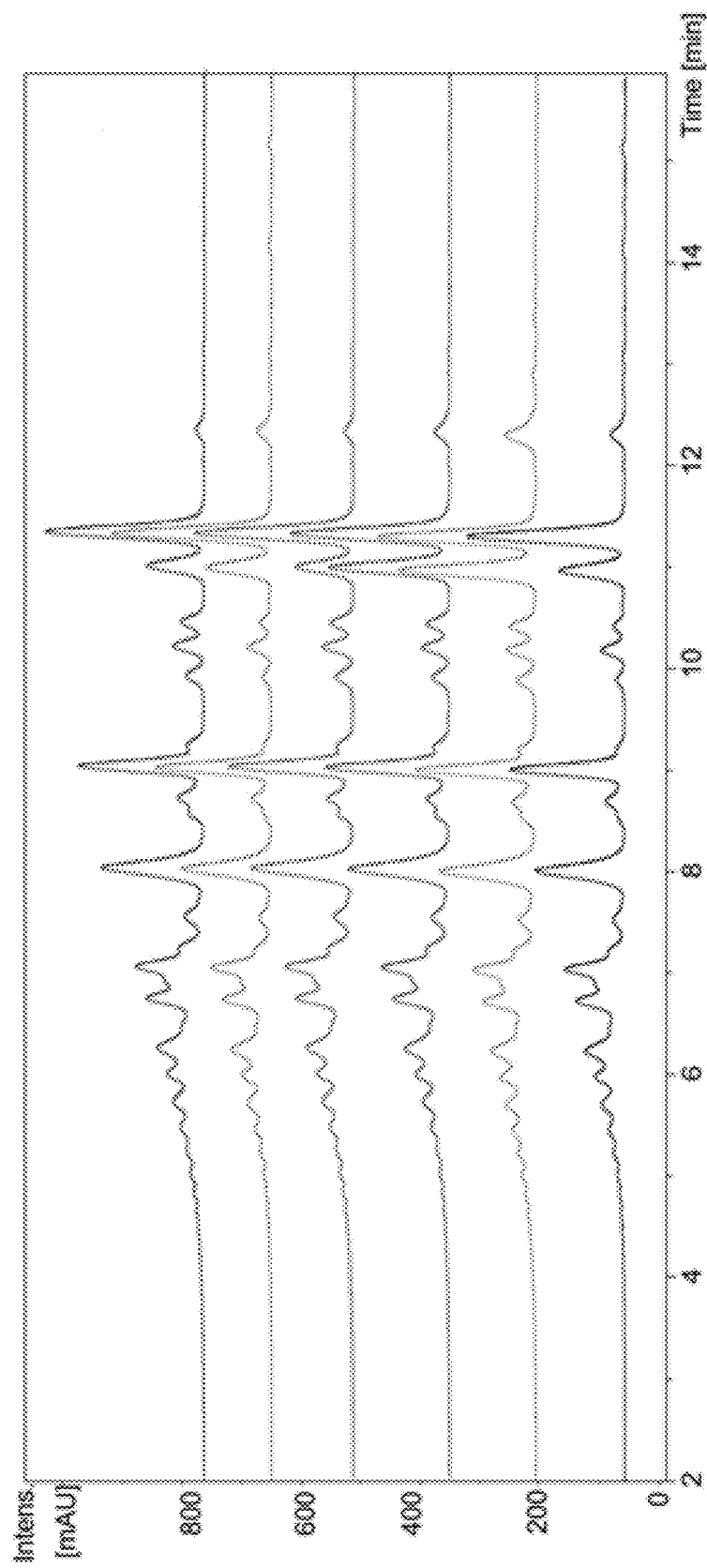
FIG. 2B shows highly consistent UHPLC-qTOF-MS-DAD chromatogram fingerprint of different batches of the *Dendrobium officinale* water extracts after partial acid hydrolysis and ABEE derivatization.

FIG. 1 illustrates the scheme of the utilization of oligosaccharide markers to determine the content of DOP including the preparation of DOP, partial acid hydrolysis, ABEE derivatization, isolation of DOP hydrolysates, establishment of the relation between the content of oligosaccharide markers and the content of DOP in the samples as well as method validation. Regarding the establishment of the relationship between DOP hydrolysates and DOP, the basic structure characterization of DOP in *Dendrobium officinale* water extracts has to be determined first. FIGS. 2A and 2B and Table 1 (FIG. 23) gave out the information with regards to the HPGPC chromatograms of the water extracts, UHPLC-qTOF-MS-DAD chromatograms of DOP hydrolysates, molecular weight and sugar content. As shown in FIGS. 2A and 2B, samples in both HPGPC chromatograms and UHPLC-qTOF-MS-DAD chromatograms were similar which implies that the quality of six batches of authenticated *Dendrobium officinale* samples presented consistently. These two types of chromatograms could be regarded as the fingerprints for qualitative qualification of *Dendrobium officinale* in herbal material water extract and Chinese medicine formulation. According to the results given by HPGPC, six batches of the samples have a dominant peak at retention time about 22.5 min. The weight-average molecular weight was found to be about 770 kDa while the average sugar content was found to be about 72%. For the sake of getting a stable linear relationship between polysaccharide and oligosaccharide markers in quantitative analysis, the parameters including molecular weight and total sugar content were recorded.

Isolation and purification of DOP hydrolysates (HDOP).

Figure 3:
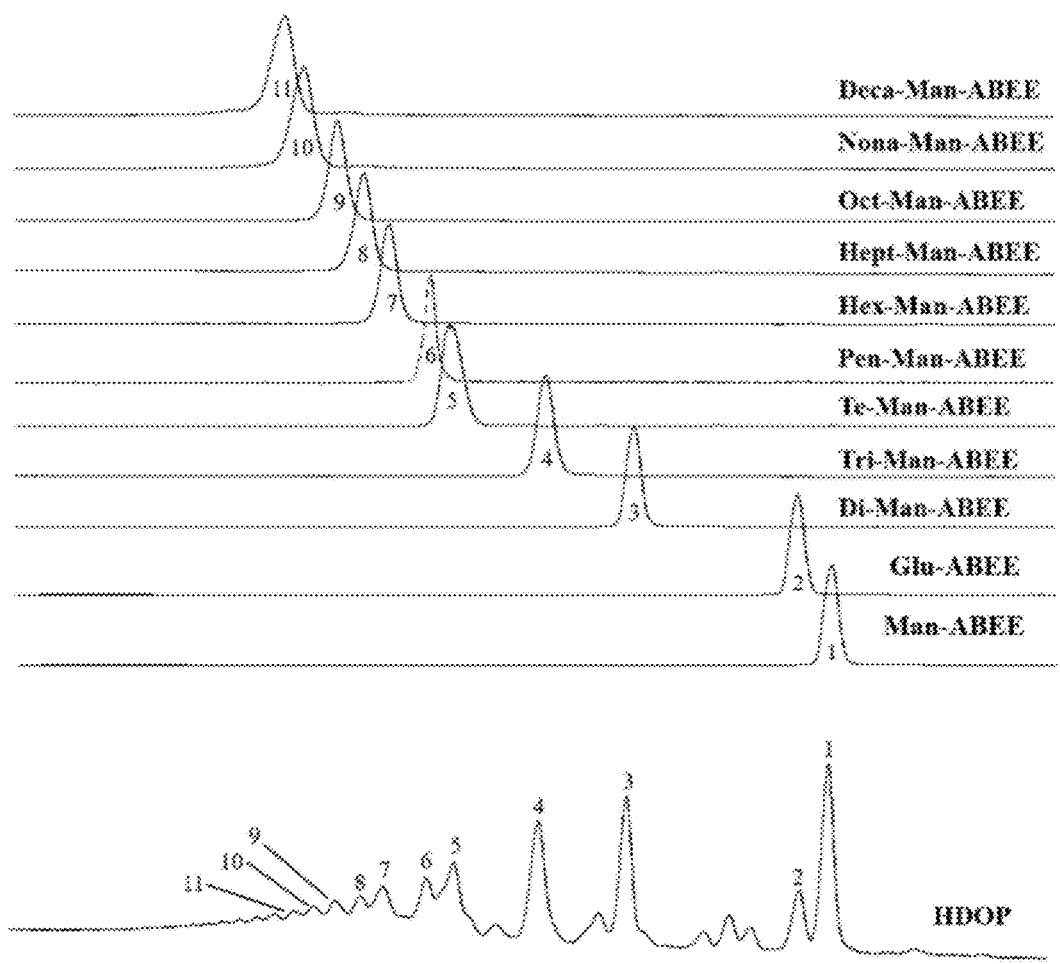
FIG. 3 shows the UHPLC-qTOF-MS-DAD chromatograms of the ABEE-labeled oligosaccharides. 1. Man; 2. Glc; 3. Di-Man-ABEE; 4. Tri-Man-ABEE; 5. Te-Man-ABEE; 6. Pen-Man-ABEE; 7. Hex-Man-ABEE; 8. Hept-Man-ABEE; 9. Oct-Man-ABEE; 10. Nona-Man-ABEE; 11. Deca-Man-ABEE. #Man, Glc, Di, Tri, Te, Pen, Hex, Hept, Oct, Nona and Deca are the abbreviation of mannose, glucose, disaccharide, trisaccharide, tetrasaccharide, pentasaccharide, hexasaccharide, heptasaccharide, octasaccharide, nonasaccharide and decasacchsaride, respectively. HDOP means the hydrolysates produced from partial hydrolysis of *Dendrobium officinalis* polysaccharide.

As for the isolation and purification of HDOP, the addition of ABEE on the reducing end of the oligosaccharides greatly enhanced the separation efficiency, as carbohydrates are lack of UV absorption group. Through the preparative HPLC and HPLC-DAD system, 9 oligosaccharide markers, which were the most abundant oligosaccharide in each DP value, were obtained and shown in FIG. 3, namely Di-Man-ABEE, Tri-Man-ABEE, Te-Man-ABEE, Pen-Man-ABEE, Hex-Man-ABEE, Hept-Man-ABEE, Oct-Man-ABEE, Nona-Man-ABEE and Deca-Man-ABEE with DP value ranging from 2-10.

Sequence Determination of Oligosaccharide Markers

Figure 5:
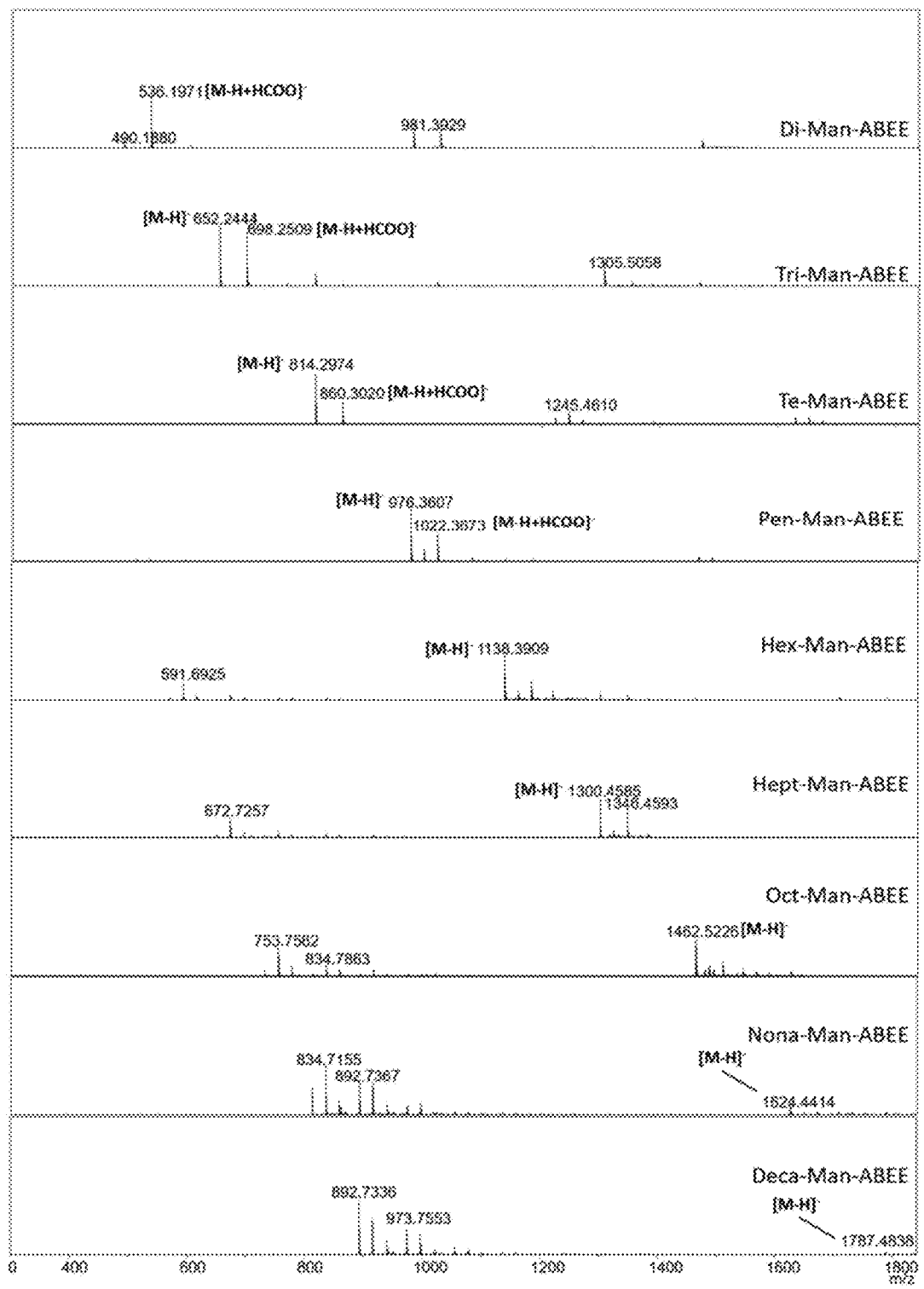
FIG. 5 shows the mass spectra of ABEE-labeled oligosaccharide markers (negative mode). The major signals in each oligosaccharide are labeled as [M–H]— and [M–H+HCO]—, respectively. The MS conditions: nebulizing gas ($N_2$) flow rate, 8.0 L/min; nebulizing gas temperature, 300° C.; capillary, 3500 V; fragmentor voltage, 150 V. Dry temperature was set to 180° C.
Figure 10:
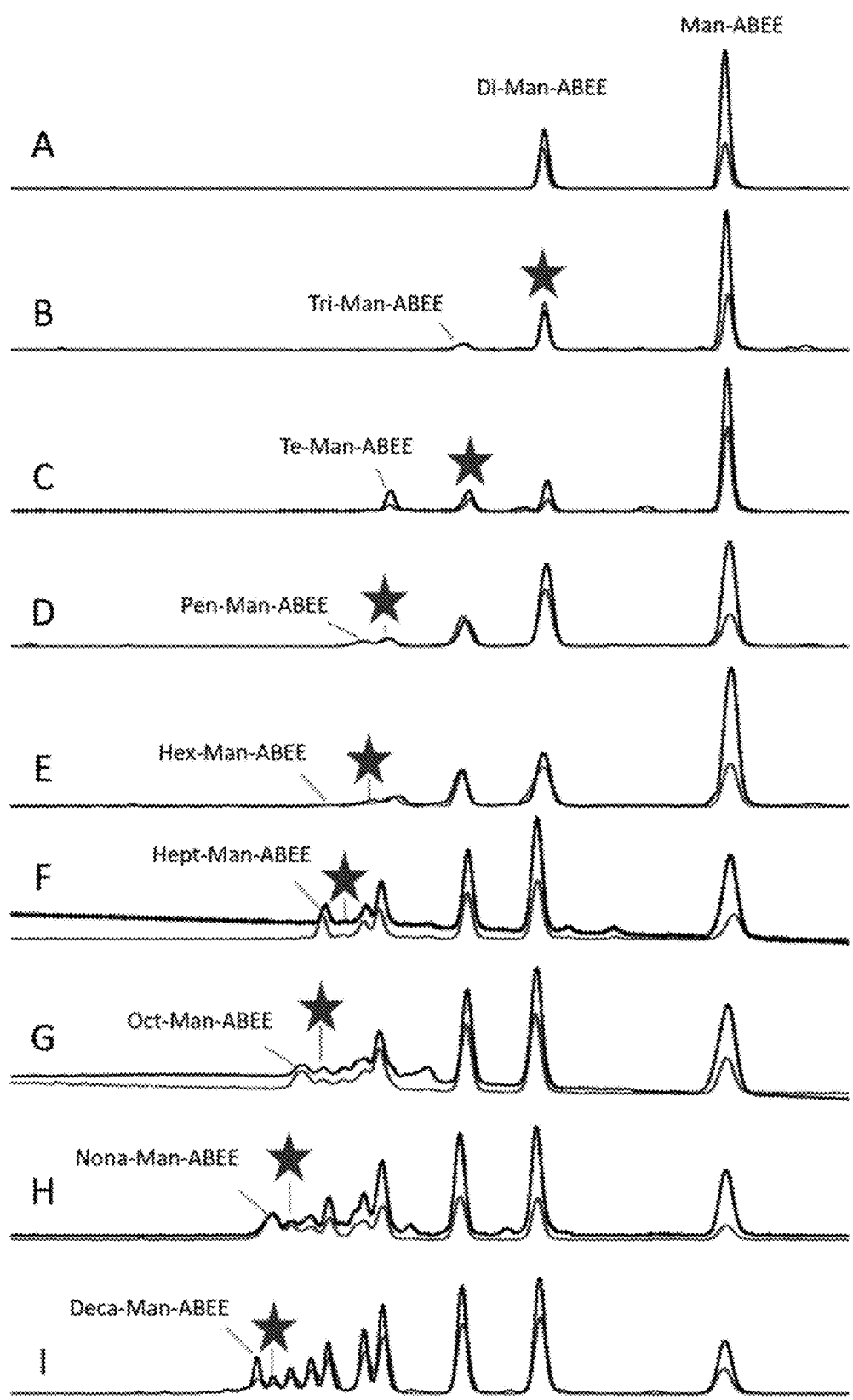
FIG. 10 demonstrates the comparison of hydrolysate profiles of partially hydrolyzed ABEE-labeled oligosaccharide markers before and after relabeling with ABEE. The bottom line shows the profile of each partially hydrolyzed ABEE-labeled oligosaccharide markers; and the upper line presents the result of subsequent ABEE re-labeling after partial hydrolysis. A: Di-Man-ABEE, B: Tri-Man-ABEE, C: Te-Man-ABEE, D: Pen-Man-ABEE, E: Hex-Man-ABEE, F: Hept-Man ABEE, G: Oct-Man-ABEE, H: Nona-Man-ABEE, I: Deca-Man-ABEE. For example, in case of I: Deca-Man-ABEE, significant increase in the intensity of several hydrolysate after relabeling was observed which suggested that partial hydrolysis of Deca-Man-ABEE contains these fragments. Especially, the production of Nona-Man-ABEE (highlighted with star) indicated that the mother sample at least contained the fragment of Nona-Man.

The sequence of each of the oligosaccharide markers was determined by partial acid hydrolysis and re-derivatization using the established UHPLC-qTOF-MS method. The typical chromatograms of each of the markers and their respective MS spectrum are summarized in FIGS. 5 and 10. The number of saccharide units contained in the oligosaccharide marker and the corresponding sequence in each oligosaccharide marker can be determined by the comparison of hydrolysate profiles of partially hydrolyzed ABEE-labeled oligosaccharide markers before and after relabeling with ABEE. According to FIG. 10, Di-Man-ABEE contains Man-ABEE and Di-Man-ABEE peaks in both partially hydrolyzed and re-labeled chromatograms. The presence of Man-ABEE peak indicates that the reducing end of Di-Man-ABEE is mannose. Moreover, the significant increase in the intensity of Man-ABEE after relabeling suggested that Di-Man-ABEE contains only mannose residues. Accordingly, Tri-Man-ABEE contains peaks of Di-Man-ABEE and Man-ABEE in both partially hydrolyzed and re-labeled chromatograms. The significant increase in the intensity of the two peaks after relabeling suggested that partial hydrolysis of Tri-Man-ABEE contains these fragments. Thus, these fragments should be part of the sequence of Tri-Man-ABEE.

Accordingly, Te-Man-ABEE composes of 4 mannose residues; Pen-Man-ABEE composes of 5 mannose residues; Hex-Man-ABEE composes of 6 mannose residues; Hept-Man-ABEE composes of 7 mannose residues; Oct-Man-ABEE composes of 8 mannose residues, Nona-Man-ABEE composes of 9 mannose residues; Deca-Man-ABEE composes of 10 mannose residues.

Methylation Reaction and GC-MS Analysis

Since the UHPLC-qTOF-MS spectrum can only provide data relating to the composition of the saccharide units and sequence, there is no information regarding the glycosidic linage. Therefore, methylation reaction was performed. From the results, there were mainly two peaks that appeared in the GC-MS spectrum. The peak at the retention time 14.6 min is the signal of 2,3,4,6-Me$_4$-Manp that represents the presence of terminal mannopyranosyl residues. On the other hand, the peak at the retention time 18.3 min is the signal of 2,3,6-Me$_3$-Manp which represents the presence of 1,4-linked-mannopyranosyl residue. To sum up, all the markers contain these two obvious peaks, but have a higher intensity of the peak at 18.3 min due to the higher concentration 1,4-linked-mannopyranosyl residues. Thus, it can be concluded that the glycosidic linkage in all the markers is β-1-4 linked D-mannopyranosyl residues. According to Table 2 (FIG. 24), the monosaccharide composition of all the oligosaccharides was dominant in mannose while the methylation GC-MS analysis showed that all the oligosaccharide markers were mainly in 1,4-linked mannosylpyranose. Therefore, it can be confirmed that all the oligosaccharide markers are β 1-4 linked D-mannopyranose with different in the degree of polymerization.

NMR Spectroscopy

Figure 4:
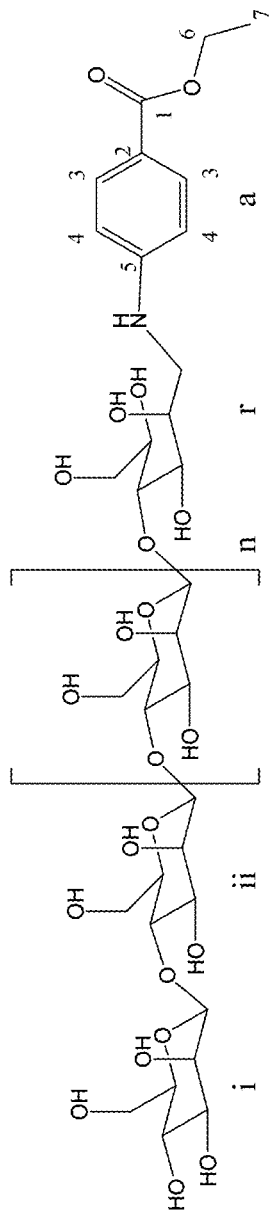
FIG. 4 shows the proposed chemical structure of ABEE-labeled oligosaccharide markers. i stands for the terminal end, ii stands for the saccharide residue that linked to the terminal end while r stands for the reducing end which linked to ABEE (a), i.e., Te-Man-ABEE, n=1; Pen-Man-ABEE, n=2; Hex-Man-ABEE, n=3; Hept-Man-ABEE, n=4; Oct-Man-ABEE, n=5; Nona-Man-ABEE, n=6; Deca-Man-ABEE, n=7.
Figure 6:
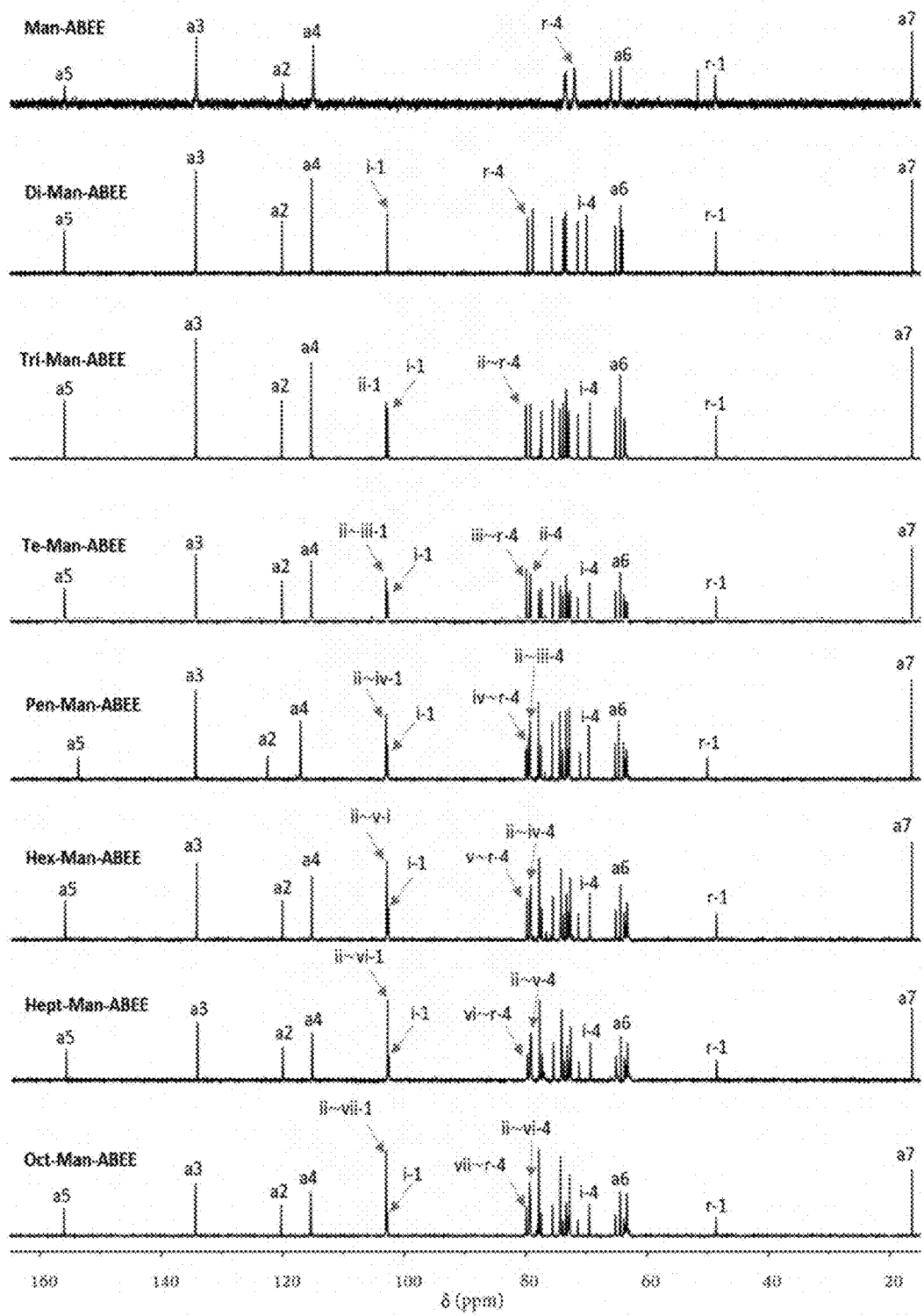
FIG. 6 shows the $^{13}C$ NMR spectra of ABEE-labeled oligosaccharide makers (100 MHz, in $D_2O$). Tetramethylsilane (TMS) was used as the internal reference.
Figure 7:
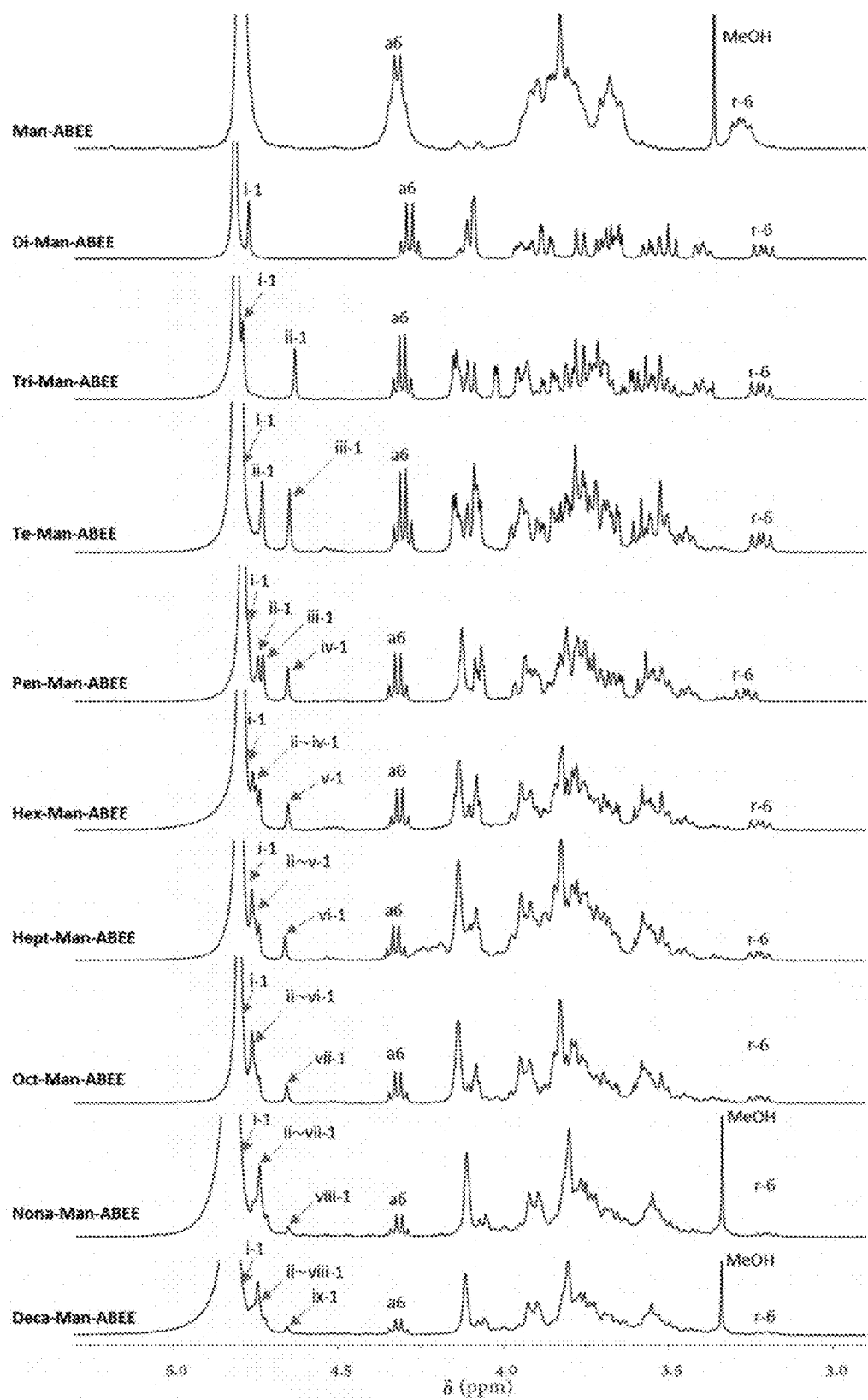
FIG. 7 shows the $^1H$ NMR spectra of ABEE-labeled oligosaccharide makers (400 MHz, in $D_2O$). TMS was used as the internal reference.
Figure 8A:
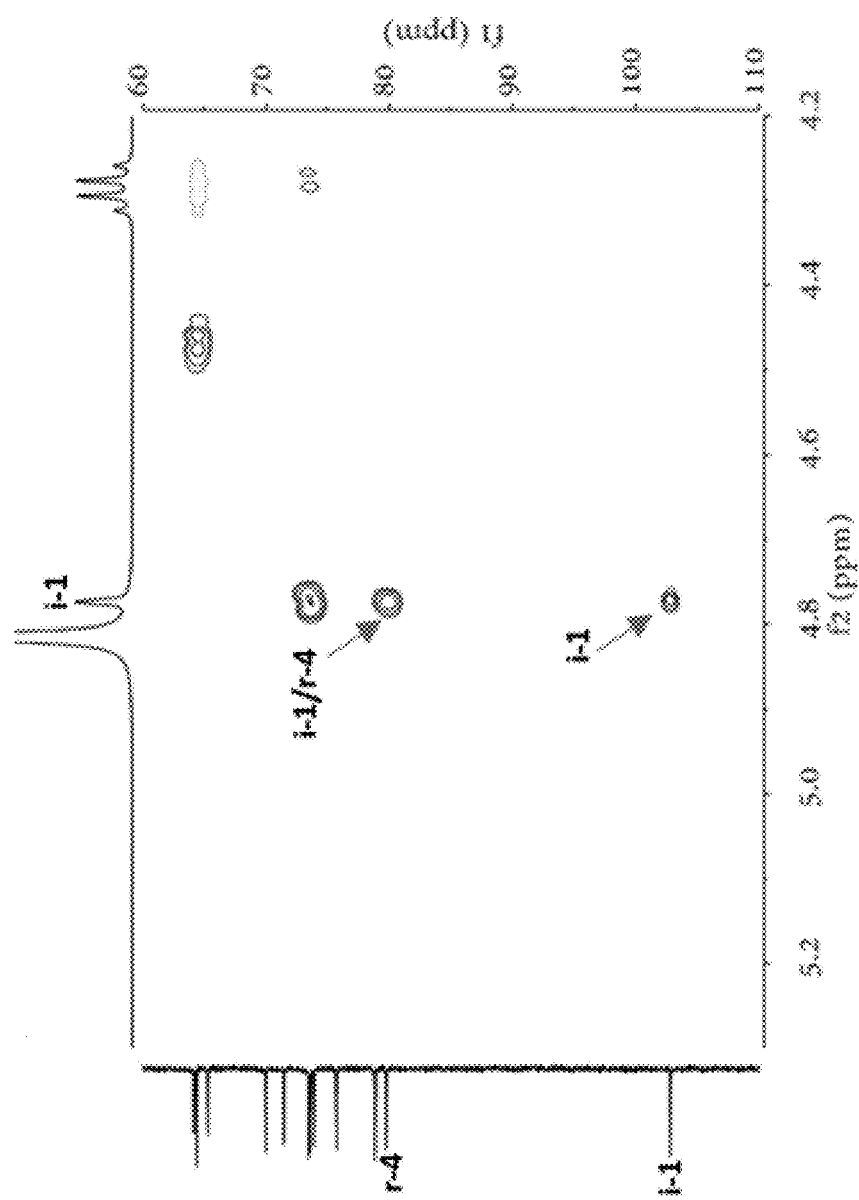
FIG. 8A shows heteronuclear single quantum coherence (HSQC) and heteronuclear multiple bond correlation (HMBC) spectra of ABEE-labeled, Di-Man-ABEE. The example indication i-1/ii-4 showed HMBC correlation between proton i-1 and carbon ii-4.
Figure 8B:
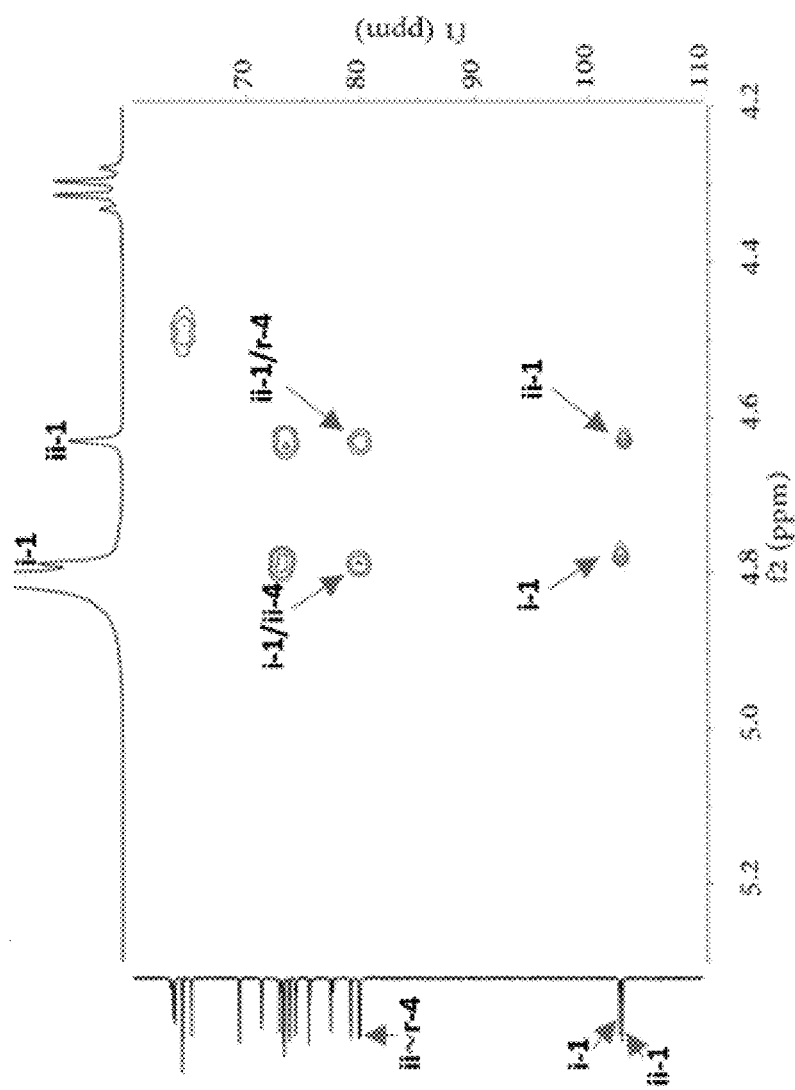
FIG. 8B shows HSQC and HMBC spectra of ABEE-labeled, Tri-Man-ABEE. The example indication i-1/ii-4 showed HMBC correlation between proton i-1 and carbon ii-4.
Figure 8C:
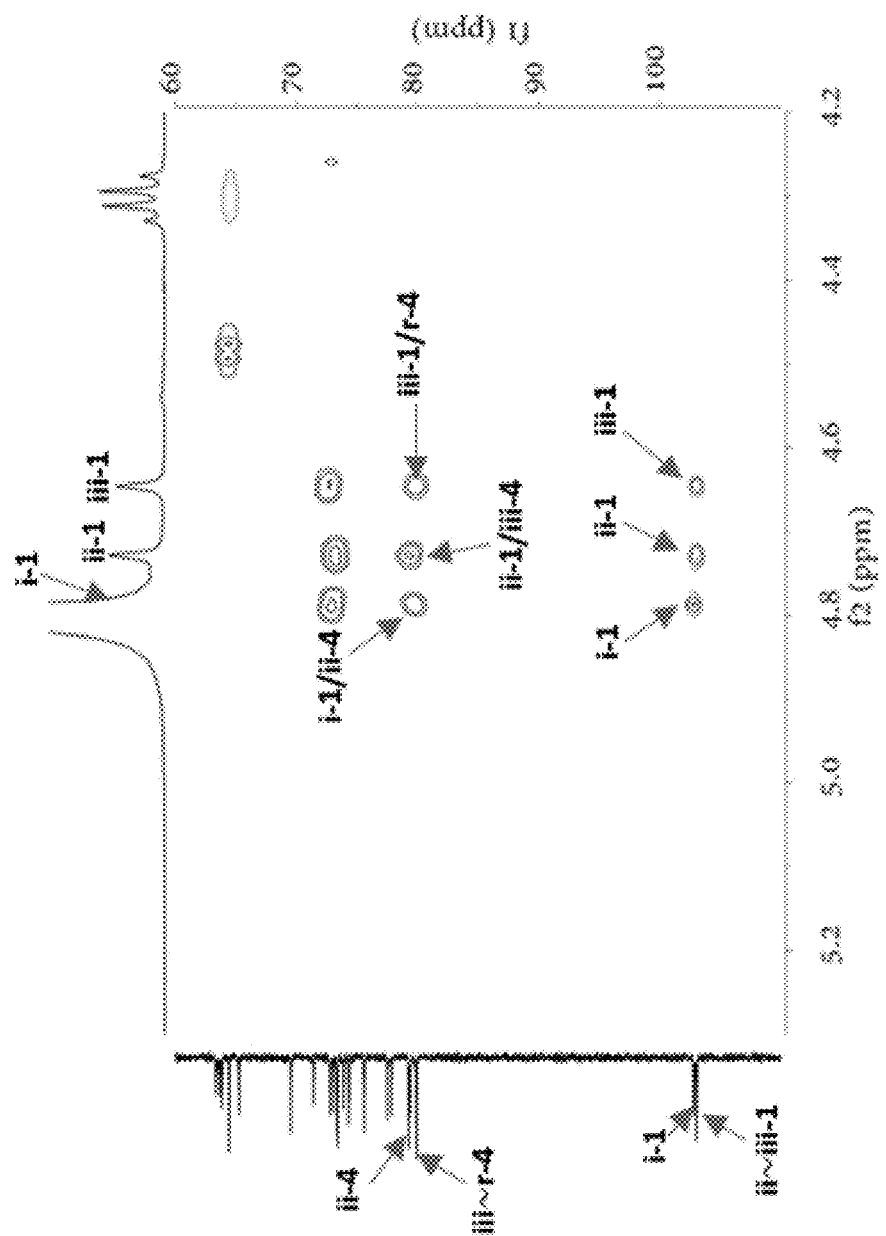
FIG. 8C shows HSQC and HMBC spectra of ABEE-labeled, Te-Man-ABEE. The example indication i-1/ii-4 showed HMBC correlation between proton i-1 and carbon ii-4.
Figure 8D:
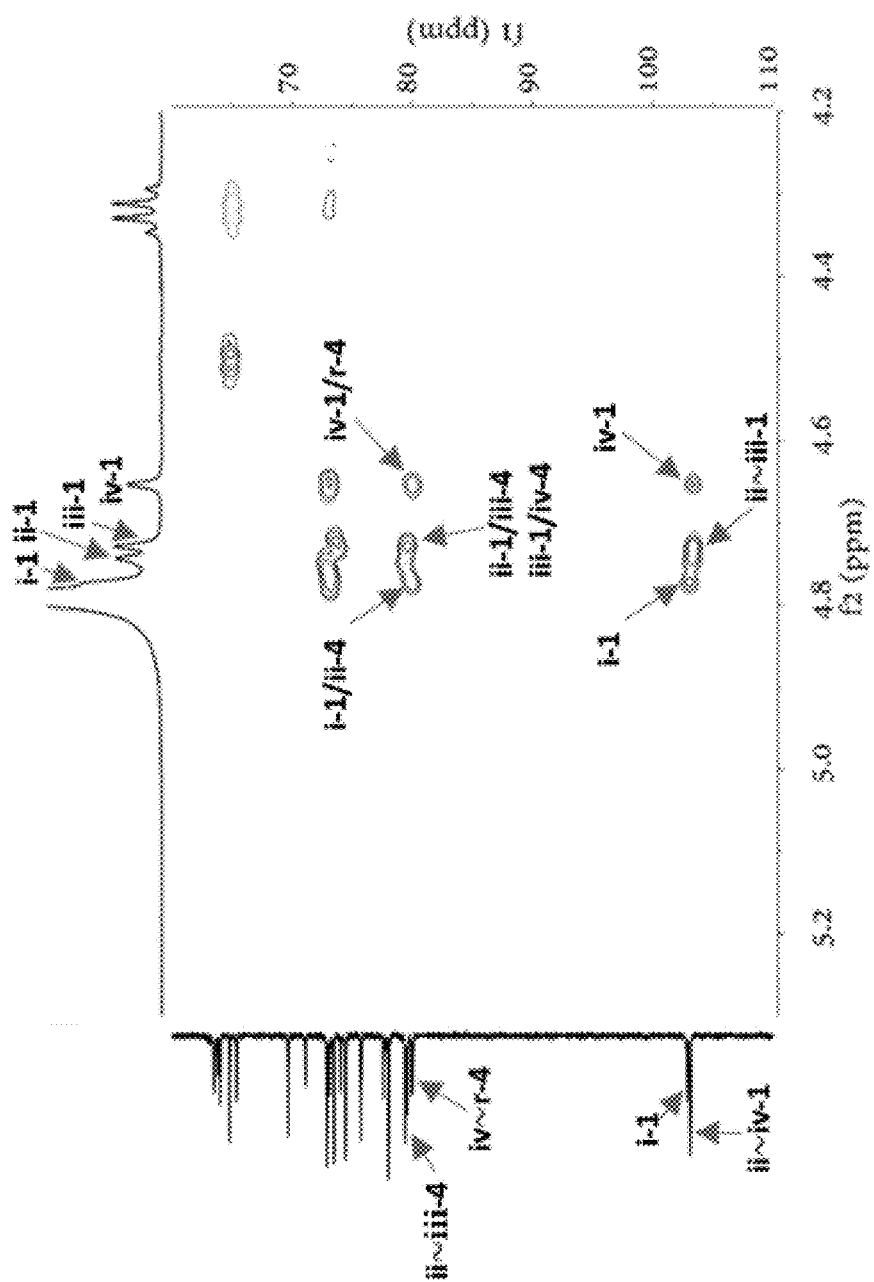
FIG. 8D shows HSQC and HMBC spectra of ABEE-labeled, Pen-Man-ABEE. The example indication i-1/ii-4 showed HMBC correlation between proton i-1 and carbon ii-4.
Figure 8E:
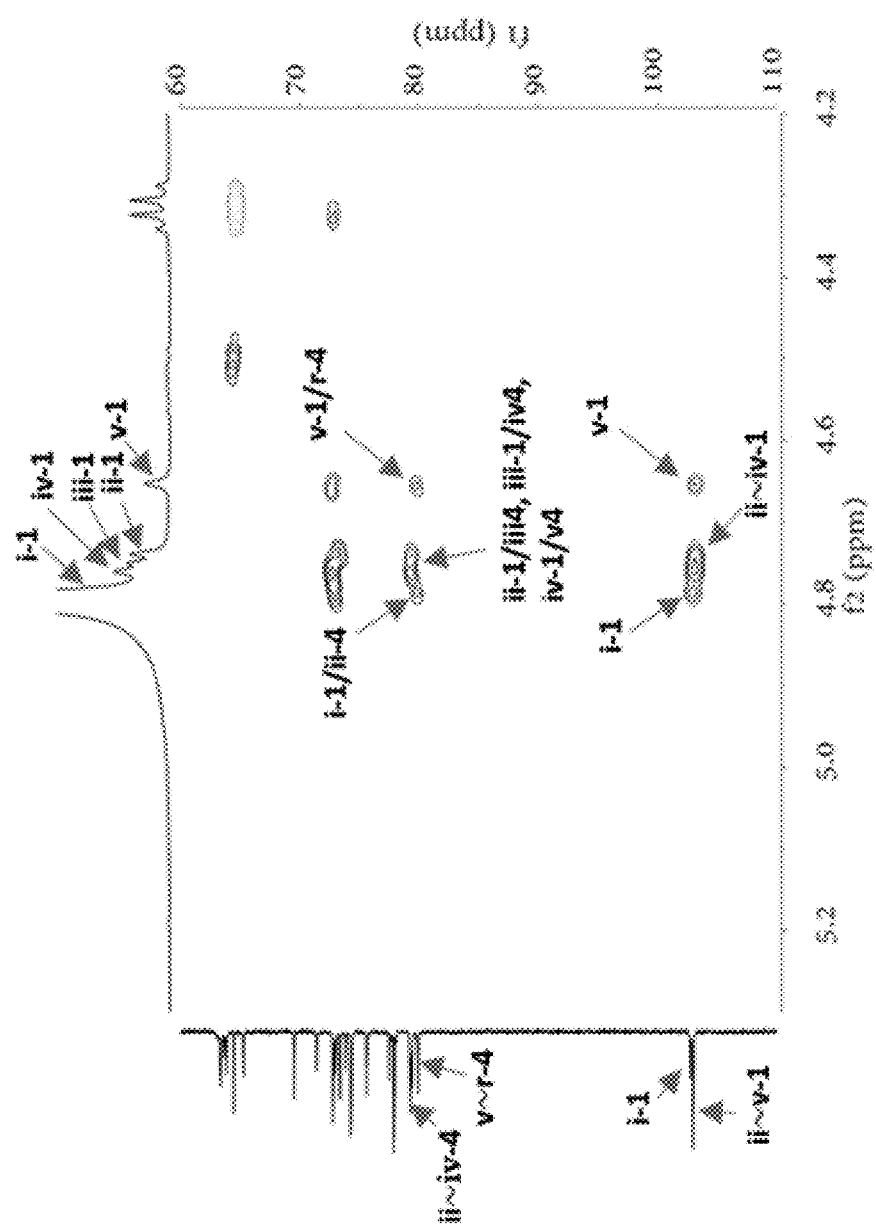
FIG. 8E shows HSQC and HMBC spectra of ABEE-labeled, Hex-Man-ABEE. The example indication i-1/ii-4 showed HMBC correlation between proton i-1 and carbon ii-4.
Figure 8F:
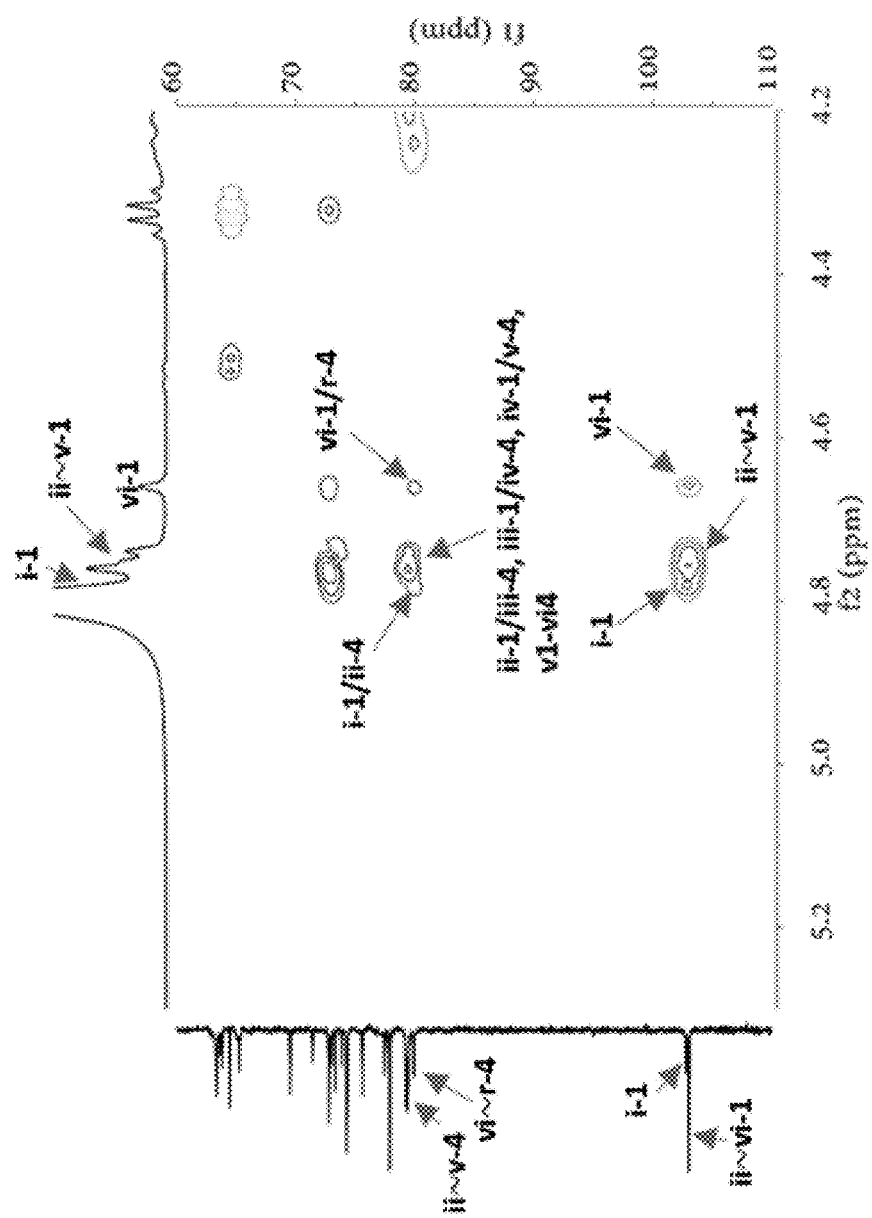
FIG. 8F shows HSQC and HMBC spectra of ABEE-labeled, Hept-Man-ABEE. The example indication i-1/ii-4 showed HMBC correlation between proton i-1 and carbon ii-4.
Figure 8G:
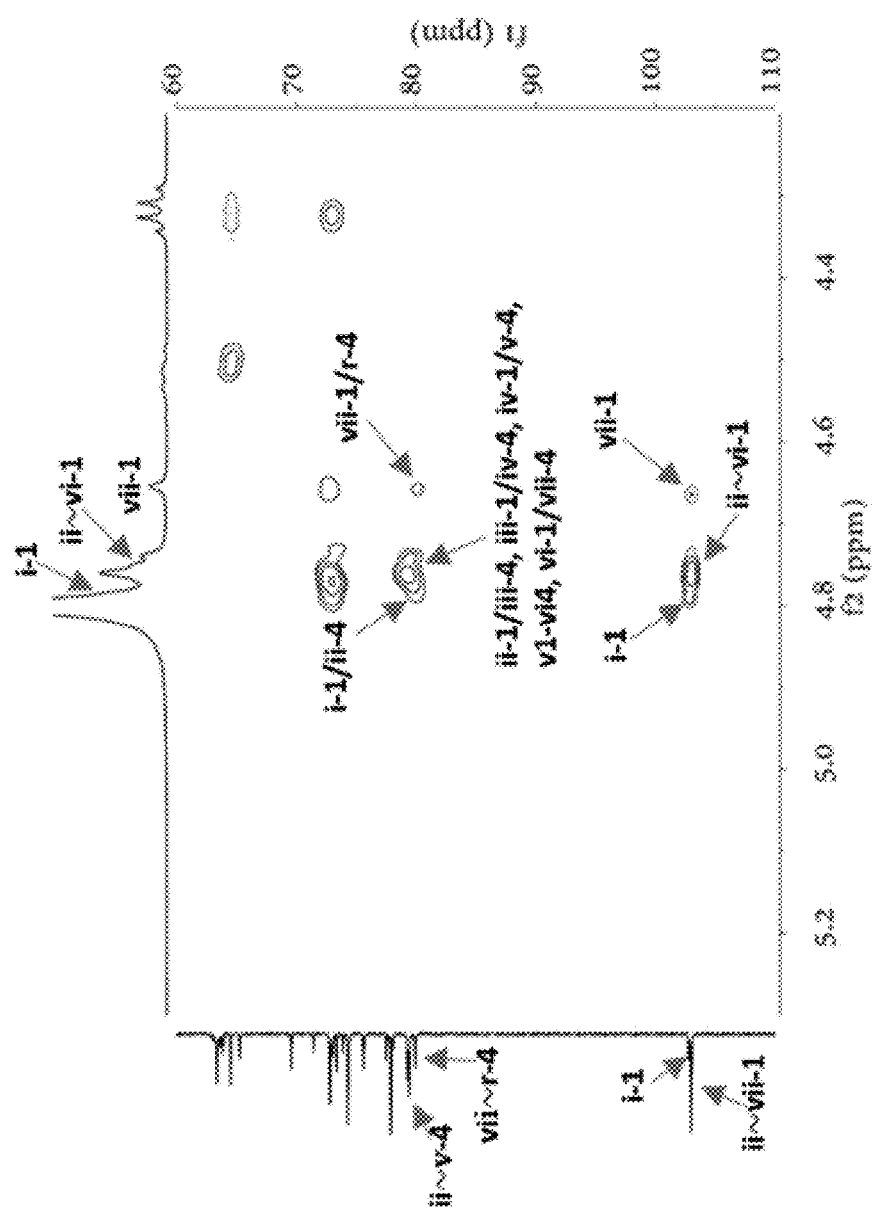
FIG. 8G shows HSQC and HMBC spectra of ABEE-labeled, Oct-Man-ABEE. The example indication i-1/ii-4 showed HMBC correlation between proton i-1 and carbon ii-4.
Figure 9A:
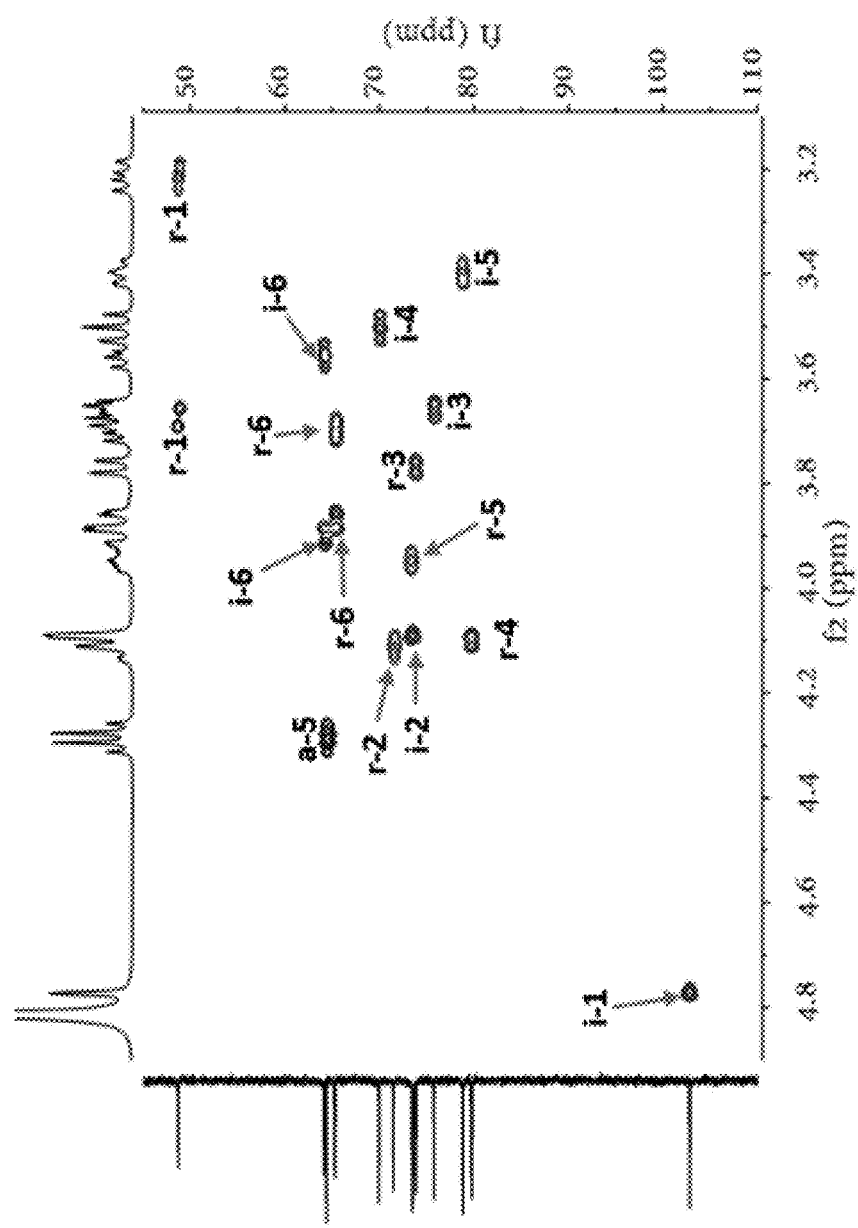
FIG. 9A illustrates HSQC spectra of ABEE-labeled oligosaccharide marker, Di-Man-ABEE.
Figure 9B:
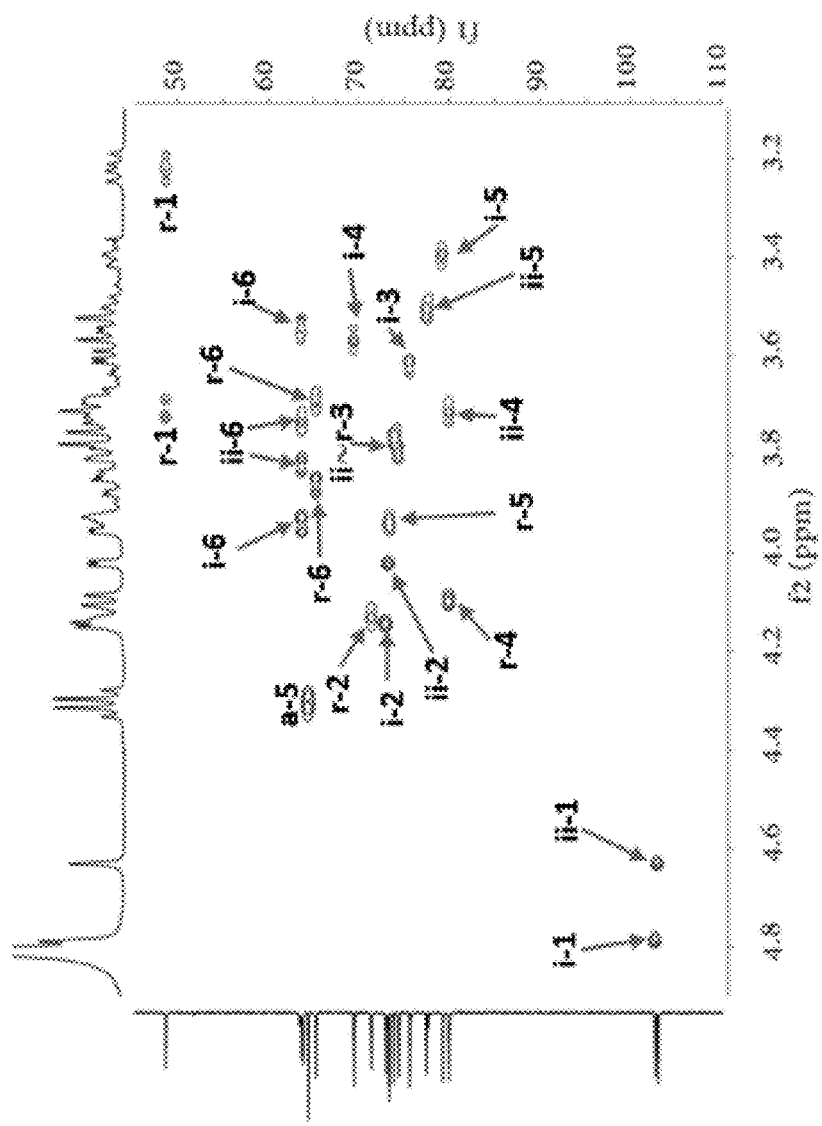
FIG. 9B illustrates HSQC spectra of ABEE-labeled oligosaccharide marker, Tri-Man-ABEE.
Figure 9C:
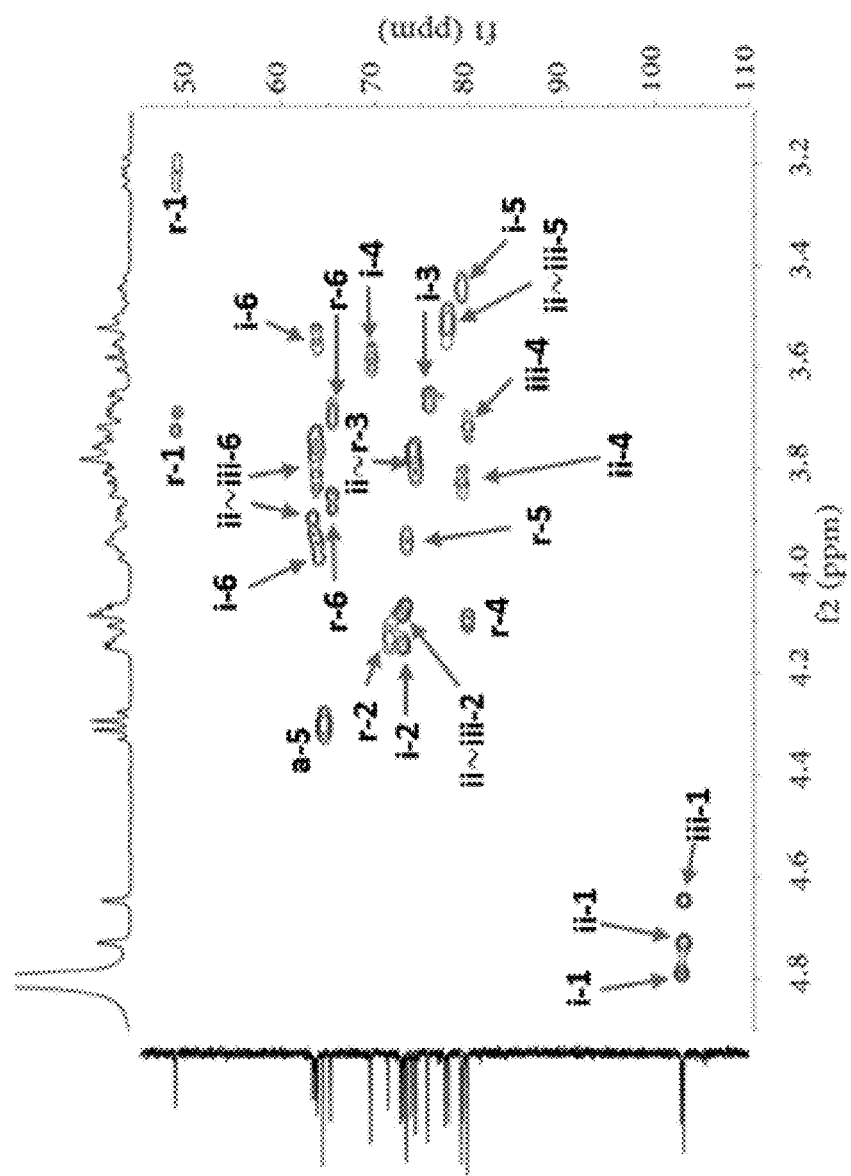
FIG. 9C illustrates HSQC spectra of ABEE-labeled oligosaccharide marker, Te-Man-ABEE.
Figure 9D:
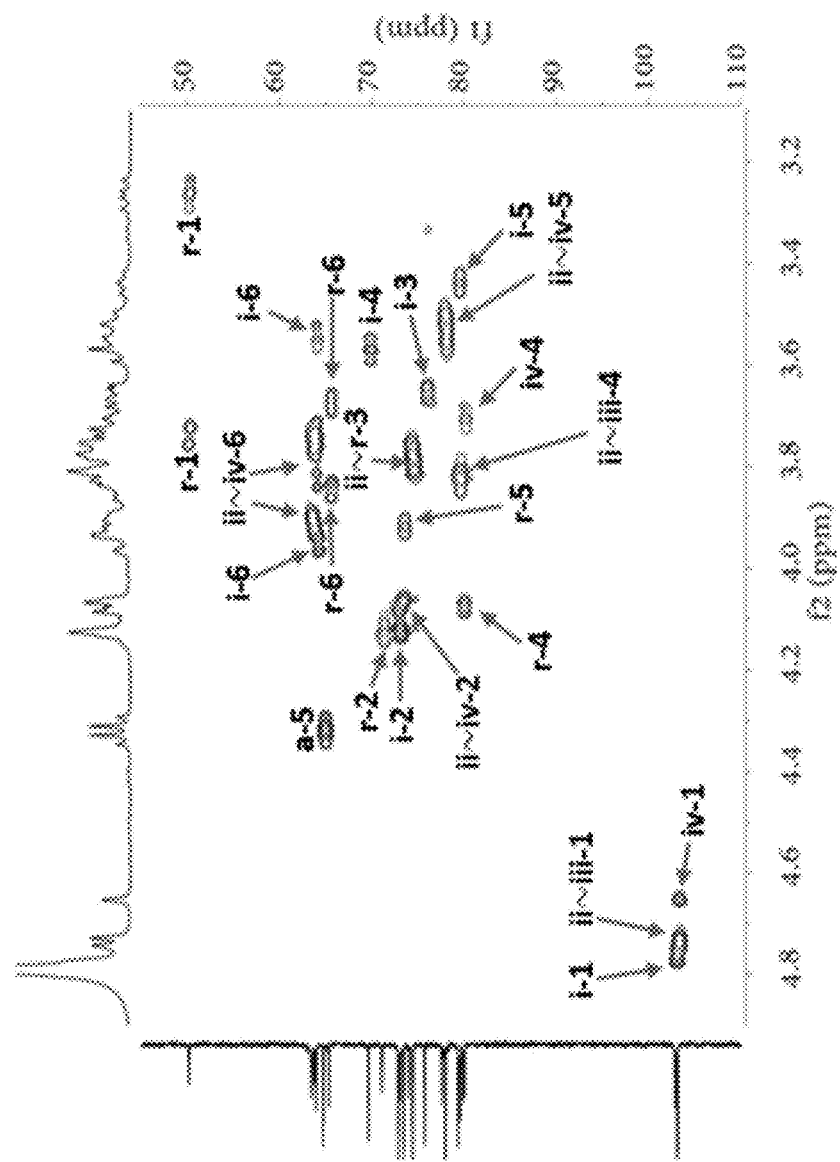
FIG. 9D illustrates HSQC spectra of ABEE-labeled oligosaccharide marker, Pen-Man-ABEE.
Figure 9E:
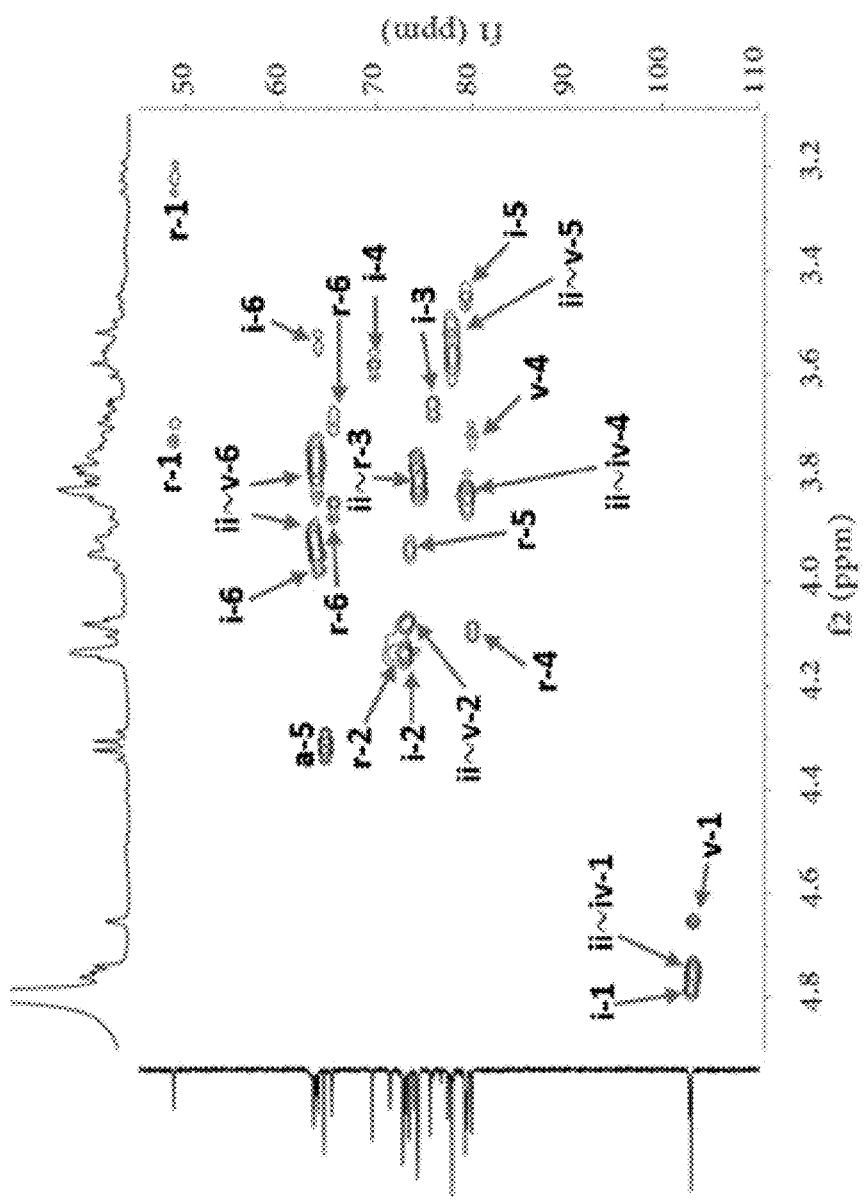
FIG. 9E illustrates HSQC spectra of ABEE-labeled oligosaccharide marker, Hex-Man-ABEE.
Figure 9F:
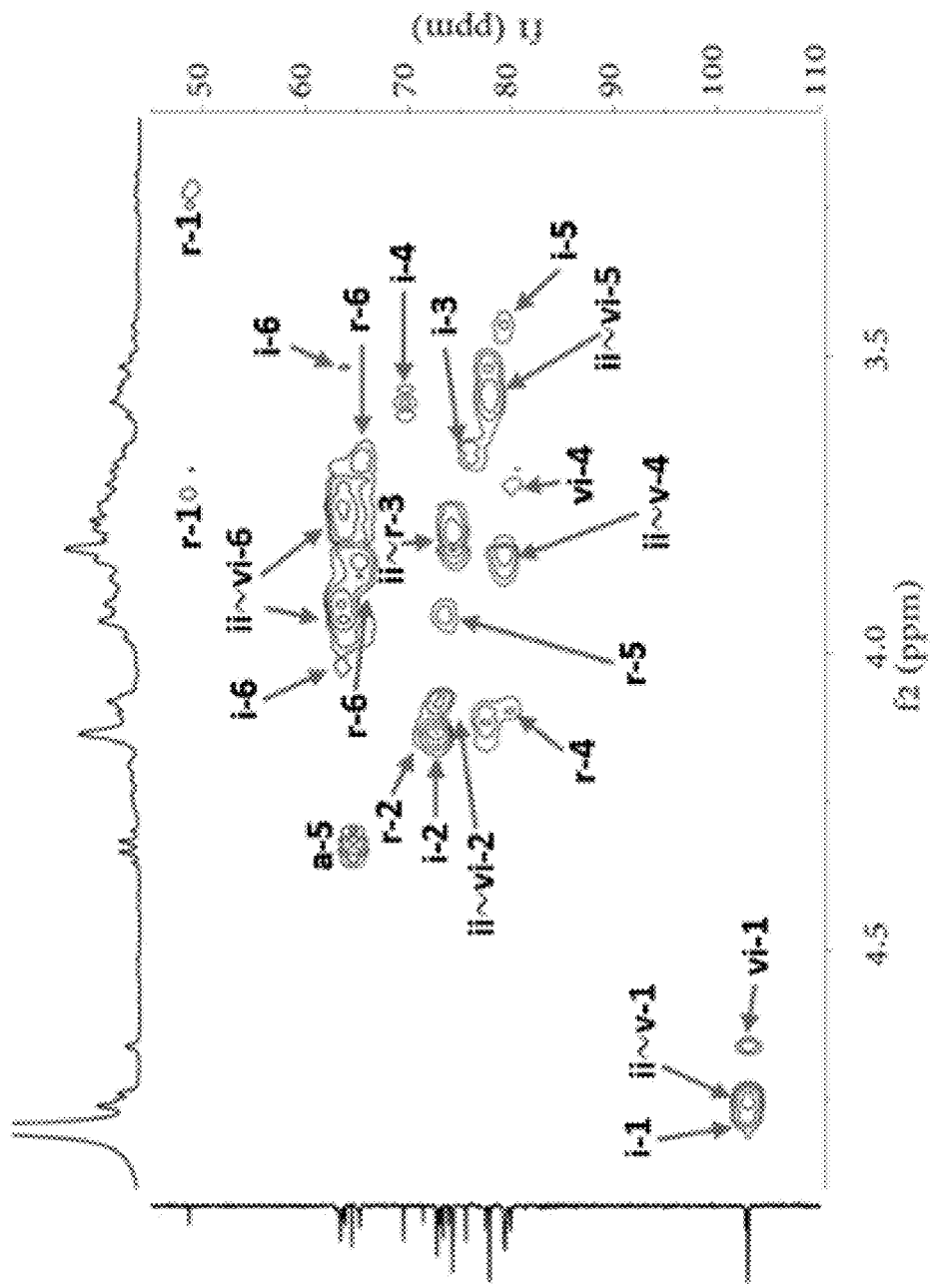
FIG. 9F illustrates HSQC spectra of ABEE-labeled oligosaccharide marker, Hept-Man-ABEE.
Figure 9G:
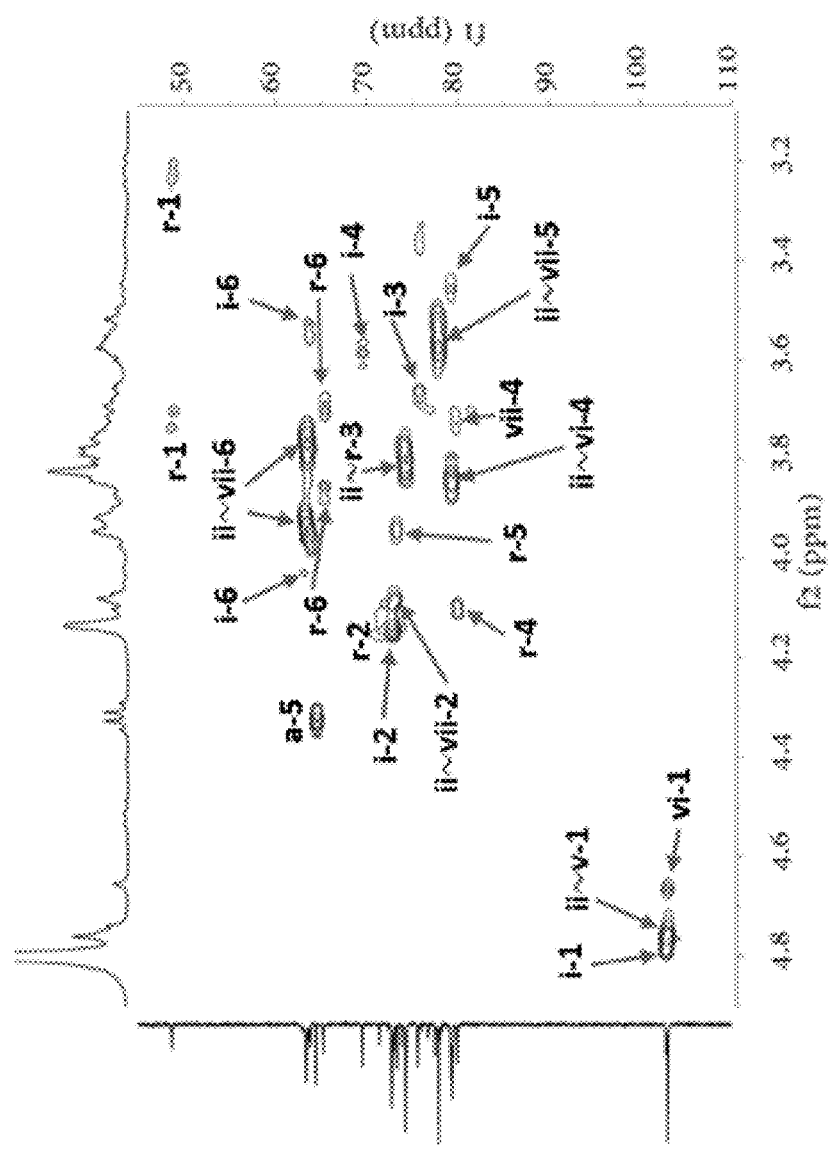
FIG. 9G illustrates HSQC spectra of ABEE-labeled oligosaccharide marker, Oct-Man-ABEE.

Although UHPLC-qTOF-MS and methylation reaction nearly determine the structure of all the markers, NMR spectroscopy is important to give evidences for the prove of the interpretation of these two analytical methods. FIGS. 6 and 7 illustrated the $^{13}$C NMR and $^1$H NMR of all the markers which implied the anomeric regions of 4.5-5.0 ppm in 1H NMR spectra and 95-105 ppm in 13C NMR spectra. Since the markers is derivatized by ABEE upon reductive amination at C-1 of the reducing end, ABEE-derivatization of authentic D-mannose and D-glucose were assigned first in order to facilitate the assignment of the signals of the isolated markers. From the results, the C-1 signals was shifted to the upfield substantially (δ48.8) upon amination, compared with the C-1 signals of free β-D-mannose, while the signal of C-6 was nearly unchanged (δ63.8 for labeled, δ66.1 for labeled). For the sake of exemplifying how β(1-4)-linked Man residues are identified, HSQC and HMBC spectra of the oligosaccharide markers were overlaid and shown in FIG. 8A-8G. For example, the H1C1 signals of r-Man in the Te-Man-ABEE was shifted to the upfield (δ48.8 ppm) upon amination while H1C1 of i-Man, ii-Man and iii-Man showed up at δ4.79/102.82 ppm, δ4.73/103.05 ppm, δ4.64/103.03 ppm. In addition, the chemical shift of the C-4 signals in ii-Man, iii-Man and r-Man were observed to be remarkably downfield (~δ79.7 ppm) compared to the C-4 signal in D-mannose (δ69.45 ppm) and Man-ABEE (δ72.01 ppm). The 2-D HMBC spectra also indicated the correlations between H1C4 resonance of i-Man/ii-Man, ii-Man/iii-Man and iii-Man/r-Man. All the results gave out the conclusion that Te-Man-ABEE is a 1,4-linked β-D-tetra-oligosaccharide. Compared to the results of Te-Man-ABEE, H1C1 of ii-Man in Pen-Man-ABEE showed up at δ4.74/103.34 ppm which was close to the other mannose residues. This implied that the additional saccharide residue in Pen-Man-ABEE was D-mannose. The 2-D HMBC spectra of Pen-Man-ABEE also indicated the correlations between H1C4 resonance of i-Man/ii-Man, ii-Man/iii-Man, iii-Man/iv-Man and iv-Man/r-Man. All the results gave out the conclusion that Pen-Man-ABEE is a 1,4-linked β-D-penta-mannooligosaccharide. As for the resonance of the protons in carbons in saccharide residues of all ABEE-labeled oligosaccharides, they were shown in FIG. 9A-9G while the corresponding summarized in Table 3 (FIG. 25). The proposed structures of the oligosaccharide markers can be referred to FIG. 4

UHPLC-qTOF-MS Quantitative Method Validation

Figure 11A:
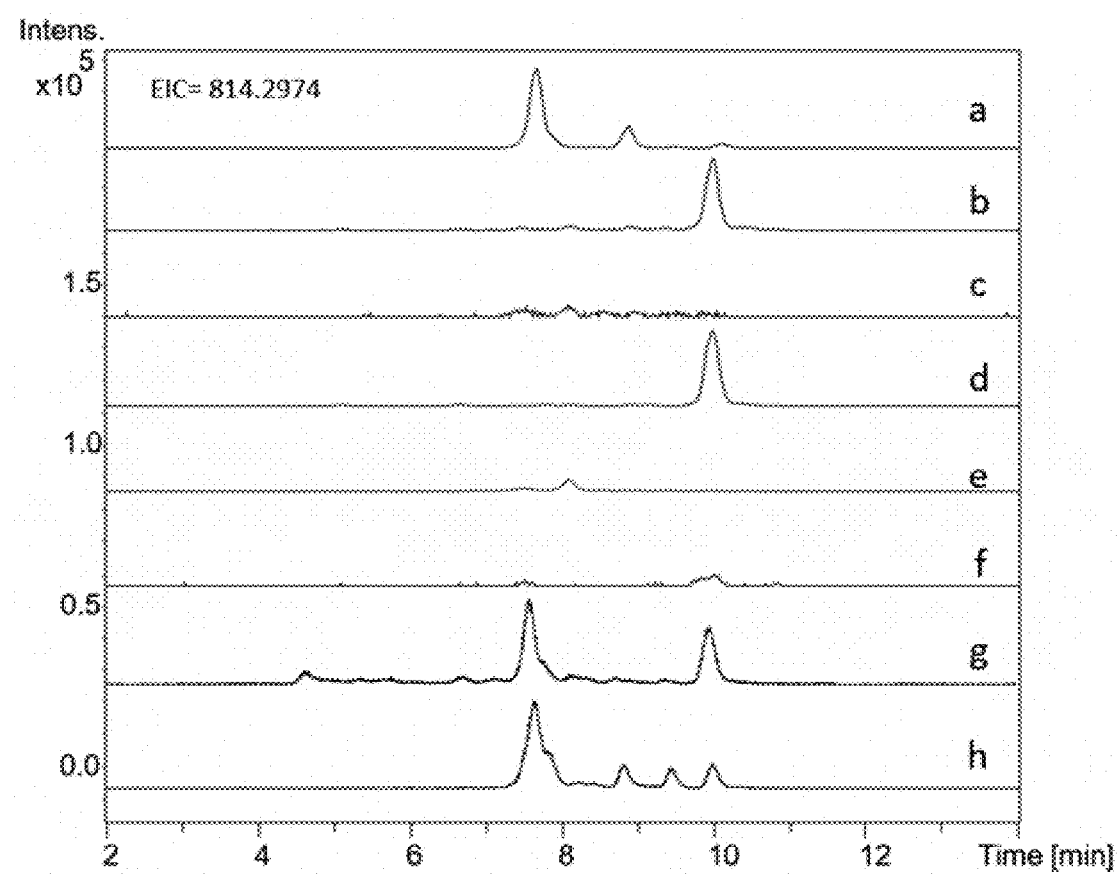
FIG. 11A illustrates the comparison of hydrolysate profiles of partially hydrolyzed herbal ingredients water extract, (a): *Dendrobium officinale*; (b): Panacis Quinquefolii Radix; (c): Ophiopogonis Radix; (d): Coicis Semen; (e): Polygonati Rhizoma; (f): Phragmitis Rhizoma in (g) Tonic Vitality Confection and (a): *Dendrobium officinale*; (b): Panacis Quinquefolii Radix in (h) Granule Dendrobii by UHPLC-qTOF-MS. The extraction ion chromatograms (EIC) of ABEE-labeled oligosaccharide marker Te-Man-ABEE at m/z: 814.2974.
Figure 11B:
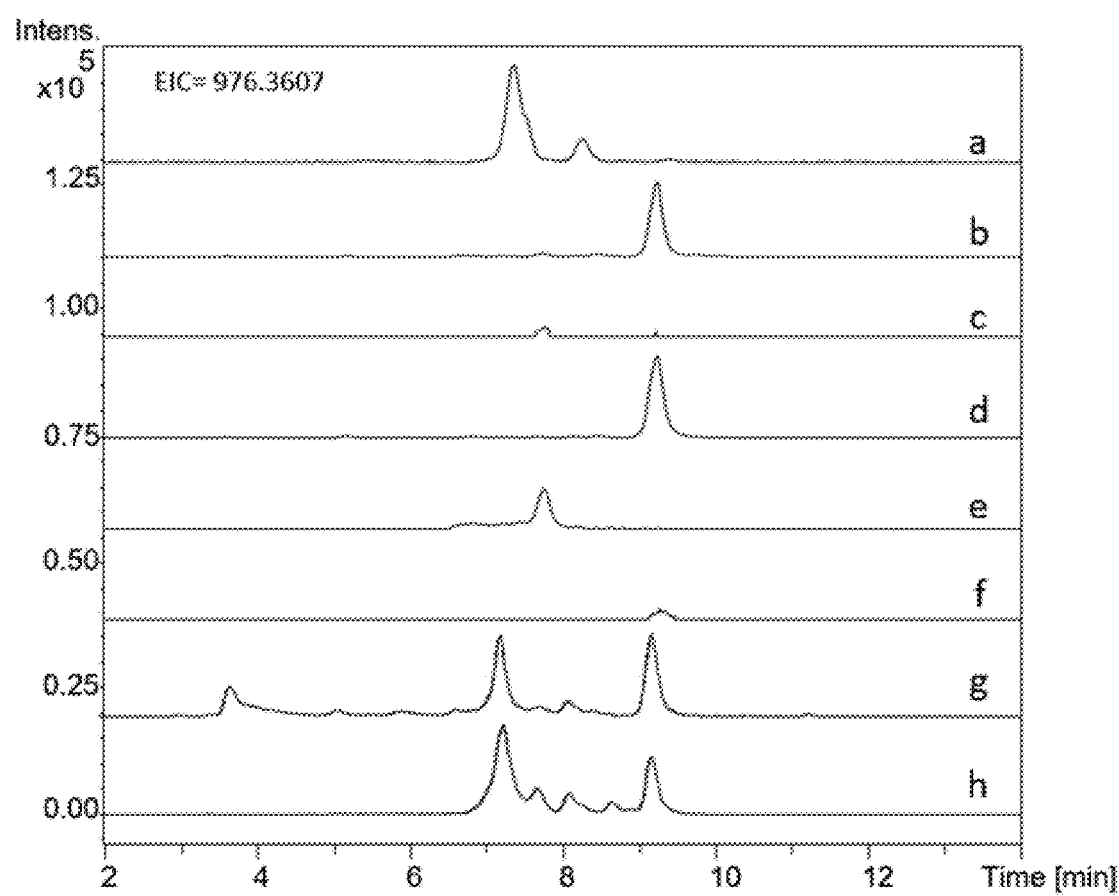
FIG. 11B illustrates the comparison of hydrolysate profiles of partially hydrolyzed herbal ingredients water extract, (a): *Dendrobium officinale*; (b): Panacis Quinquefolii Radix; (c): Ophiopogonis Radix; (d): Coicis Semen; (e): Polygonati Rhizoma; (f): Phragmitis Rhizoma in (g) Tonic Vitality Confection and (a): *Dendrobium officinale*; (b): Panacis Quinquefolii Radix in (h) Granule Dendrobii by UHPLC-qTOF-MS. The extraction ion chromatograms (EIC) of ABEE-labeled oligosaccharide marker Pen-Man-ABEE at m/z: 976.3607.

Since the second objective of this invention is to use the detected content of the isolated oligosaccharide markers to calculate the original content of DOP in Chinese medicine formulation, quantitative method validation regarding linearity, sensitivity, precision, accuracy and stability were done in order to prove the constant relationship between DOP and its converted oligosaccharide markers. At first, the specificity of the marker was investigated by using the same procedures on the oligosaccharide fragments of other herbal ingredient in Tonic Vitality Confection (TVC) and Granule Dendrobii (GD). As stated, the herbal ingredients of TVC includes *Dendrobium officinale*, Panacis Quinquefolii Radix, Ophiopogonis Radix, Coicis Semen, Polygonati Rhizoma and Phragmitis Rhizoma while that of GD included *Dendrobium officinale* and Panacis Quinquefolii Radix. As shown in FIG. 11A-11B, the specific oligosaccharide markers, Te-Man-ABEE and Pen-Man-ABEE, did not show any overlapping in the extracted ion chromatograms (EIC) with oligosaccharides produced from other herbal ingredients. Thus, they were able to be selected as the quality control markers for the authentication of DOP in Chinese medicine formulation.

Figure 12A:
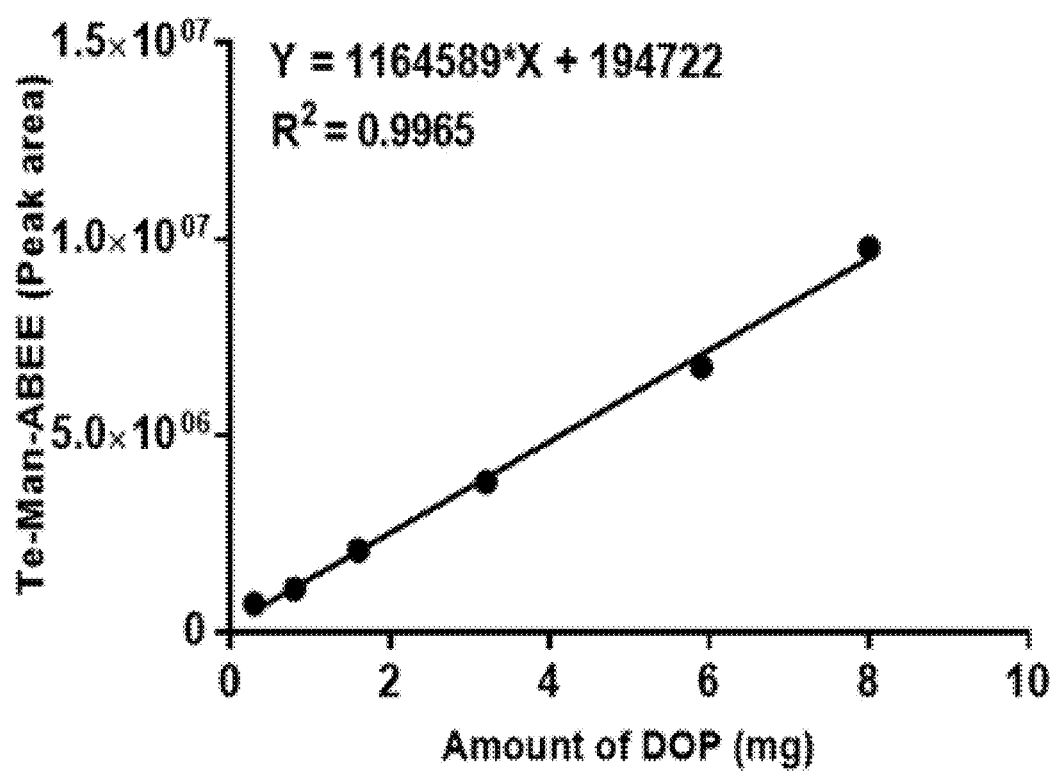
FIG. 12A shows the linear relationship between standard polysaccharides and ABEE-labeled oligosaccharide markers. Calibration curve is obtained by plotting the content of standard polysaccharides versus peak area of ABEE-labeled oligosaccharide markers. DOP versus Te-Man-ABEE.
Figure 12B:
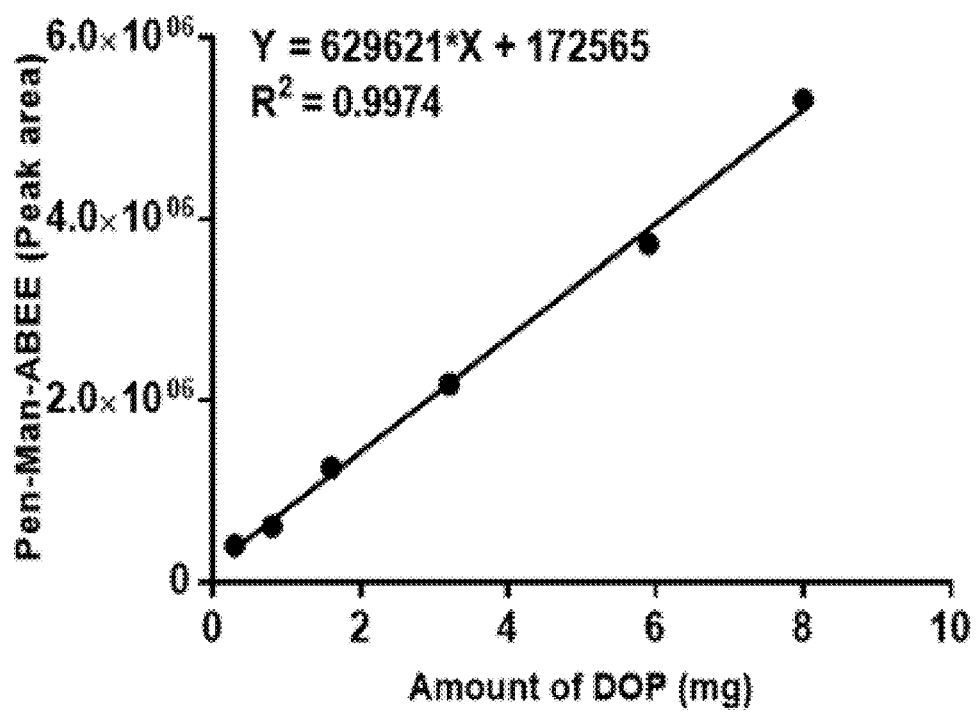
FIG. 12B shows the linear relationship between standard polysaccharides and ABEE-labeled oligosaccharide markers. Calibration curve is obtained by plotting the content of standard polysaccharides versus peak area of ABEE-labeled oligosaccharide markers. DOP versus Pen-Man-ABEE.

The quantitative results were summarized in Table 4, 5 and 6 (FIGS. 26, 27, and 28, respectively) using Te-Man-ABEE and Pen-Man-ABEE as examples. As illustrated in FIGS. 12A-12B and Table 4 (FIG. 26), the linearity calibration curve of Te-Man-ABEE and Pen-Man-ABEE showed good linearity with coefficients ($R^2$) no less than 0.997. Regarding precision of the method in Table 5 (FIG. 27), the relative standard deviation (RSD) of intra-day and inter-day precision of Te-Man-ABEE in all the samples were less than 4.76% and 6.67% respectively, while that of Pen-Man-ABEE in all the samples were all less than 3.66% and 6.91%. In relation to the recovery test, the developed method was reproducible with a good accuracy in the range of 90%-120%. Concerning the accuracy of the content of DOP calculated by the two oligosaccharide markers in *Dendrobium officinale* water extract, TVC and GD, both of the markers showed approximate results with RSD not more than 7.01%, 3.72% and 1.48% respectively (Table 6, FIG. 28).

Figure 13A:
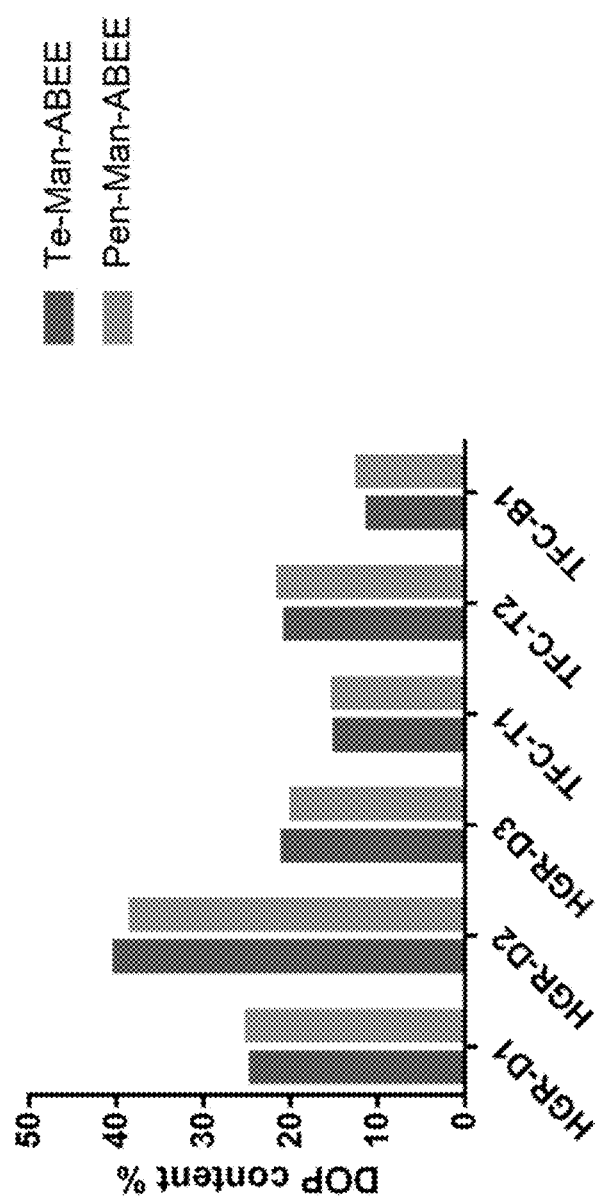
FIG. 13A illustrates the quantitation of DOP by the established method. Water extracts of six batches of *Dendrobium officinale*.
Figure 13B:
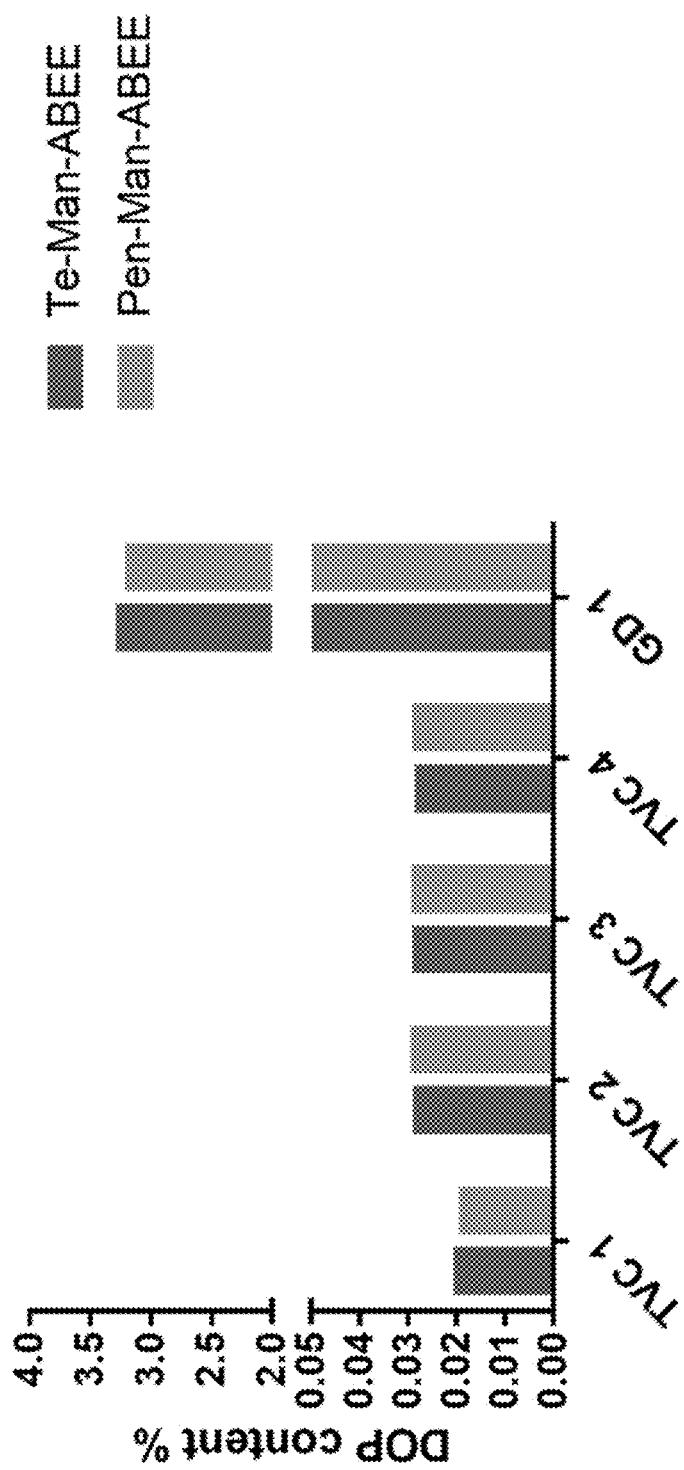
FIG. 13B illustrates the quantitation of DOP by the established method. Water extracts of four batches of Tonic Vitality Confection (TVC) and one batch of Granule Dendrobii (GD).

In relation to the amount of DOP detected in *Dendrobium officinale* water extract, Tonic Vitality Confection (TVC) and Granule Dendrobii (GD) in FIGS. 13A-13B and Table 6 (FIG. 28), the percentage of content of DOP in the samples were calculated.

It showed that more than 19.8% of DOP were determined in the dry-powdered samples compared to only 10.1% in fresh samples. This may be due to the water content in the fresh samples is much more than that in the dry-powdered samples. Thus, the DOP content is more concentrated in the dry-powered samples. Awareness is needed to be arose when determine the composition of different types of *Dendrobium officinale* in Chinese medicine formulation. Referring to the amount of DOP found in real samples, TVC and GD, both samples were found to contain DOP. In addition, the DOP content was found to be consistent in three batches of TVC except for sample, TVC 1. The DOP content in TVC was about 0.028% while 3.2% in GD.

The present disclosure also provides a method for analyzing and identifying specific polysaccharides in Radix Astragali, Radix Angelica Sinensis, and related formulas based on the ABEE labeled oligosaccharide markers. The first section is for identification in individual herbs, the steps comprising: providing a chemical profile of one or more polysaccharides in different batch of samples based on molecular distribution pattern of water extract from the said sample; separating the common and dominant component of the carbohydrates in samples, the sample having a number of polysaccharides, where the dominant polysaccharide component is the component of the samples having a largest number of polysaccharides in said sample, mildly hydrolyzing the dominant polysaccharide component by acid, releasing oligo/monosaccharides; and labeling the hydrolysates with a ABEE (or an analog thereof) label; and developing an oligosaccharide chromatographic profiles to identify the individual herb polysaccharide; and identifying the representative oligosaccharides in the profiles using prepared markers.

The macromolecule range of the separated polysaccharides is in a range constituting a molecule with a retention time between 25-27 min, which can correspond to pullulan related saccharides with a molecular weight of 50 kDa-400 kDa.

The hydrolyzing of the separated polysaccharide by mild acid, releasing the free oligosaccharides. And the released oligosaccharides are labelled with ABEE or an analog thereof, resulting in ABEE labeled oligosaccharides.

In certain embodiments, the development of an ABEE labeled oligosaccharide profile is conducted using a C-18 column detected by UPLC-DAD-qTOF-MS.

The step of identifying representative oligosaccharides comprises comparing the retention time and mass fragmentation of the representative oligosaccharide markers in the profiles with structure-known individual polysaccharide-derived oligosaccharides markers.

Also provided herein is a method for identification of Radix Astragali polysaccharide (RAP) and Radix Angelica polysaccharide (ASP) in a related herbal formula, the steps comprising: selecting the ABEE (or analogs thereof) labeled oligosaccharide markers; mildly hydrolyzing the herbal formula by acid directly, releasing oligo/monosaccharides; and labeling the hydrolysates with a ABEE (or analogs thereof) label; and analyzing labelled saccharides using LC-MS; comparing retention time and mass fragmentation of the selected oligosaccharide markers in extraction ion chromatograms with oligosaccharide-markers for Radix Astragali polysaccharide and Radix Angelica polysaccharide.

Related herbal products can comprise Danggui Buxue Tang (DBT) prepared by mixing Radix Astragali and Radix Angelica Sinensis.

Also provided herein is a method for identifying the polysaccharide in herbs and related formulas using ABEE or ABEE analog labeled oligosaccharide markers, the method comprising: separating and preparing the dominant polysaccharide as a standard polysaccharide of the said sample; basic quality control of the standard polysaccharide; mildly acid hydrolyzing the standard polysaccharide component, releasing oligo/monosaccharides; and labeling the hydrolysates with ABEE (or analogs thereof); and selecting a representative oligosaccharide marker; establishing the linearity relationship between the standard polysaccharide and the representative labeled oligosaccharides marker; validating the quantitative method; and analyzing the specific polysaccharide content in Radix Astragali water extracts, Radix Angelica sinensis water extracts, and related products.

In certain embodiments, the step of standard polysaccharide preparation is conducted by means comprising precipitation and filtration. The precipitation can be conducted by using 10-90% v/v ethanol. The filtration can be conducted using an ultra-centrifugal filtration with a 3-10 kDa cutting-off.

In certain embodiments, the standard polysaccharide selection criteria can include molecular weight, total sugar content, protein content, uronic acid content and monosaccharide composition determination.

In certain embodiments, selection criteria of standard polysaccharide compromise: 1) The polysaccharide has a retention time between 25-27 min in chromatographic separations, which further corresponds to 50-400 kDa of pullulan series; 2) the total content of sugar and uronic acid should be more than 90%; 3) the protein content should be less than 5%; 4) the monosaccharide composition should be repeatable.

In certain embodiments, representative oligosaccharide markers used satisfy the conditions mentioned in qualitative analysis. Besides the marker selected preferably have satisfactory method validation results.

In certain embodiments, the peak area of representative marker is recorded by integrating the peak signals in extract ion chromatograms. The step of linearity relationship between oligosaccharide the calibration curve is plotted by polysaccharide amount versus peak area of the labeled oligosaccharide marker.

Method validation can include establishing linearity, repeatability, and accuracy of the method.

The developed method can be applied to direct polysaccharide quantitation of Radix Astragali and related products. The related formulas include DBT. DBTs were prepared by Radix Astragali and Radix Angelica Sinensis in the weight of different ratio.

Chemicals: Pullulan series were from Sigma-Aldrich Corp. (St. Louis, USA). Monosaccharide standards including glucose (Glc), mannose (Man), galactose (Gal), rhamnose (Rha), arabinose (Ara), fucose (Fuc), glucuronic acid (GluA), and galacturonic acid (GalA) were obtained from Sigma (St. Louis, Mo., United States). Pullulan series were from Sigma. BCA kit for protein analysis was purchased from Thermo. M-phenyl phenol, sodium borate, concentrated sulfuric acid, trifluoroacetic acid (TFA), ABEE, sodium cyanoborohydride and other related chemical regents were all purchased from Sigma-Aldrich Corp. (St. Louis, USA).

Preparation of Polysaccharides of Radix Astragali and Radix Angelica sinensis

Radix Astragali and Radix Angelica Sinensis were purchased from local retail or wholesale drug stores in Hong Kong, China. The dried pieces of Radix Astragali and Radix Angelica Sinensis were powdered and extracted with water to obtain polysaccharides. In brief, plant powders were extracted with water. The extracted solutions were centrifuged, and the supernatants (the crude polysaccharide solutions) were combined, condensed, and then precipitated in 60% ethanol to get crude polysaccharide precipitate, which was re-dissolved in water and passed through ultrafiltration using membrane centrifuge tubes with molecular size cutting-off of 3 kDa. The supernatant after 60% ethanol precipitation and filtrate after ultrafiltration were kept for investigation of marker specificity.

Radix Astragali and Radix Angelica Sinensis Herbal Sample Preparation

Water extracts: Each batch of dried sample powder of Radix Astragali or Radix Angelica Sinensis (1.0 g) was subjected to solid-liquid extraction using water at 100° C. (20 mL×2 h×2 times), respectively. The extracted solutions were centrifuged at 3,500 rpm for 10 min. The supernatants were then combined for further analysis.

Danggui Buxue Tang preparation: Dried sample powders of Radix Astragali and Radix Angelica Sinensis were combined in the ratio, by weight, of 1:0, 5:1, 3:1, 1:1, 1:3 and 1:5. The mixtures (total 1.0 g) were extracted using the same procedure as water extract preparation. Supernatants were then combined for further analysis.

Partial acid hydrolysis and ABEE-labeling: The dried polysaccharide (between 0.5-12.0 mg) was dissolved in 2 mL aqueous TFA (1.0 mol/L) and partially hydrolyzed at 80° C. for 2 h, respectively. After removing the TFA, hydrolyzed products (mono/oligosaccharides) were re-dissolved in 1.5 ml of 60% (V/V) methanol in water and the solution was centrifuged at 15,000 rpm for 3 min. The supernatant containing the hydrolyzed sample was collected for further analysis.

100 μL of the supernatant containing the hydrolyzed sample was dried and re-dissolved in 200 μL water. The sample solution was then mixed with 560 μL derivatization reagent (400 μL 0.6 mol/L ABEE, 80 μL, glacial acetic acid and 80 μL 1.4 mol/L sodium borohydide) and incubated at 65° C. for 2 h. After cooling, water and diethyl ether (900 μL) were added to the solution, and the mixture was fully mixed and centrifuged at 15,000 rpm for 5 min. The upper layer (ABEE solution) was removed and the remaining water phase was dried, re-dissolved in 500 μL of 60% (V/V) methanol, and finally subjected to LC-MS analysis.

LC-DAD-qTOF-MS conditions: The separation was performed on an Agilent 1290 UHPLC system (Agilent Technologies, Santa Clara, USA) equipped with a binary pump, a thermostatic column compartment, an auto-sampler, and a degasser and a diode-array detector (DAD). The system was controlled by Mass Hunter B.06 software. The chromatographic column ACQUITY UPLC BEH C18 (2.1 mm×100 mm, 1.7 μm, Waters, Milford, USA) was used and eluted with a linear gradient of 0.1% formic acid in water (A) and 0.1% formic acid in acetonitrile (B) at a flow rate of 0.4 mL/min and at a temperature of 30° C. The solvent gradient programming was as follows: 0-5 min, 10% B; 5-18 min, 10-18% B; 18-23 min, 18-25% B; 23-26 min, 25-100% B; 26-29 min, 100% B; 29-29.1 min, 100-10% B; 29.1-34 min, 10% B. The injection volume was 1 μL.

MS data were collected from an Agilent 6540 Q-TOF mass spectrometer (Agilent Technologies, Santa Clara, USA) equipped with a quadrupole-time-of-flight (Q-TOF) mass spectrometer and a JetStream electrospray ion (ESI) source. Data acquisition was controlled by MassHunter B.06 software (Agilent Technologies). The optimized operating parameters in the negative ion mode were as follows: nebulizing gas ($N_2$) flow rate, 7.0 L/min; nebulizing gas temperature, 300° C.; Jet Stream gas flow, 8 L/min; sheath gas temperature, 350° C.; nebulizer, 40 psi; capillary, 3000 V; skimmer, 65 V; Oct RFV, 600 V; and fragmentary voltage, 150 V. The mass scan range was set as mass to charge (m/z) 100-2000 and the wavelength of 305 nm was set by DAD detection.

Oligosaccharide marker preparation and characterization: A large number of crude polysaccharides of Radix Astragali or Radix Angelica Sinensis were prepared. The prepared polysaccharides were hydrolyzed, and the hydrolysates were derivatized with ABEE as described above. The prepared freeze-dried hydrolysate (0.5 g/mL) was dissolved in a 60% MeOH/water (v/v) solution. The supernatant containing ABEE-labeled oligosaccharide fragments was kept for further marker preparation. The ABEE-labeled oligosaccharide fragments were loaded onto Alitima C18 preparation column (22×250 mm, 10 μm) and detected by UV at 305 nm. The oligosaccharide fragments of RAP were eluted with 10% acetonitrile (ACN) at a flow rate of 8 mL/min. The oligosaccharide fragments of ASP were separated by gradient elution with water containing 0.1% formic acid (A) and ACN containing 0.1% formic acid (B): 0~35 min, 15~22% B; 35~47 min, 22~50% B, 47~52 min, 50~15% B. The fraction containing markers were collected and combined and re-chromatographed on Agilent Eclipse XDB-C18 semi-preparation column (9.4×250 mm, 5 μm). The Rm-1, Rm-2 and Rm-3 were obtained by eluting with 8% ACN, and the Am-1 and Am-2 were prepared by eluting with 15% ACN containing 0.1% formic acid. The purity was monitored by LC-MS analysis. The purified markers were lyophilized. Their structures were characterized by monosaccharide analysis, linkage analysis and NMR.

Quantitative method development and validation: The LC-MS method for directly quantitative analysis of the polysaccharides in Radix Astragali, Radix Angelica Sinensis water extract and DBTs were validated in terms of linearity, precision and accuracy.

A series of standard polysaccharide RAP and ASP of 0.5, 1.0, 2.0, 4.0, 6.0, 8.0 and 10, (12) mg were precisely weighed for the construction of calibration curves. Each concentration was prepared in triplicate. The polysaccharides were subjected to partial acid hydrolysis and ABEE derivatization following the described procedures. Each sample was analyzed in duplicate, and the amounts of Rm and Am were obtained by calculation based on the calibration curve between peak area and amount of Rm-3 (1.0-32.0 μg/mL) and Am-2 (0.05-1.6 μg/mL). Relationships between variables were visualized by plotting 1) the concentration of marker versus the peak area of marker; 2) the amount of detected marker in hydrolyzed polysaccharide versus the amount of polysaccharide, and 3) the peak areas of marker in hydrolyzed polysaccharide versus the amount of polysaccharide. The marker referred to Rm-3 or Am-2, and the polysaccharide referred to RAP and ASP.

The water extract of Radix Astragali, water extract of Radix Angelica Sinensis, and DBT (1:1) were used in the following method validation. Intra-day and inter-day variations were chosen to determine the precision of the developed assay. For the intra-day variability test, six replicates of each sample were analyzed within one day, while for the inter-day variability test; duplicate of the same sample was examined for three consecutive days. Variations in the peak areas of Rm and Am were expressed by the RSD.

The spike recovery test was used to evaluate the accuracy of the method. About 25.0 mg water extract of Radix Angelica Sinensis, 50.0 mg of water extract of Radix Astragali and DBT (1:1) with known contents of polysaccharide was weighed, and different amounts (high 120%, 100% middle and 80% low level, n=3 each concentration) of the standard polysaccharide were spiked, then hydrolyzed, derived and analyzed in duplicate. The spike recoveries were calculated.

RAP and ASP determination in water extract of individual herb and DBT: Radix Astragali water extracts (50.0 mg), Radix Angelica Sinensis water extracts (25.0 mg) and 50.0 mg of DBTs were precisely weighed, hydrolyzed and derived by the described procedures. The peak areas of the Rm and Am were recorded and the contents of the polysaccharides RAP and ASP were calculated according to the established linear relationship in the developed method. Each sample was assessed in triplicate.

Figure 14:
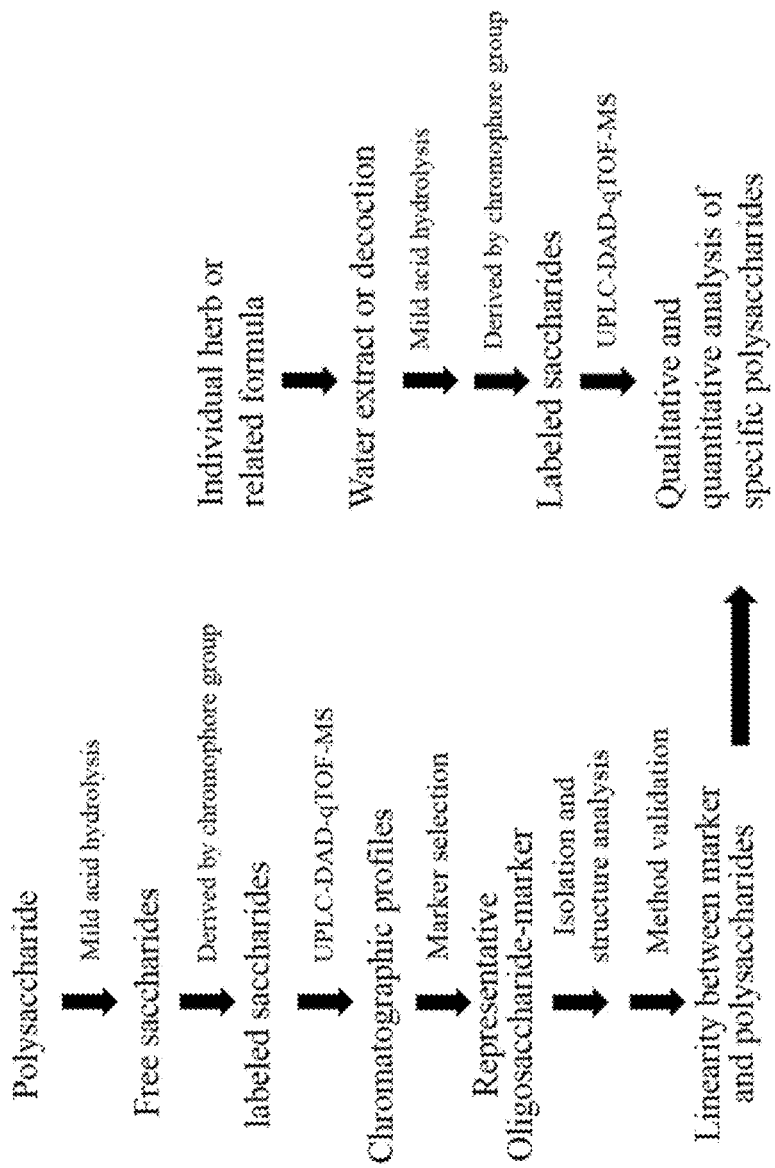
FIG. 14 shows a flow chart showing the procedure of qualitative and quantitative analysis of specific polysaccharides in individual herbs and related formulas by using oligosaccharide markers.
Figure 15A:
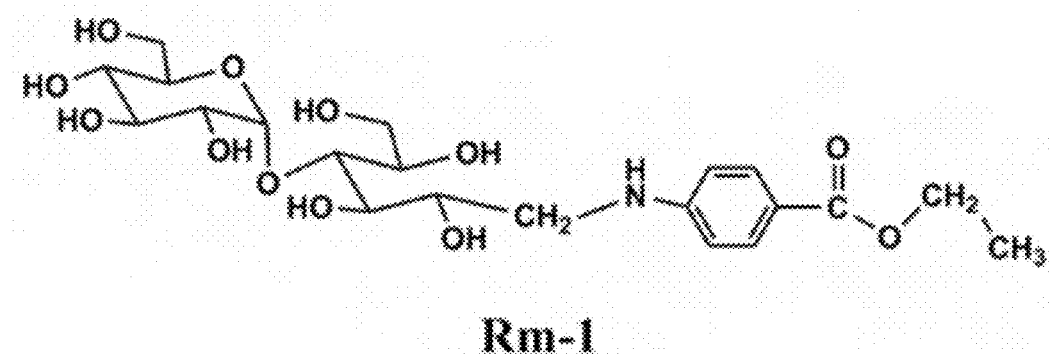
FIG. 15A shows the structure of isolated labeled-oligosaccharide of Rm-1.
Figure 15B:
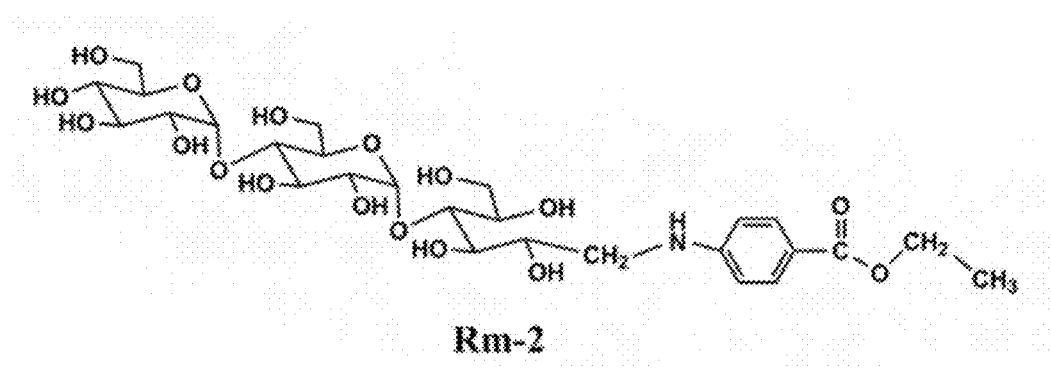
FIG. 15B shows the structure of isolated labeled-oligosaccharide of Rm-2.
Figure 15C:
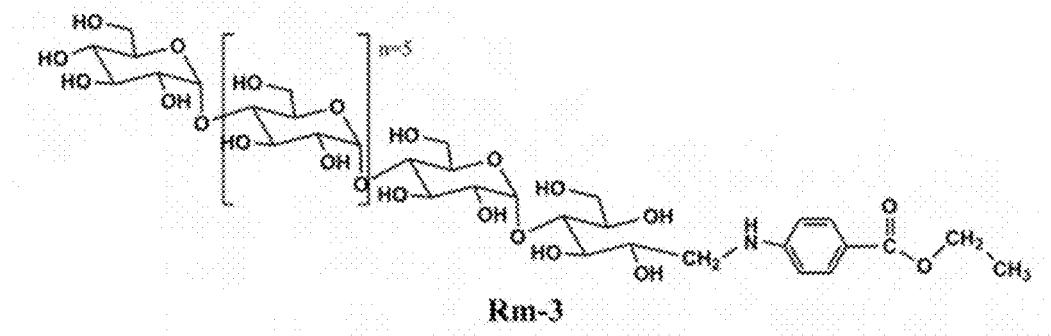
FIG. 15C shows the structure of isolated labeled-oligosaccharide of Rm-3.
Figure 15D:
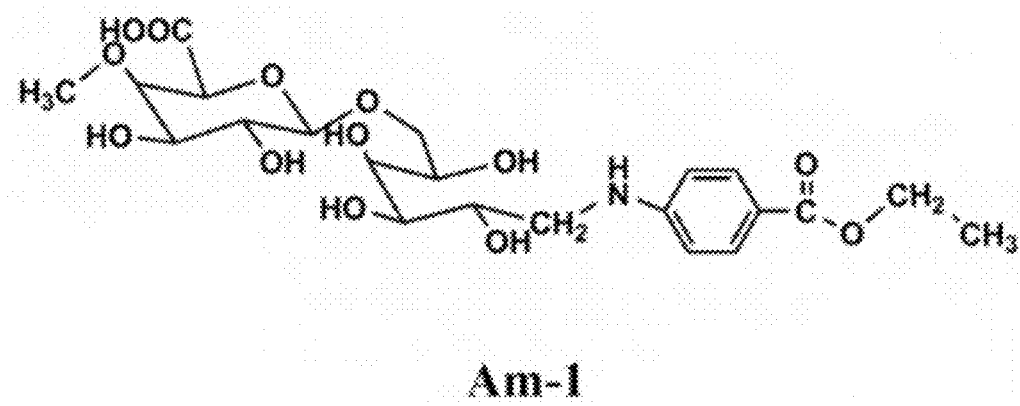
FIG. 15D shows the structure of isolated labeled-oligosaccharide of Am-1.
Figure 15E:
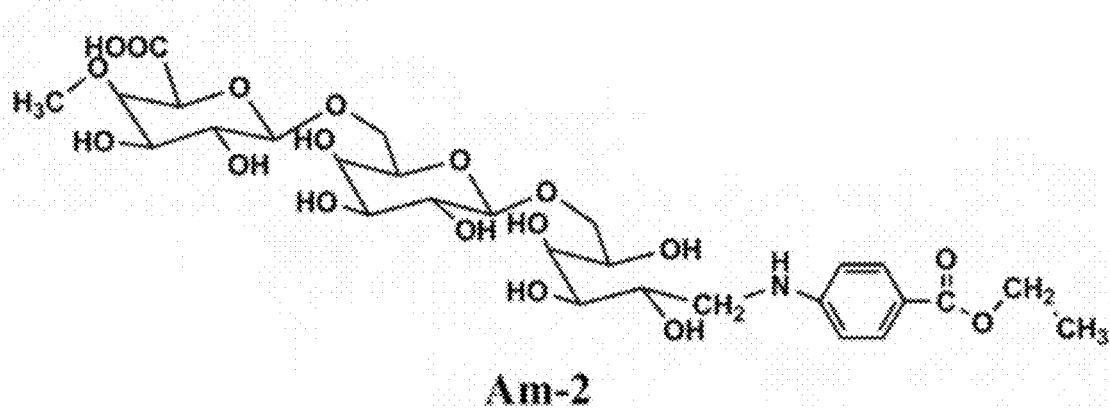
FIG. 15E shows the structure of isolated labeled-oligosaccharide of Am-2.

Structure analysis of ABEE labeled oligosaccharides: As shown in the FIG. 14, the ABEE labeled oligosaccharides were obtained. And representative oligosaccharides marker for RAP and ASP were prepared and went to structure analysis.

The structures (FIG. 15A-15E) of isolated labeled oligosaccharides were figured out through mass spectroscopy, monosaccharide composition, linkage analysis and NMR spectroscopy. According to the characteristic signals in NMR spectroscopy, the $^{13}$C-NMR and $^1$H-NMR spectra were completely analyzed based on two-dimensional HSQC, HMBC and $^1$H-$^1$H COSY experiments, together with comparison to the reported NMR data.

Figure 16:
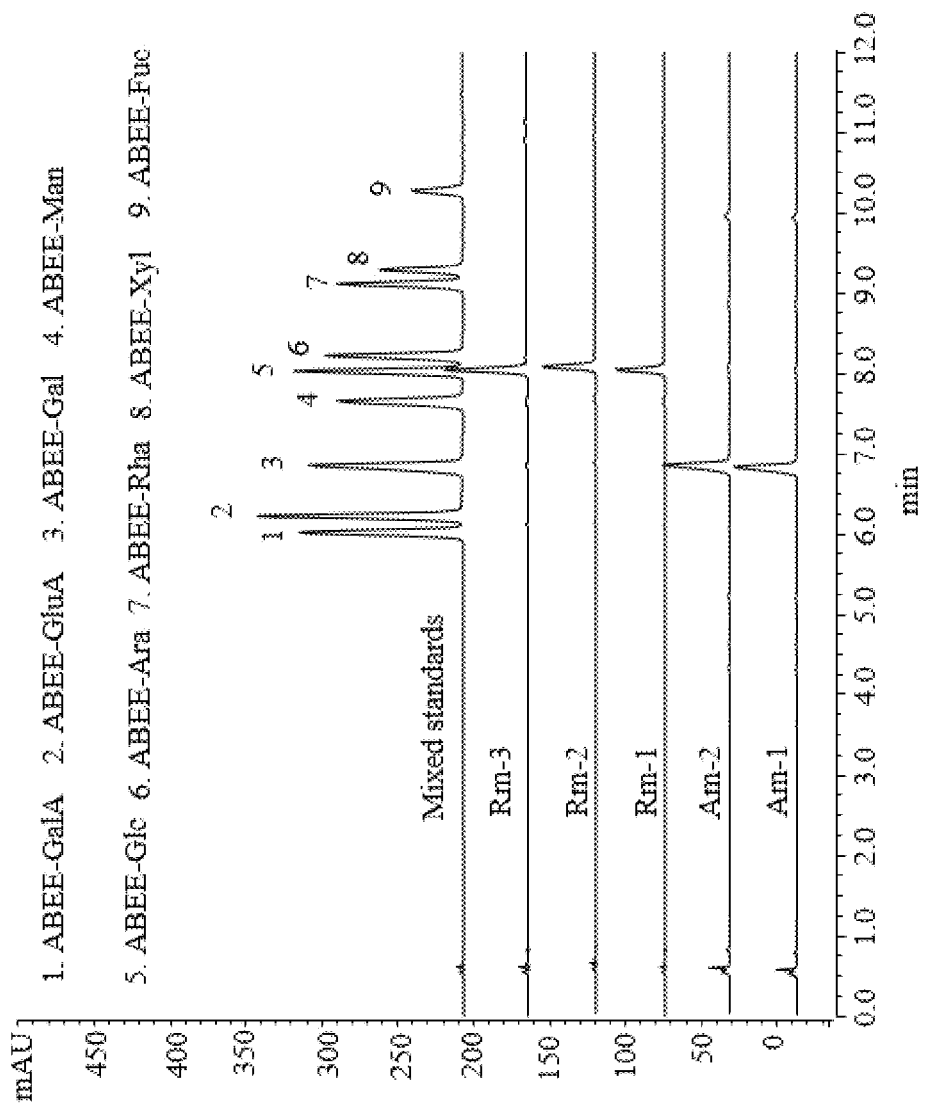
FIG. 16 shows the monosaccharide composition of Rm-1, Rm-2 and Rm-3, Am-1 and Am-2. Mixed standards contained the following ABEE-labeled saccharides: galacturonic acid (ABEE-GalA), glucuronic acid (ABEE-GluA), galactose (ABEE-Gal), mannose (ABEE-Man), glucose (ABEE-Glc), arabinose (ABEE-Ara), rhamnose (ABEE-Rha), xylose (ABEE-Xyl) and fucose (ABEE-Fuc).
Figure 17A:
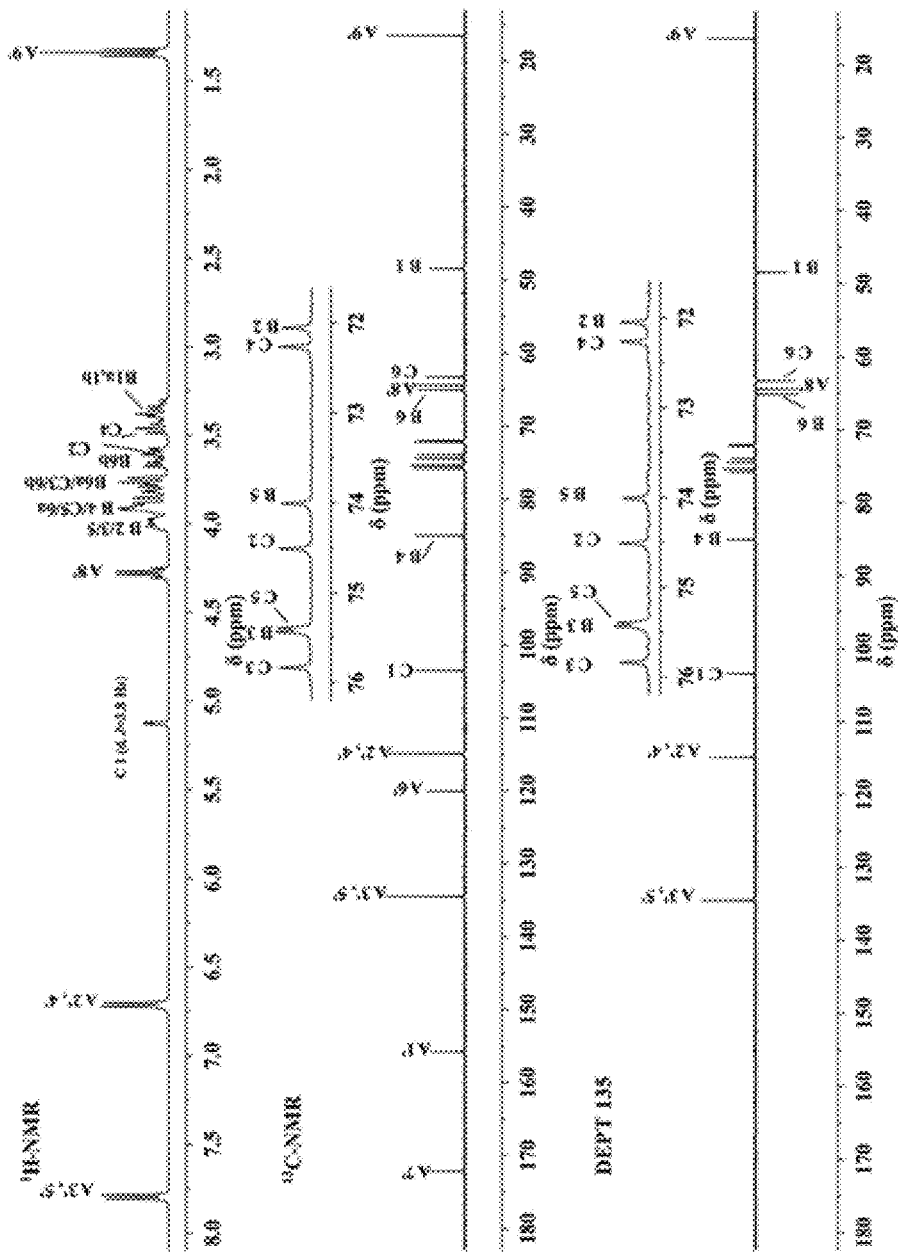
FIG. 17A shows the $^1$H-NMR, $^{13}$C-NMR and DEPT135 of Rm-1.
Figure 17B:
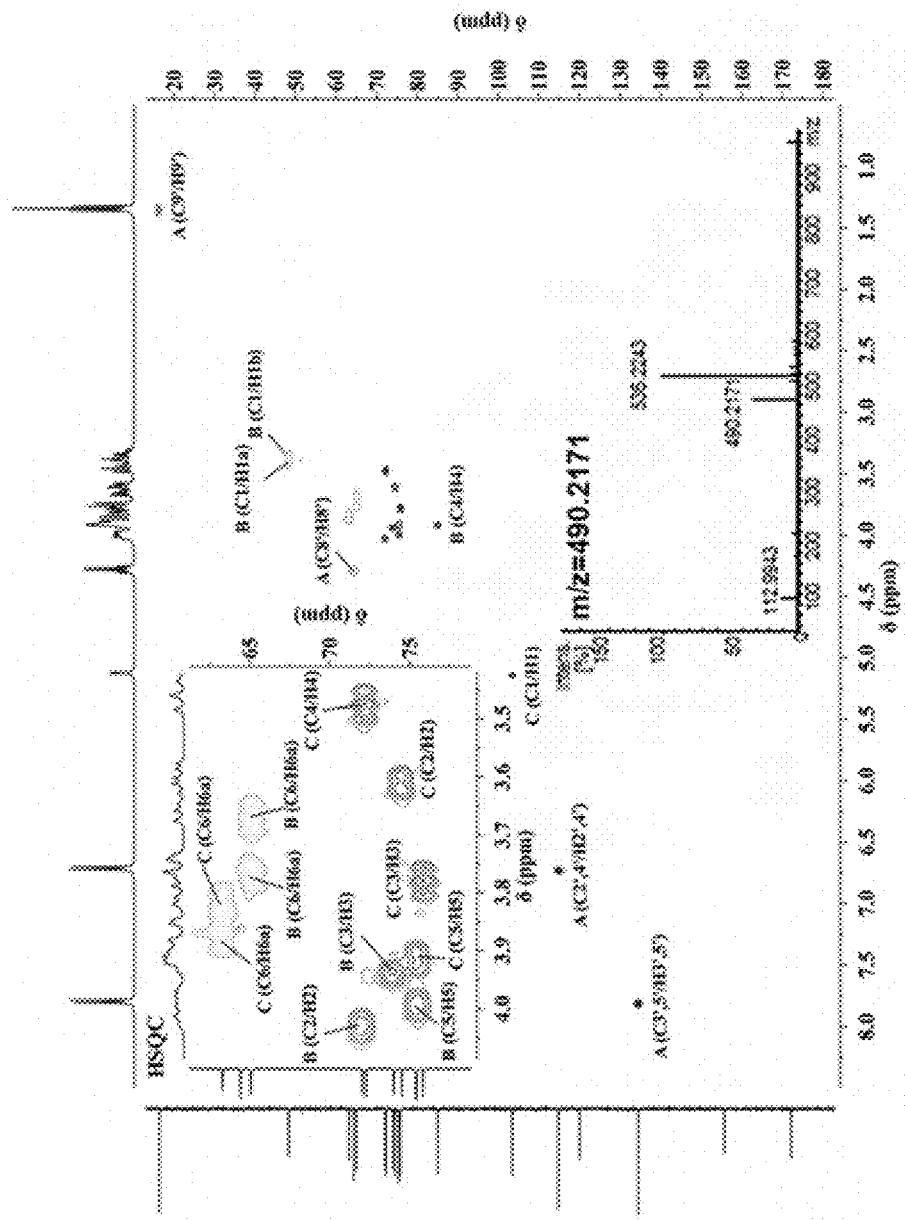
FIG. 17B shows the MS and HSQC of Rm-1.
Figure 17C:
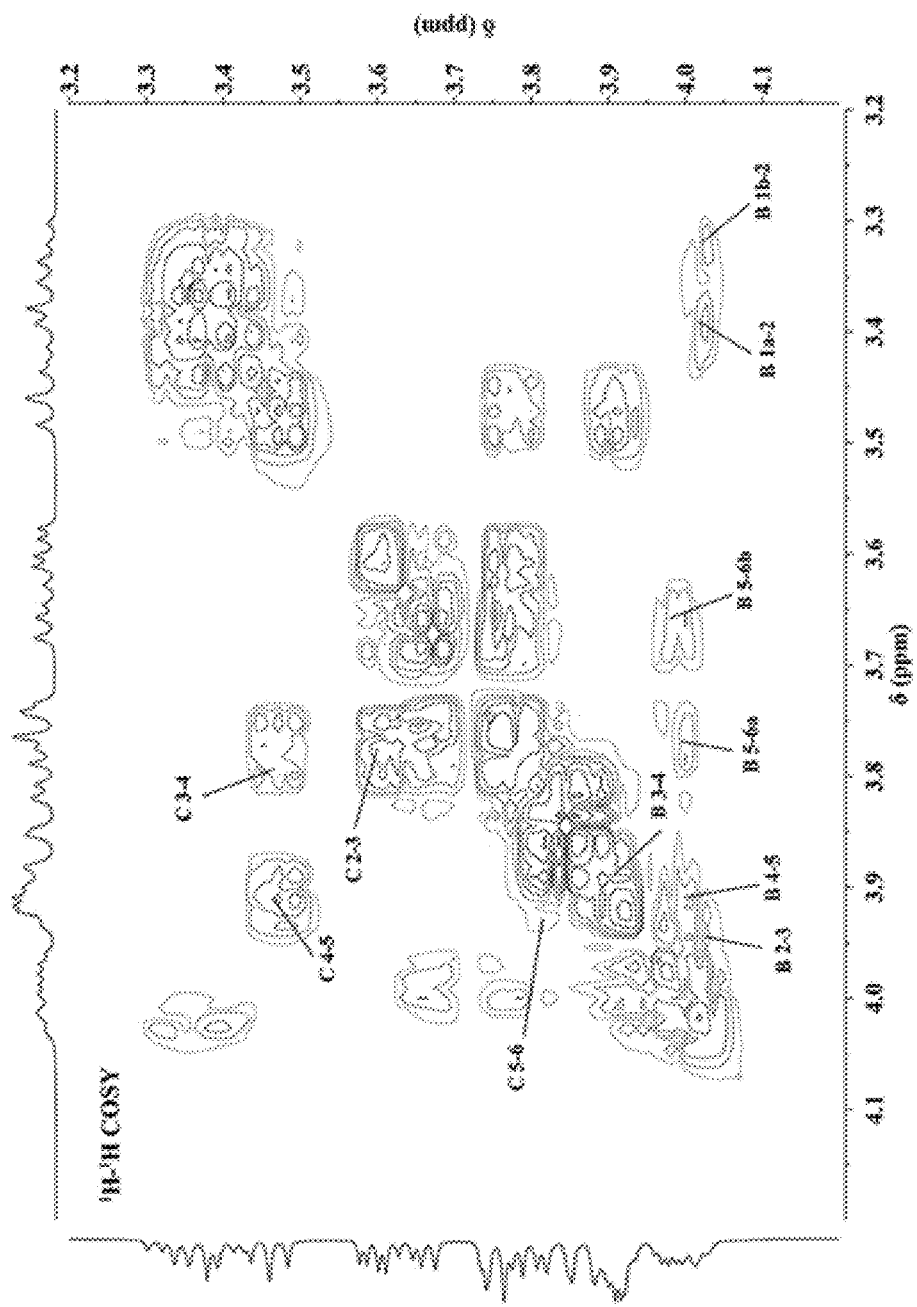
FIG. 17C shows the $^1$H-$^1$H COSY of Rm-1.
Figure 17D:
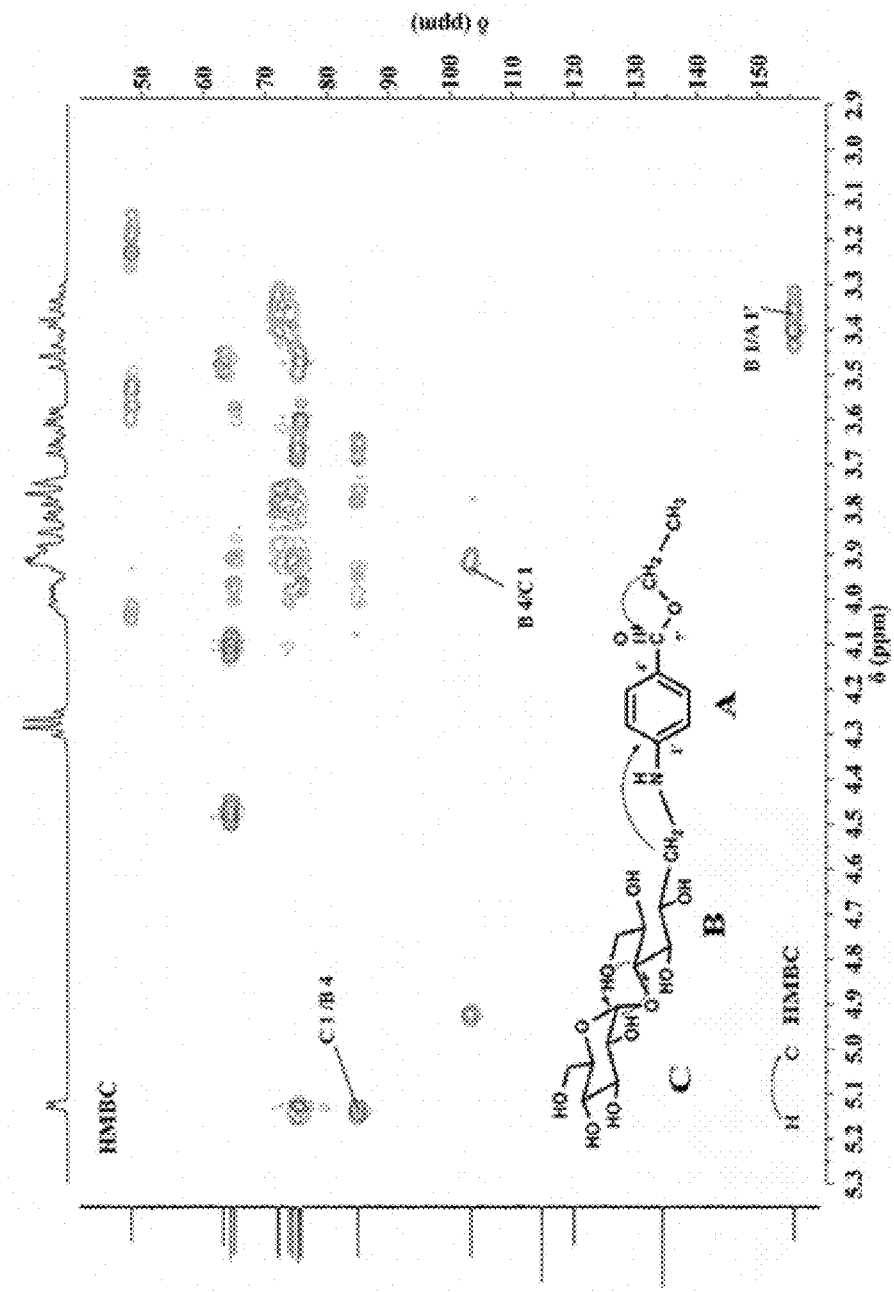
FIG. 17D shows the HMBC of Rm-1.
Figure 17E:
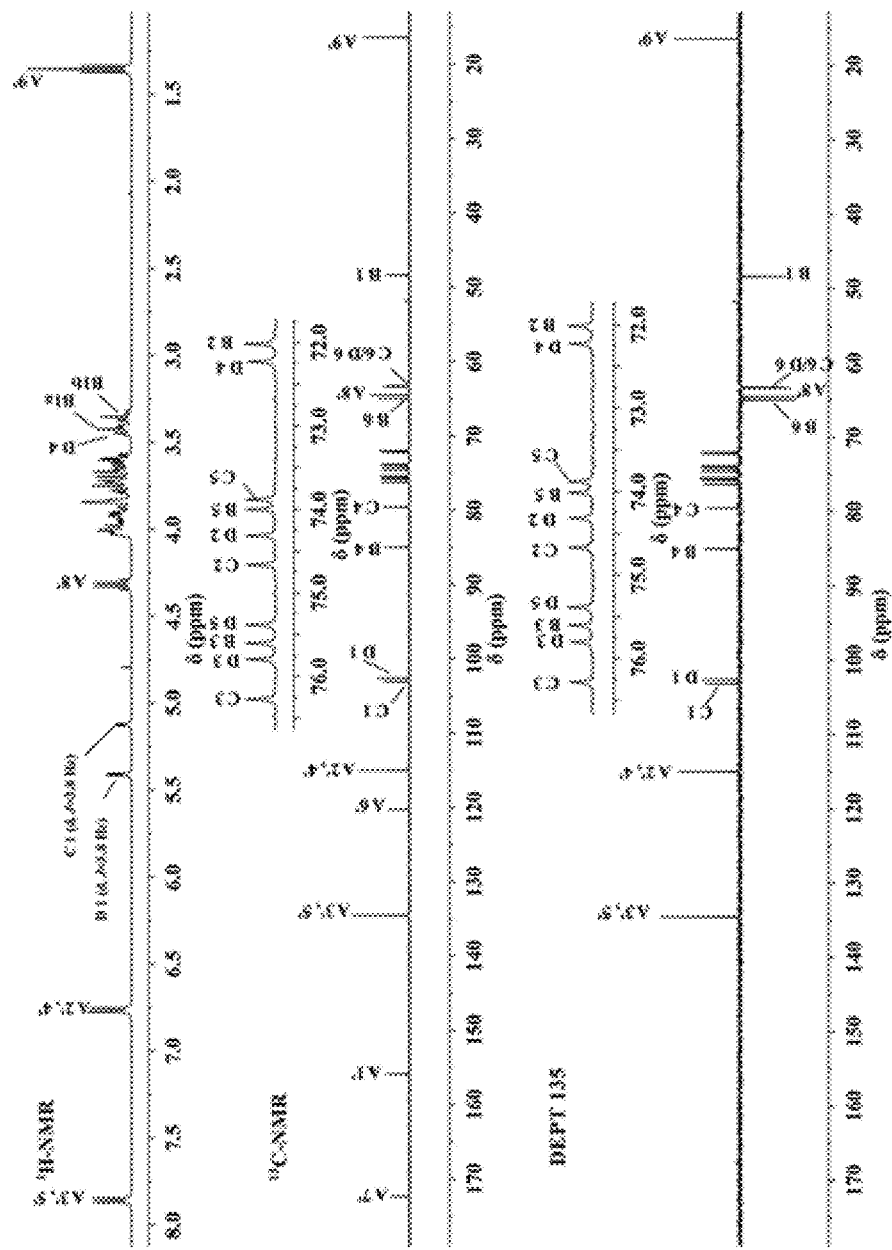
FIG. 17E shows the $^1$H-NMR, $^{13}$C-NMR and DEPT135 of Rm-2.
Figure 17F:
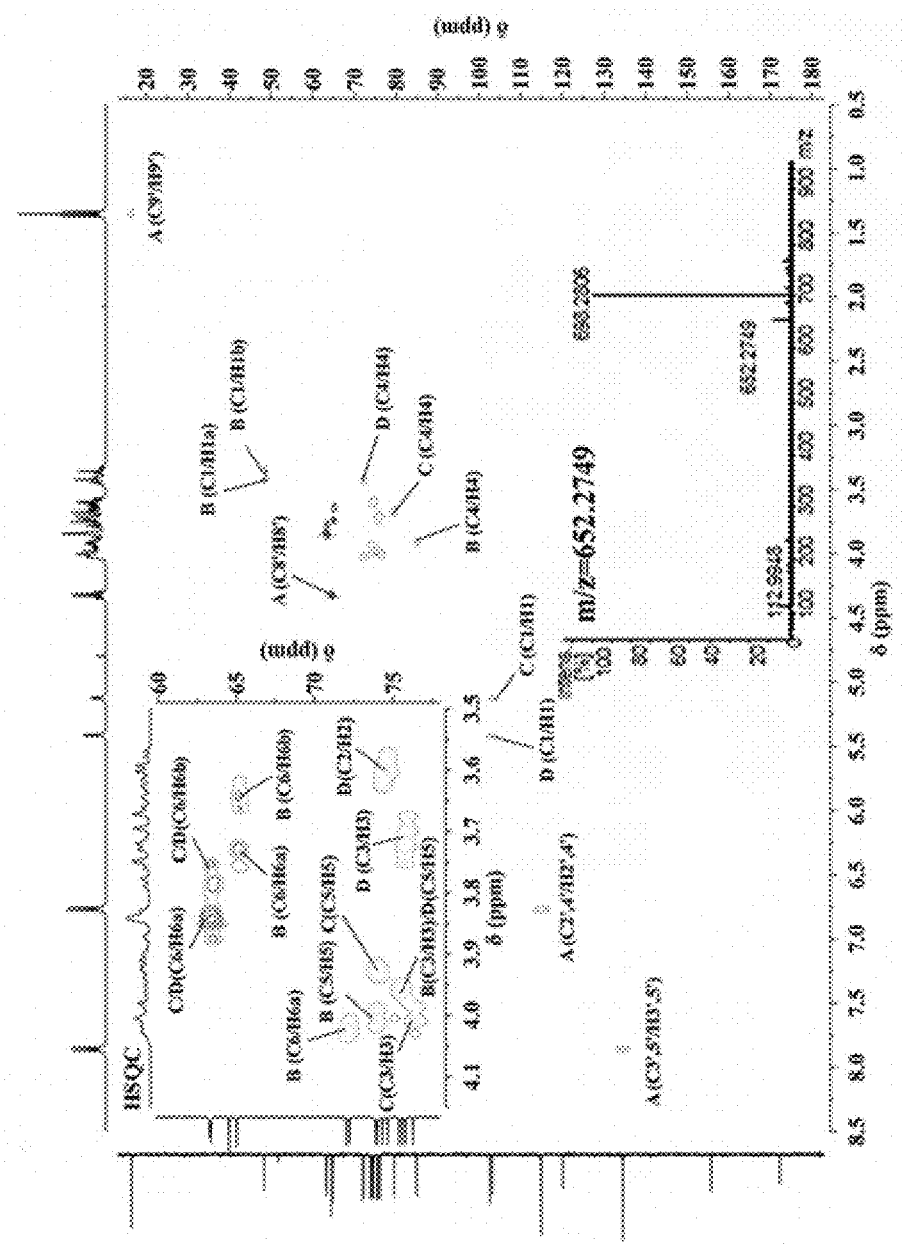
FIG. 17F shows the MS and HSQC of Rm-2.
Figure 17G:
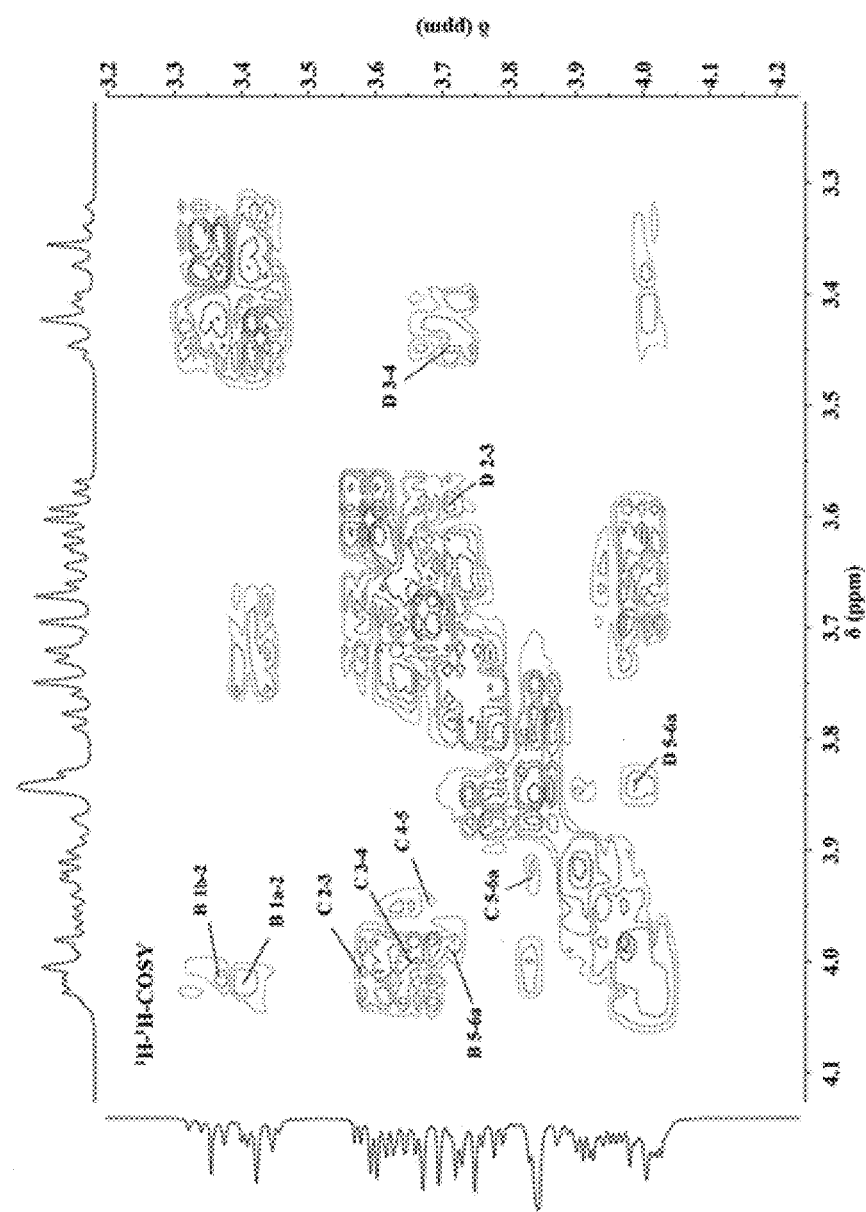
FIG. 17G shows the $^1$H-$^1$H COSY of Rm-2.
Figure 17H:
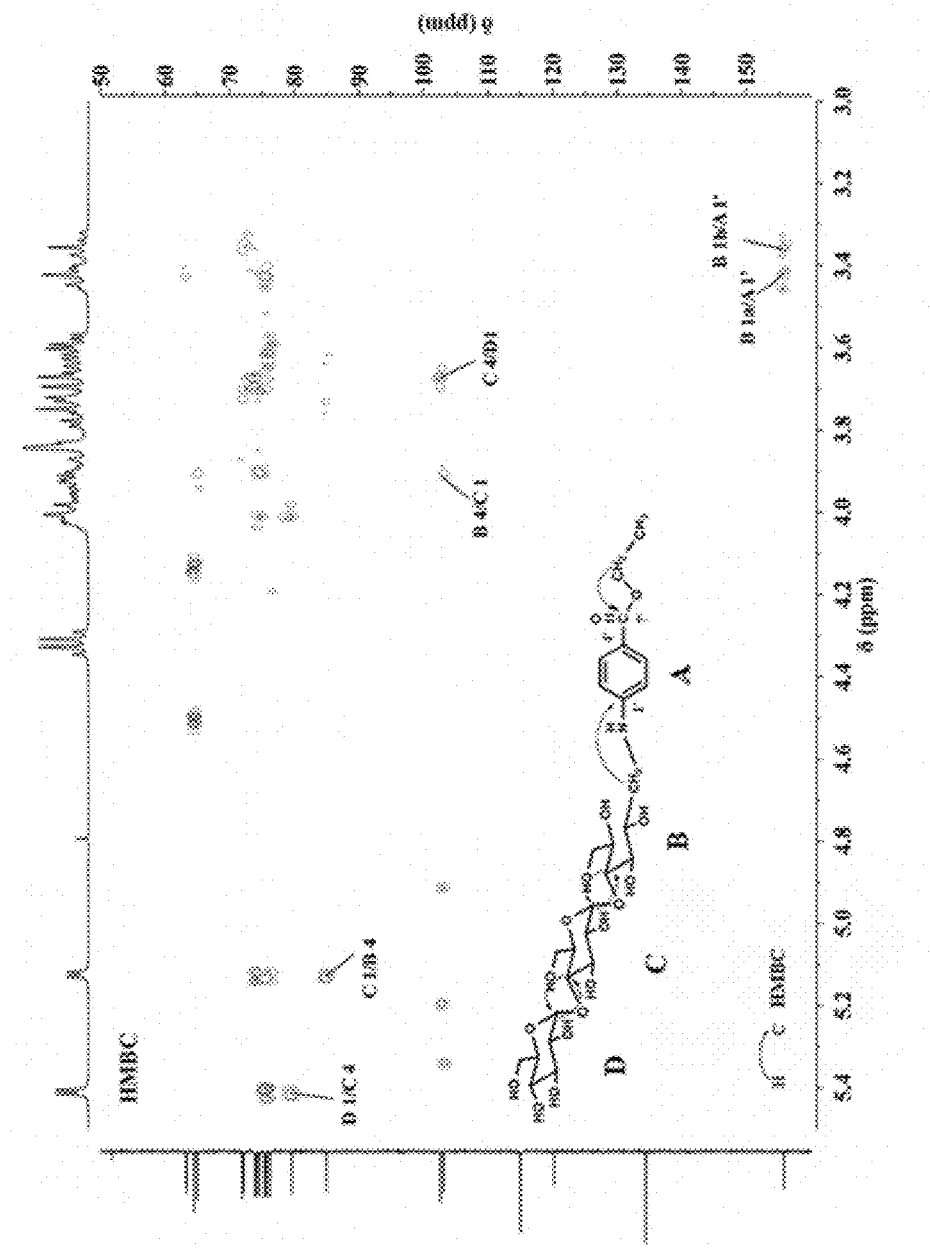
FIG. 17H shows the HMBC of Rm-2.
Figure 17I:
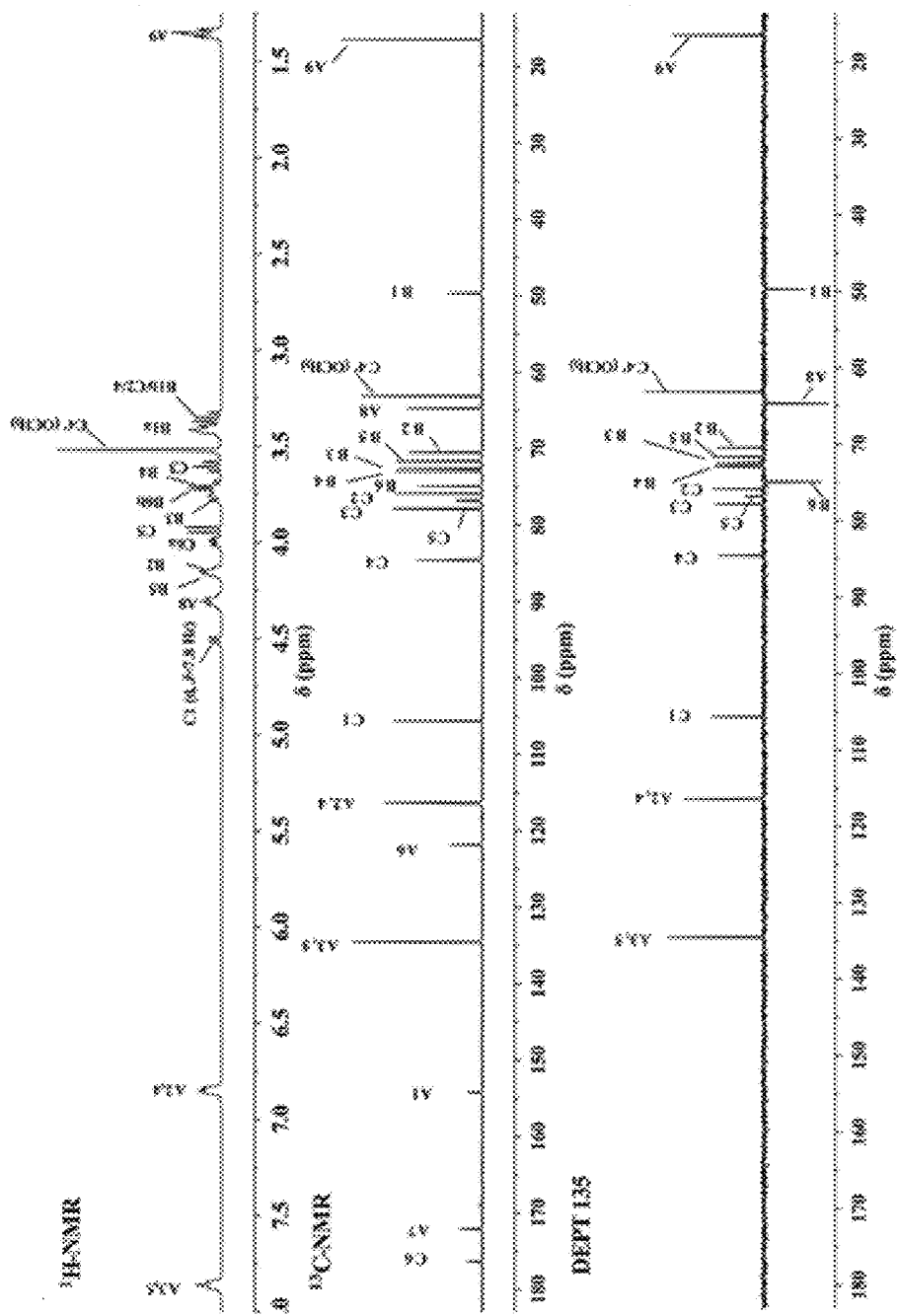
FIG. 17I shows the $^1$H-NMR, $^{13}$C-NMR and DEPT135 of Rm-3.
Figure 17J:
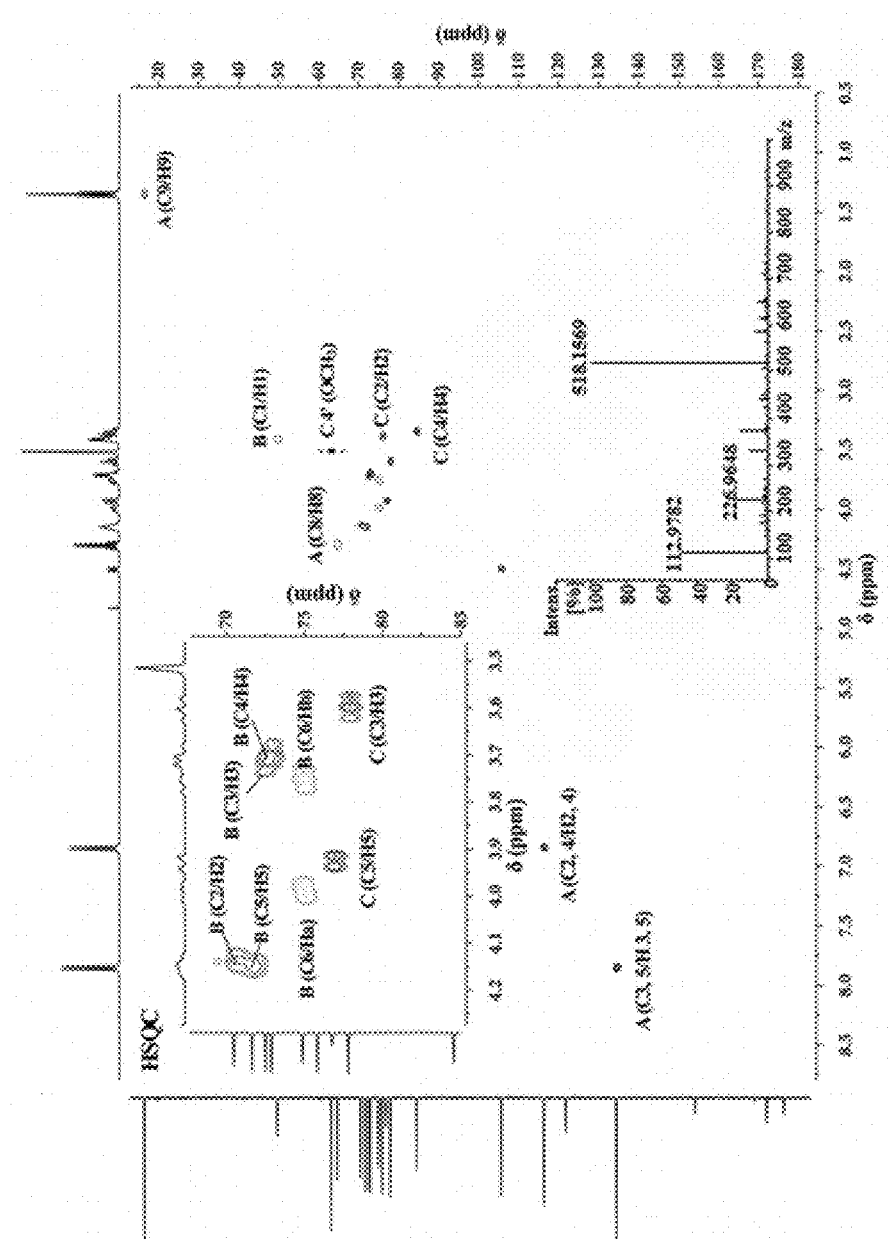
FIG. 17J shows the MS and HSQC of Rm-3.
Figure 17K:
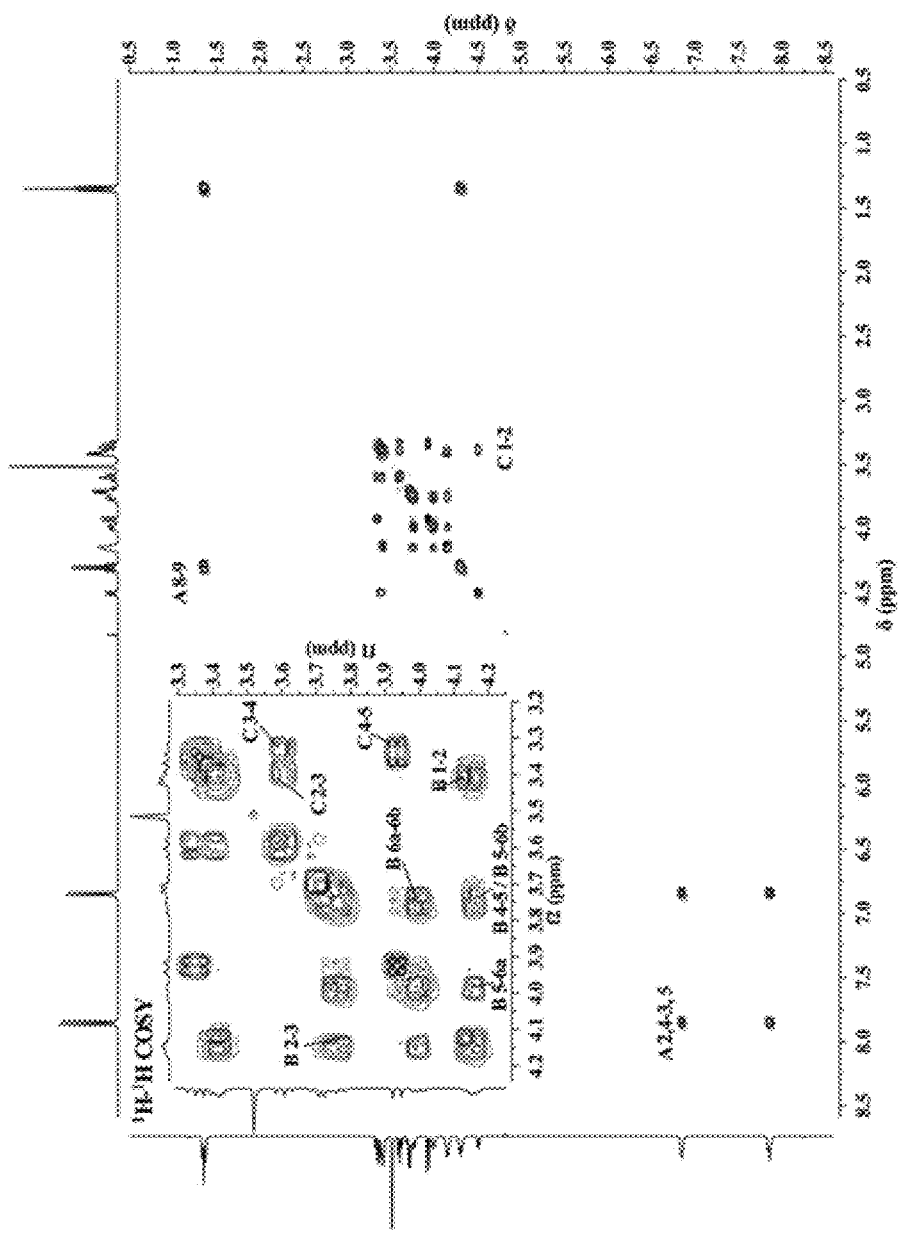
FIG. 17K shows the $^1$H-$^1$H COSY of Rm-3.
Figure 17L:
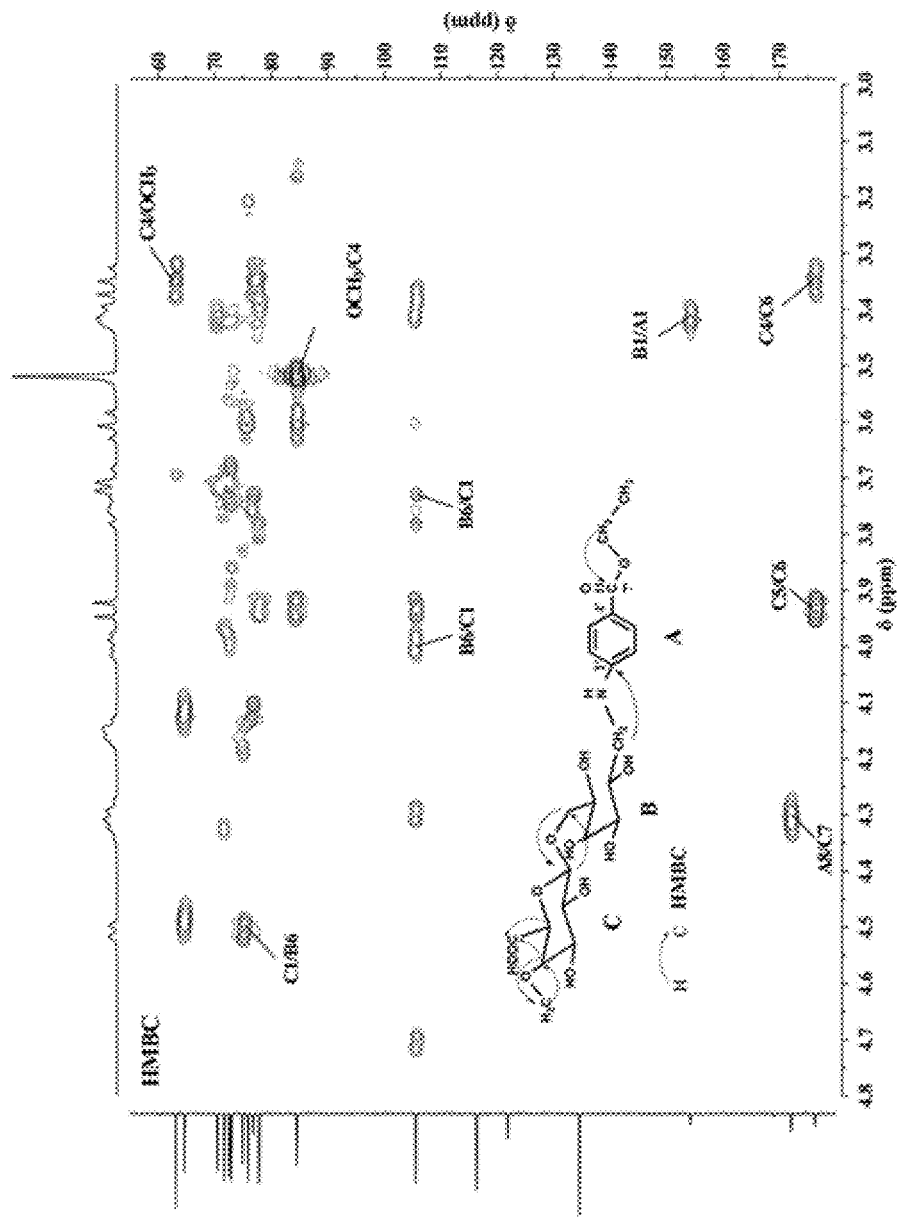
FIG. 17L shows the HMBC of Rm-3.
Figure 17M:
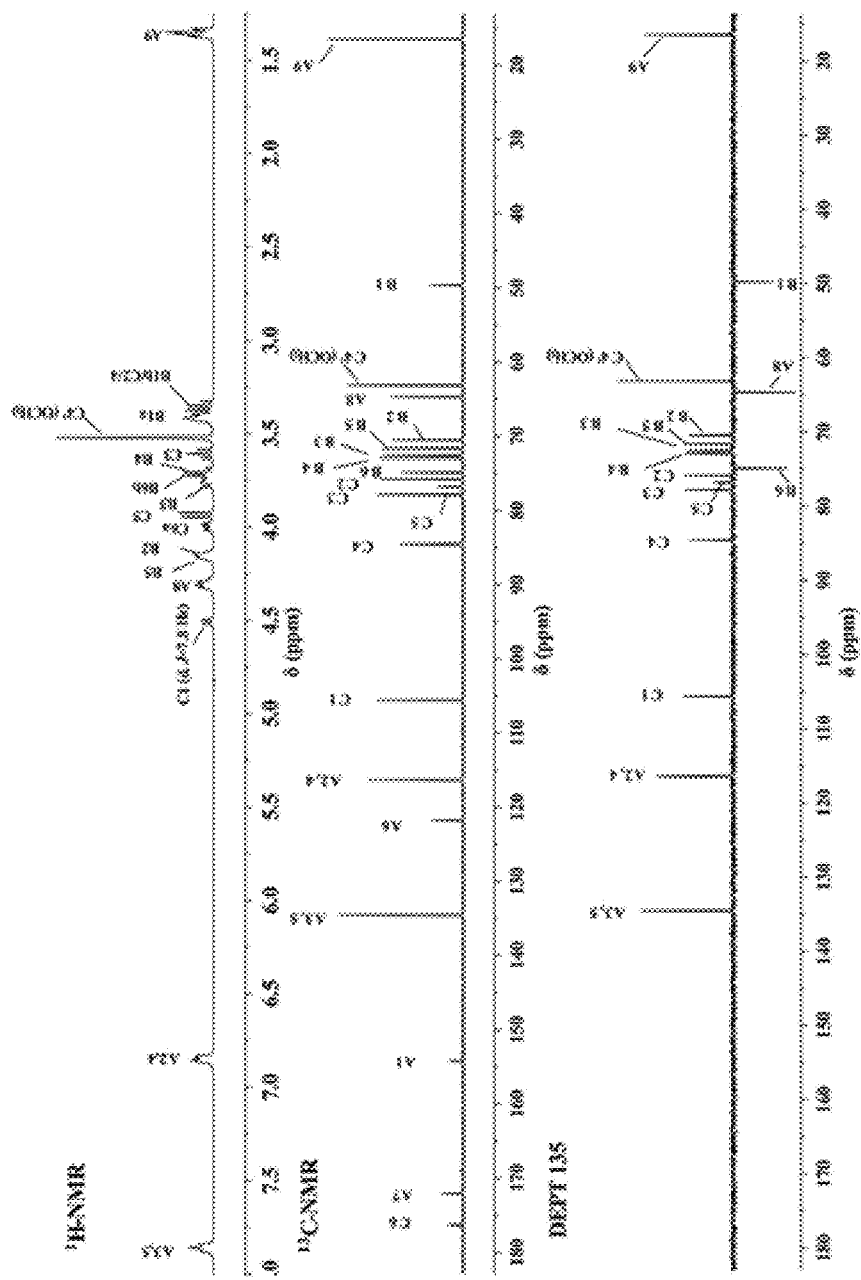
FIG. 17M shows the $^1$H-NMR, $^{13}$C-NMR and DEPT135 of Am-1.
Figure 17N:
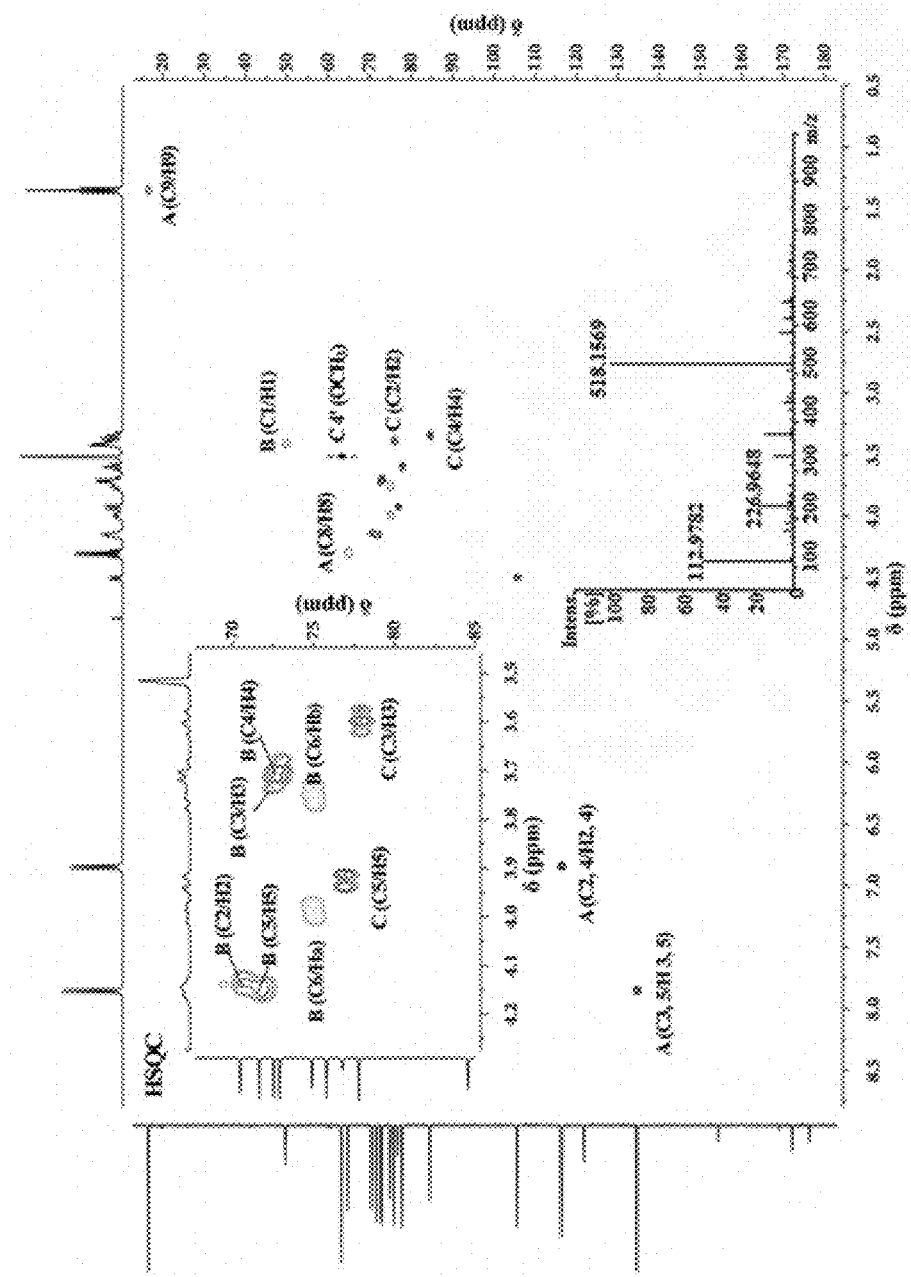
FIG. 17N shows the MS and HSQC of Am-1.
Figure 17O:
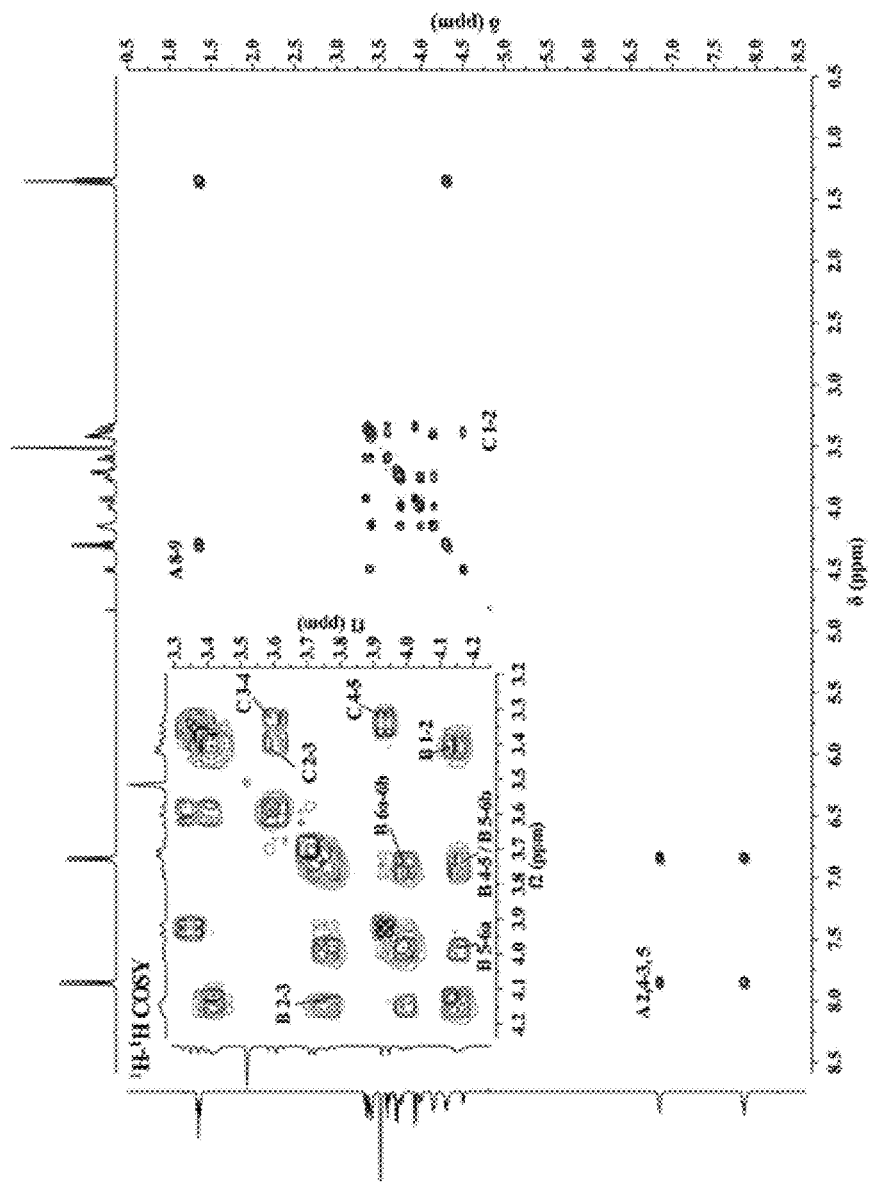
FIG. 17O shows the $^1$H-$^1$H COSY of Am-1.
Figure 17P:
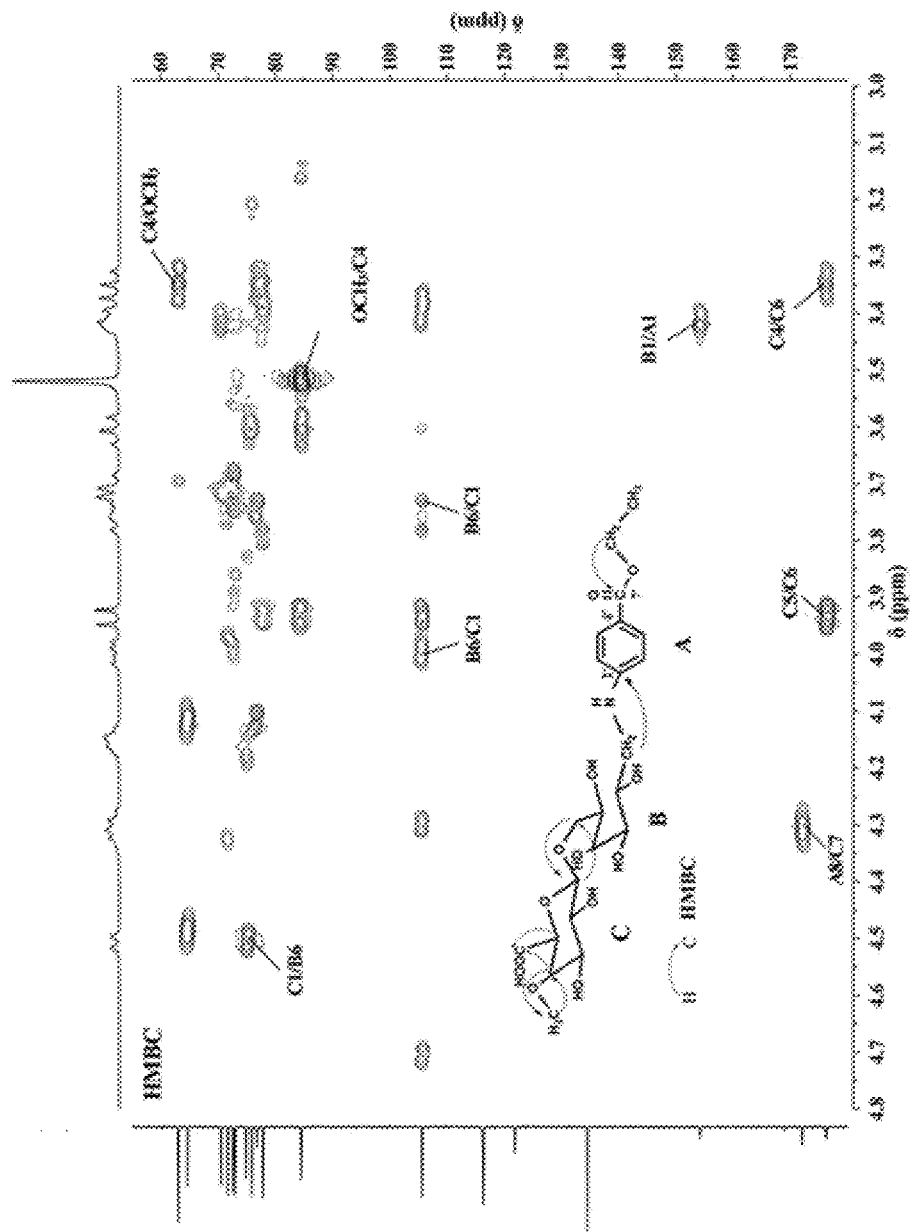
FIG. 17P shows the HMBC of Am-1.
Figure 17Q:
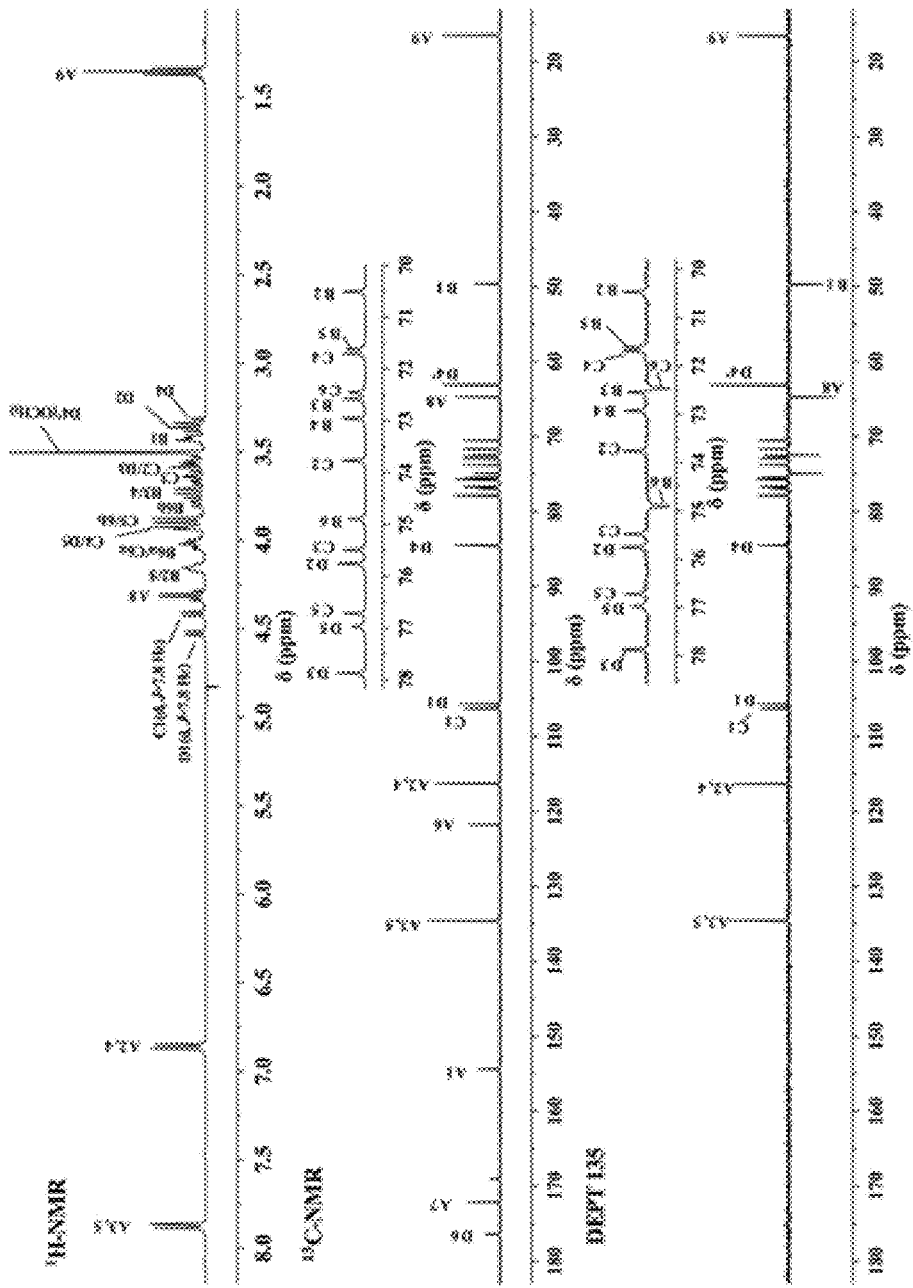
FIG. 17Q shows the $^1$H-NMR, $^{13}$C-NMR and DEPT135 of Am-2.
Figure 17R:
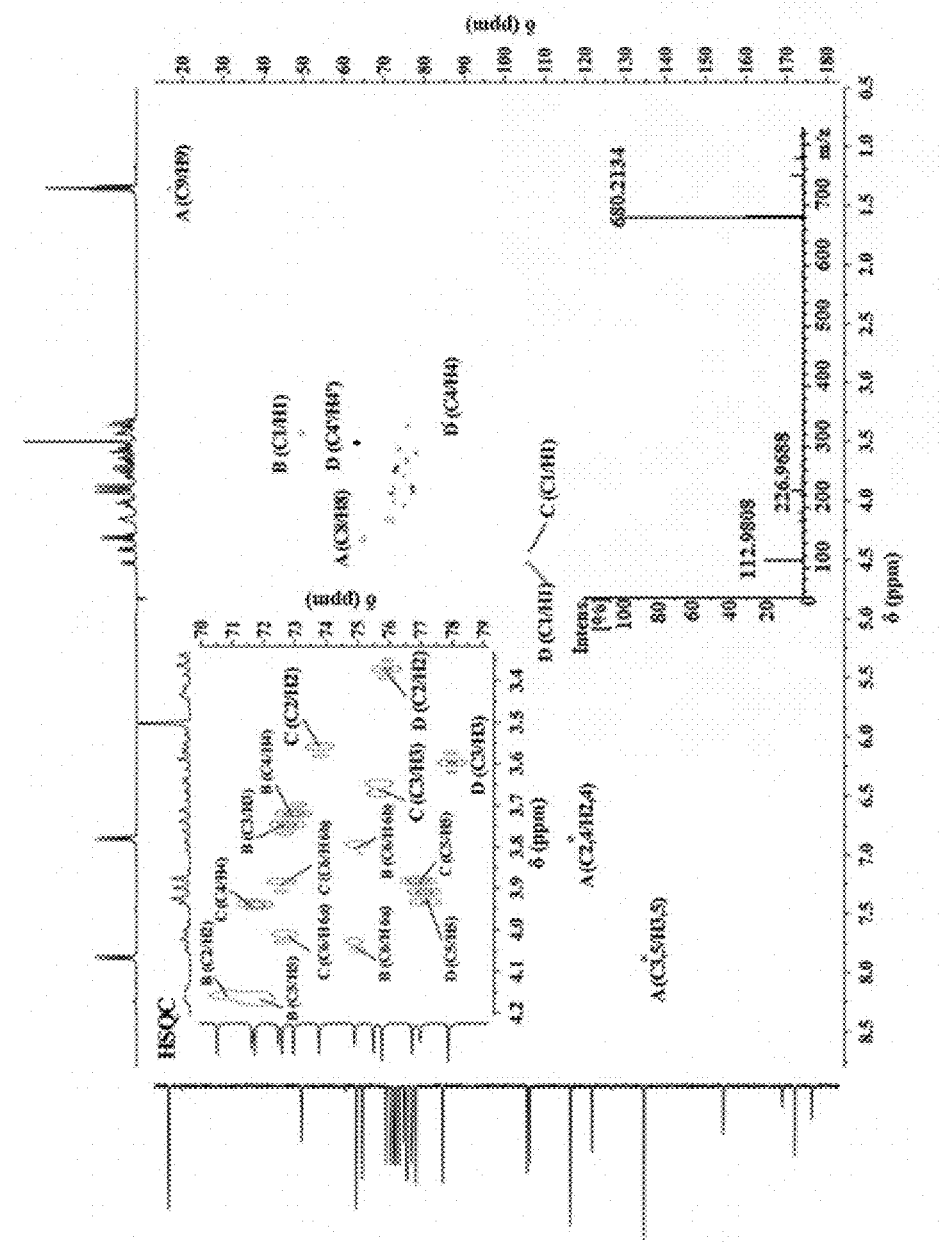
FIG. 17R shows the MS and HSQC of Am-2.
Figure 17S:
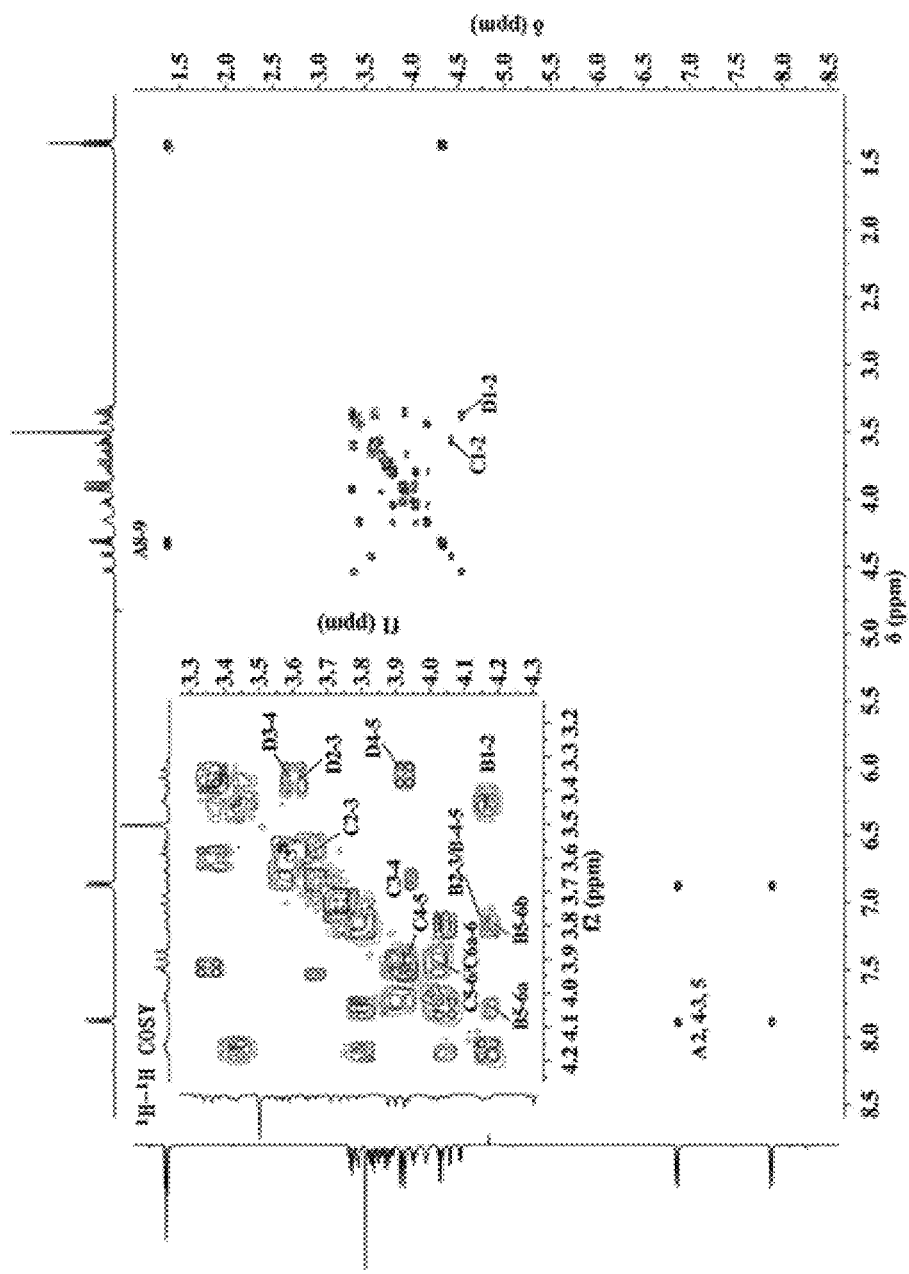
FIG. 17S shows the $^1$H-$^1$H COSY of Am-2.
Figure 17T:
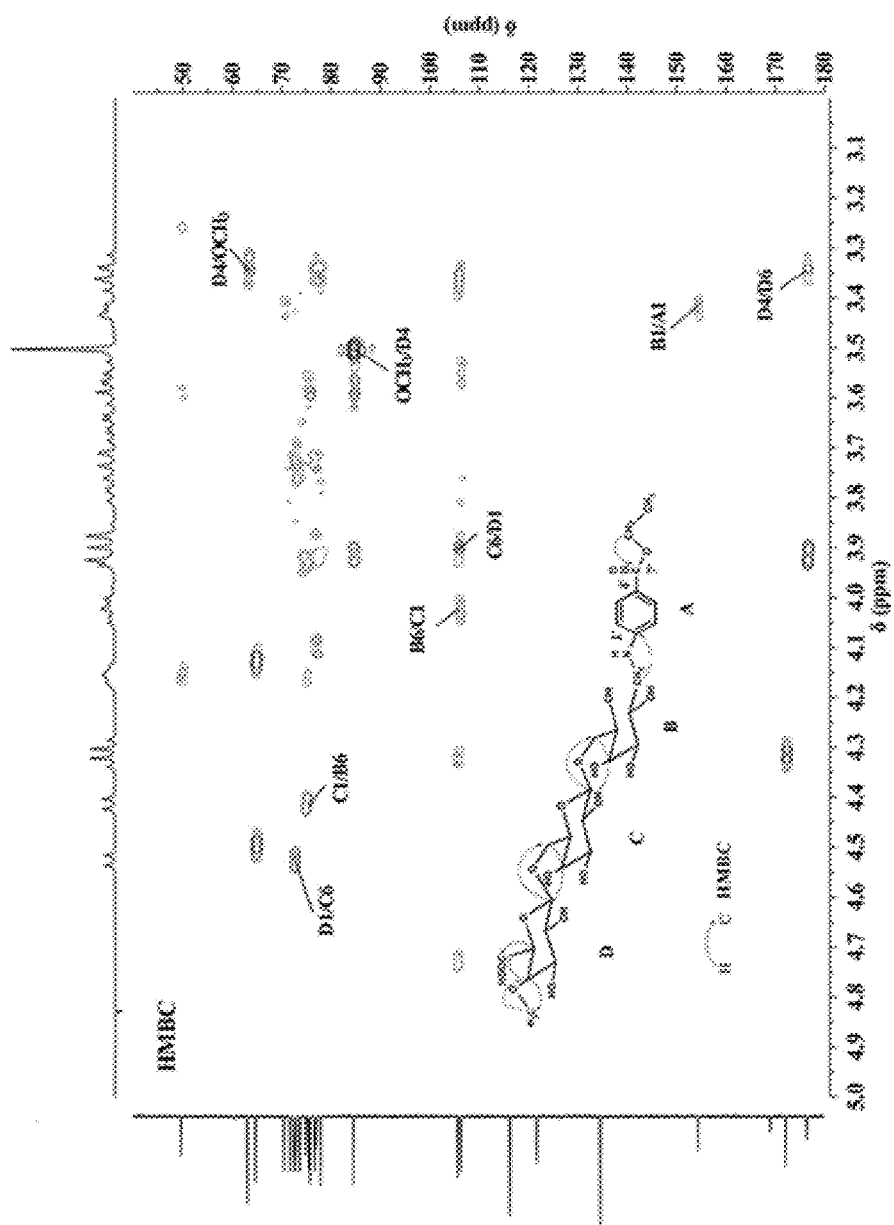
FIG. 17T shows the HMBC of Am-2.

Firstly, the FIG. 16 shows that all of three oligosaccharides are composed of glucose. Combined with the mass spectroscopy information, the Rm-1, Rm-2 and Rm-3 were supposed to be a disaccharide, trisaccharide and octasaccharide, respectively. The NMR data (FIGS. 17A-17L and Table 7 (FIG. 29)) shows that Rm-1, Rm-2 and Rm-3 share most structural characteristics. The characteristic signals of these ABEE-labeled markers could be divided into three parts: 1) ABEE part: the signals $\delta_C$ 155.8, $\delta_C$ 114.9/$\delta_H$ 6.73, $\delta_C$ 134.5/$\delta_H$ 7.82, $\delta_C$ 120.1 ppm corresponding to phenol structure of ABEE, signal at $\delta_C$ 172 ppm attributable to the carbonyl group, and signals at $\delta_C$ 64.4/$\delta_H$ 4.30 and $\delta_C$ 16.5/$\delta_H$ 1.35 assignable to the —CH2 and —CH$_3$ groups; 2) sugar linked to ABEE: anomeric signals of $\delta_C$ 48.4/$\delta_H$ 3.36, 3.41; 3) the remaining sugar residues: anomeric proton signals at $\delta_H$ 5.13 (1H, d, J=3.8 Hz) and around 5.36 ppm (6H, overlapped), which coupling constant (<4.0 Hz) suggesting α-anomeric configuration. In addition, based on peak correlation plots of $\delta_C$ 80, 85/$\delta_H$ 3.65, 3.90 in HSQC, as well as their significant HMBC correlations with the anomeric signals, the sugar linkage of (1→4)-linked-α-D-glucopyranose was proposed. For Rm-3, the linkage types have been further confirmed methylation analysis by GC-MS and the result has been showed in Table 8 (FIG. 30).

For Am-1 and Am-2 (FIGS. 17M-17T and Table 7 (FIG. 29)), they are disaccharide and trisaccharide, respectively. Besides the similar signal generated by ABEE, they show different characteristics from Rm. The information is as following: 1) The NMR spectra showed anomeric carbons signals from 105.6 to 106.3 ppm and anomeric protons signals from 4.41 ppm and 4.51 ppm with the coupling constant of 7.8 Hz (>6.0). It demonstrated that the oligosaccharides were composed of β-anomeric configurations; 2) with the influence of ABEE labeling, the general character of the anomeric carbon disappeared. Instead, the chemical shift of the unit linked with ABEE has shifted to the high-field as $\delta_C$ 49.68/$\delta_H$ 3.41; in addition, the signal of C1 of the other sugar units were generally not affected by the ABEE; 3) the strong signal at $\delta_C$ 63.11/$\delta_H$ 3.51 was attributed to the —OCH$_3$— group; 4) the signal at 176 ppm was assigned to —COOH group in galacturonic acid derivates; 5) From the DEPT 135, obvious reversal signal can be observed at 72.45 ppm and 74.89 ppm, suggesting that the C-6 has be replaced by the other sugar units; and 6) The cross signals in HMBC spectrum showed that the H-1 signals just correlated with C-6, demonstrating that the sugar units were (1→6)-linked-β-D-galactopyranose. Therefore, the chemical structure of Am-1 and Am-2 were deduced to be a complicated digalactose and trigalactose derivative as shown in FIG. 15A-15E.

Figure 18A:
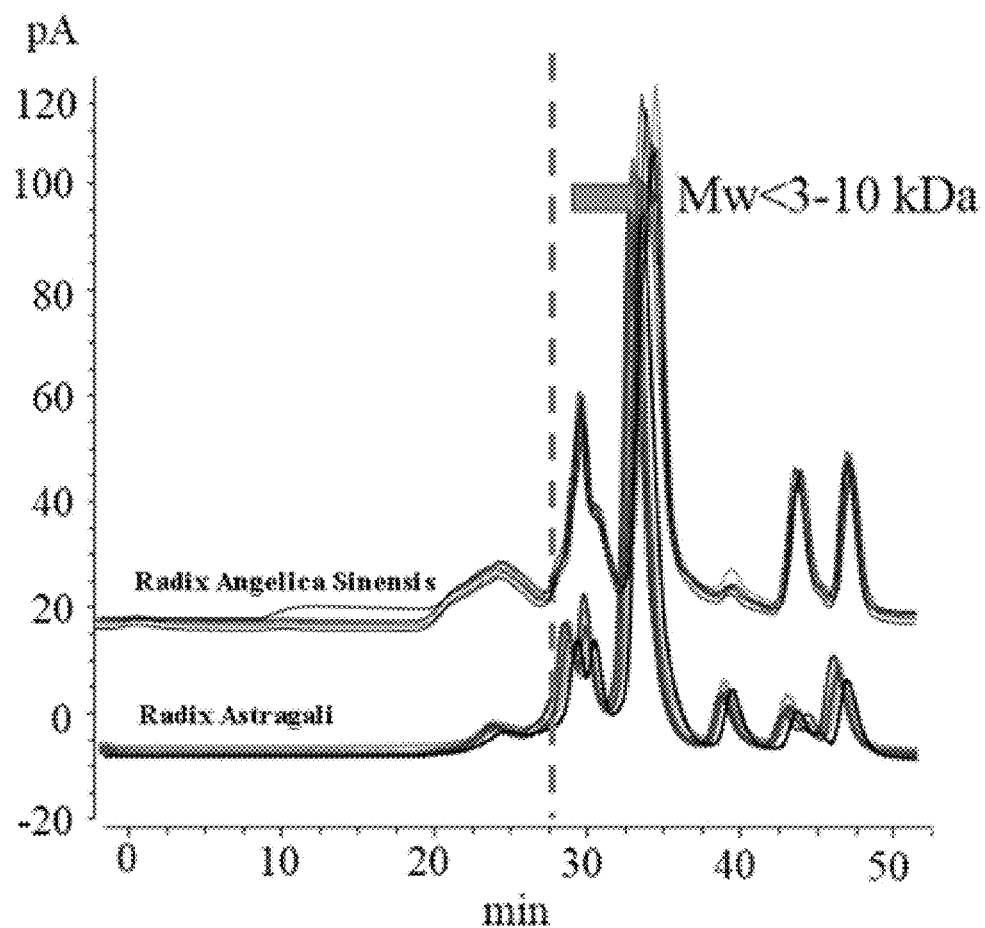
FIG. 18A shows the HPGPC chromatograms of water extracts of Radix Astragali and Radix Angelica Sinensis (n=6).
Figure 18B:
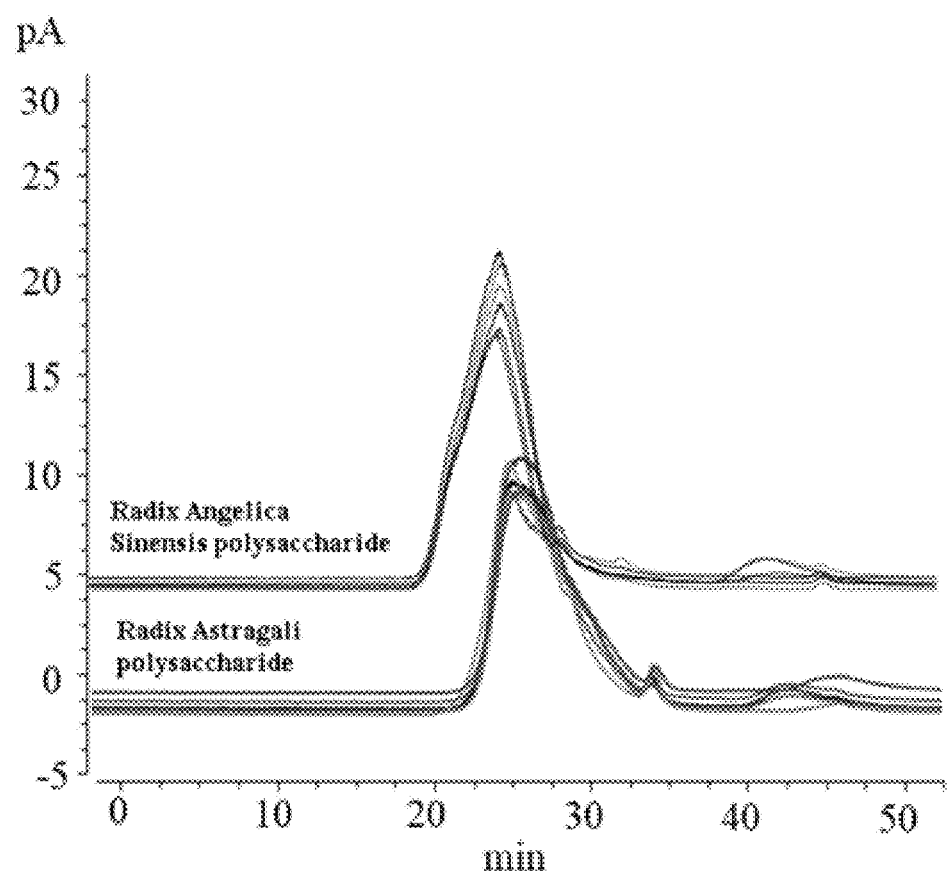
FIG. 18B shows the HPGPC chromatograms of water extracts of Radix Astragali polysaccharides and Radix Angelica Sinensis polysaccharides (n=6).

Qualitative analysis: Following the flow chart in FIG. 14, all batches of Radix Astragali and Radix Angelica Sinensis samples were qualitatively analyzed. Firstly, water extracts of Radix Astragali and Radix Angelica Sinensis (FIG. 18A) were analyzed and compared using HPGPC-CAD. The results presented extremely similar chromatographic characteristics. According to the GPC chromatograms, five peaks could be found in these samples based on their molecular distribution and the first peak with the highest molecular was found to be the majority. When the dominant peak was separated, the polysaccharides (FIG. 18B) also showed high consistency. All the results demonstrated the quality of the six batches of Radix Astragali and Radix Angelica Sinensis samples were presented consistently and the HPGPC chromatograms could be used as a preliminary identification method.

Figure 19A:
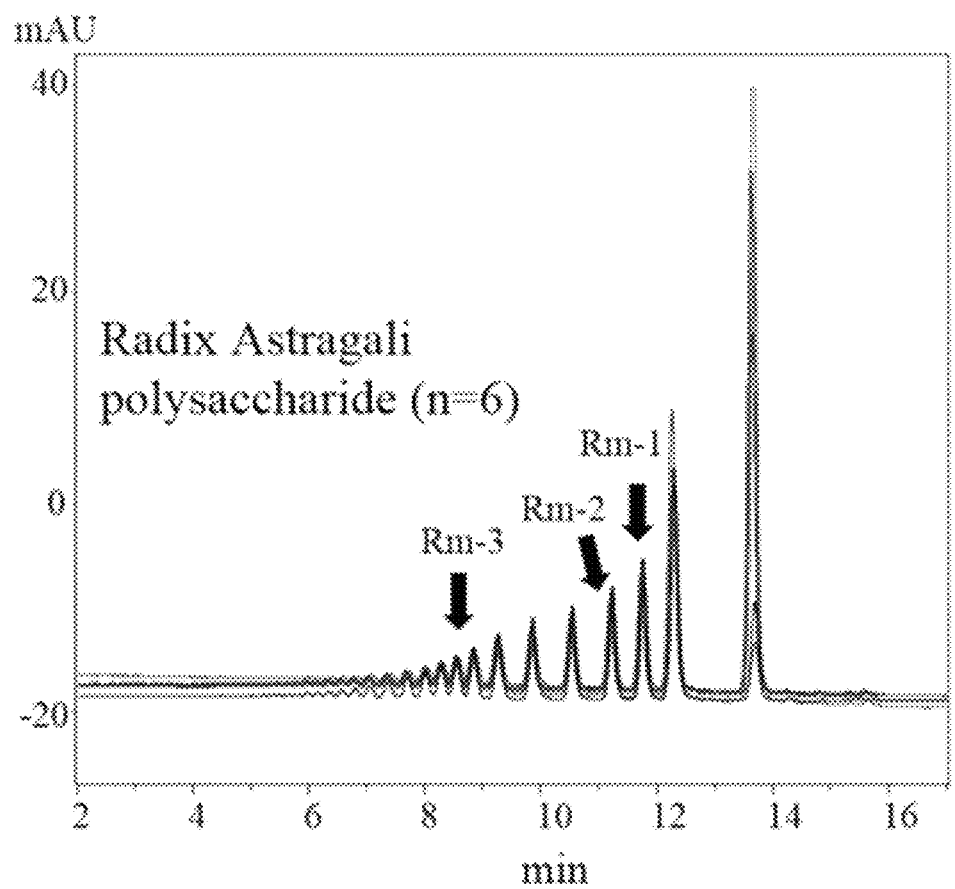
FIG. 19A shows the labeled-oligosaccharides profile of polysaccharide from *Radix Astragali* after partial acid hydrolysis. The identified oligosaccharides are labelled as Rm-1, Rm-2 and Rm-3.
Figure 19B:
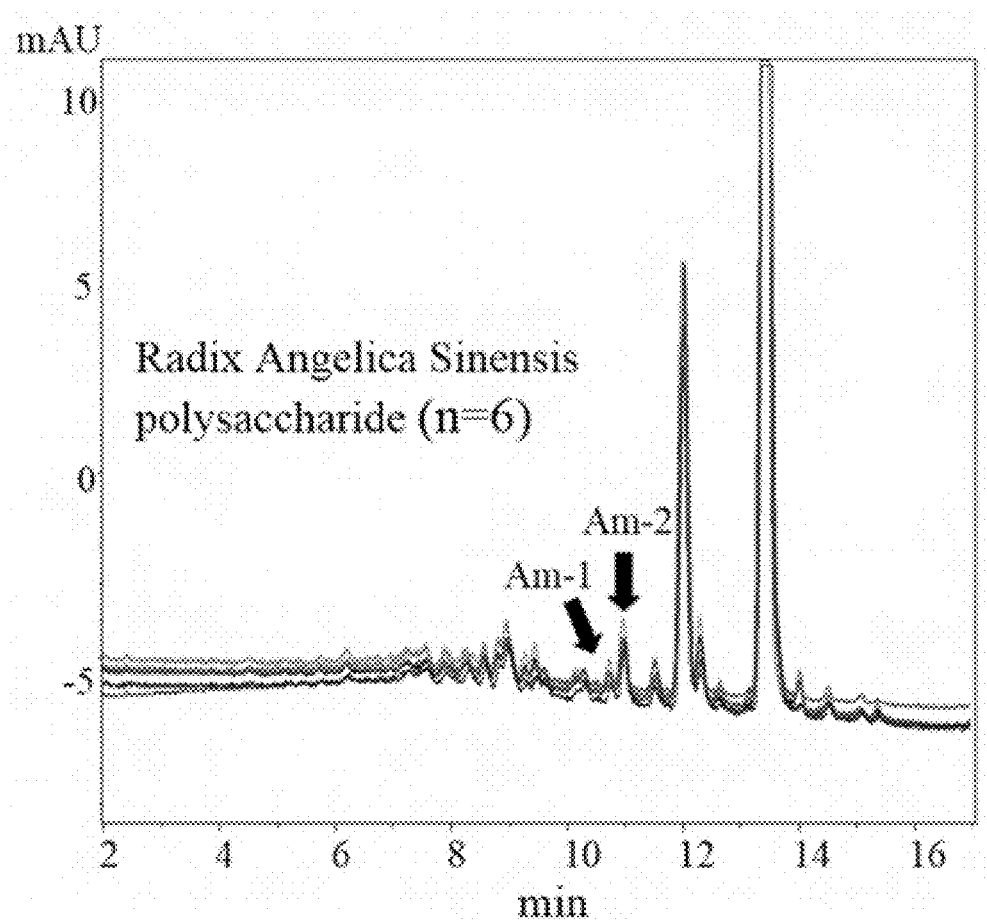
FIG. 19B shows the labeled-oligosaccharides profile of polysaccharide *Radix Angelica Sinensis* after partial acid hydrolysis. The identified oligosaccharides are labelled as Am-1 and Am-2.
Figure 20A:
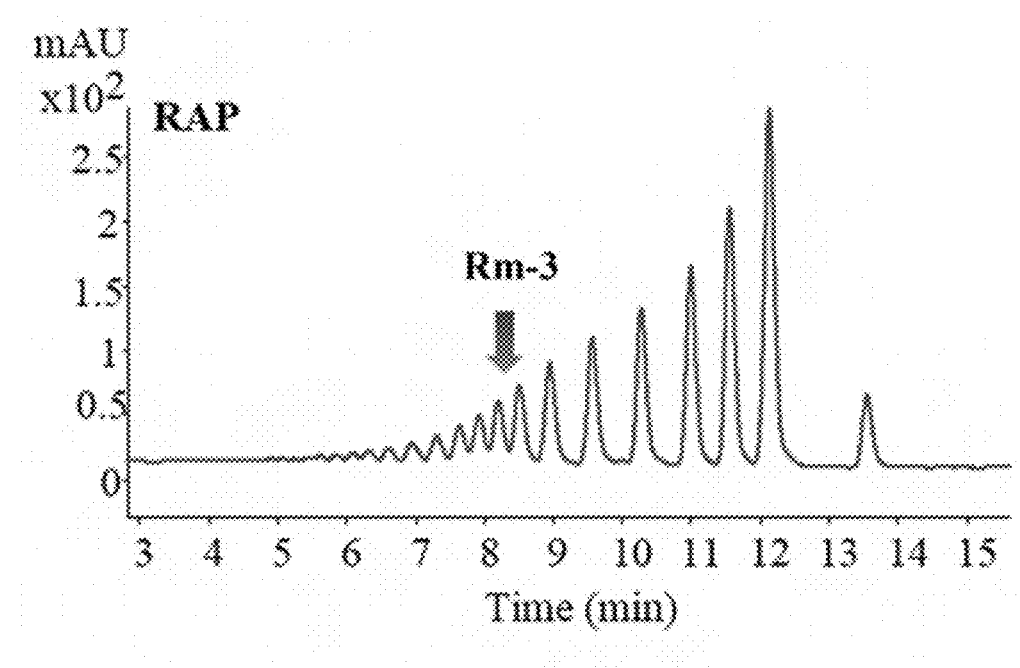
FIG. 20A shows the specificity of the selected ABEE-labeled oligosaccharide markers Rm-3. UV chromatograms ($\lambda$=305 nm) of ABEE-labeled oligosaccharide fragments: oligosaccharides produced by partial hydrolysis of RAP. The selected markers are indicated by arrows in the chromatograms.
Figure 20B:
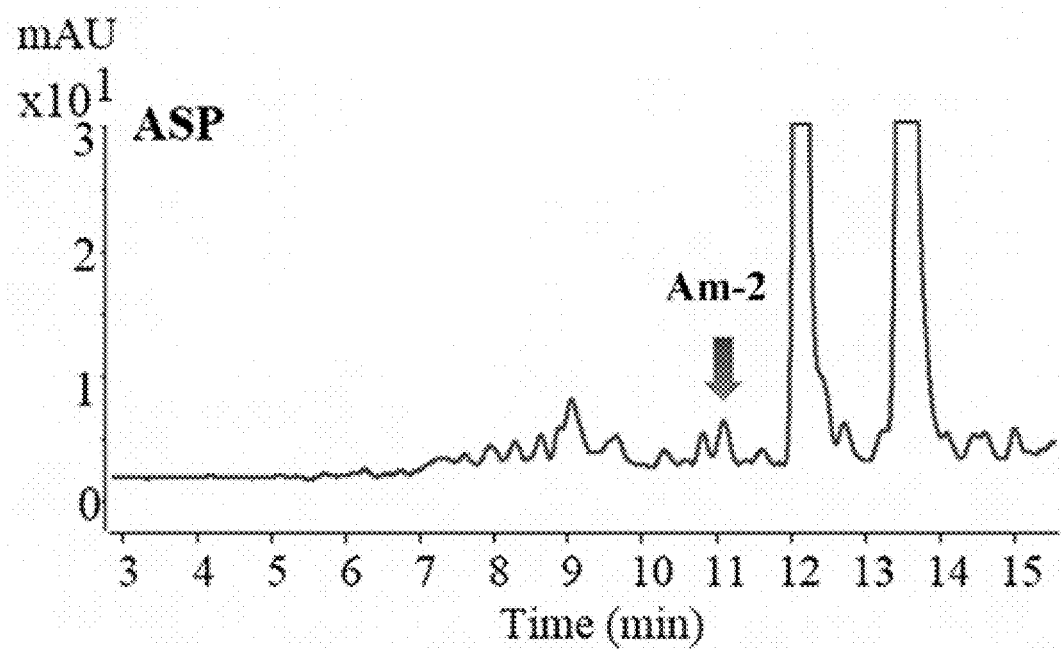
FIG. 20B shows the specificity of the selected ABEE-labeled oligosaccharide markers Am-2. UV chromatograms ($\lambda$=305 nm) of ABEE-labeled oligosaccharide fragments: oligosaccharides produced by partial hydrolysis of ASP. The selected markers are indicated by arrows in the chromatograms.
Figure 20C:
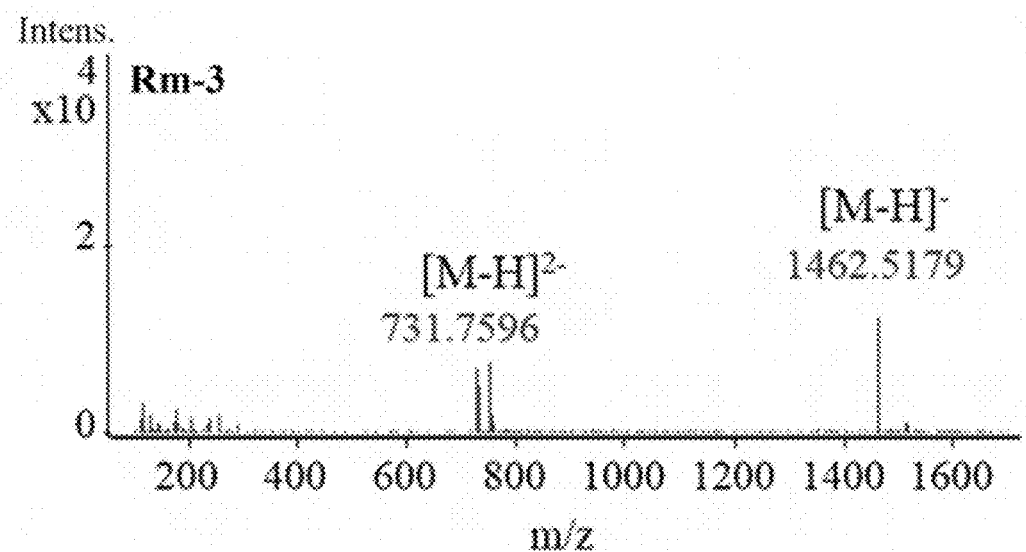
FIG. 20C shows ESI mass spectra of Rm-3 m/z 1462.5179±0.050 (retention time=8.23 min) in negative mode.
Figure 20D:
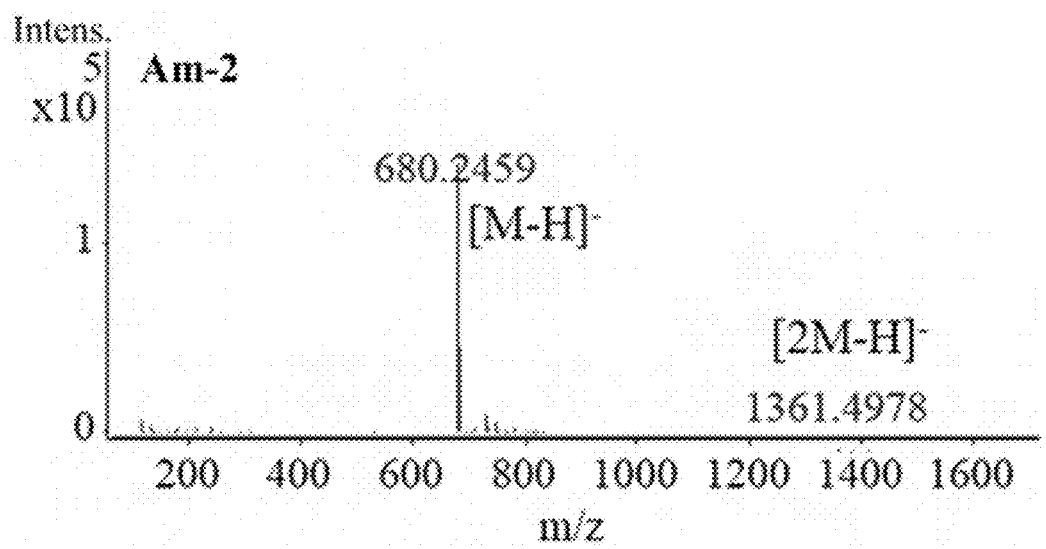
FIG. 20D shows ESI mass spectra of Am-2 m/z 680.2459±0.050 (retention time=11.03 min) in negative mode.
Figure 20E:
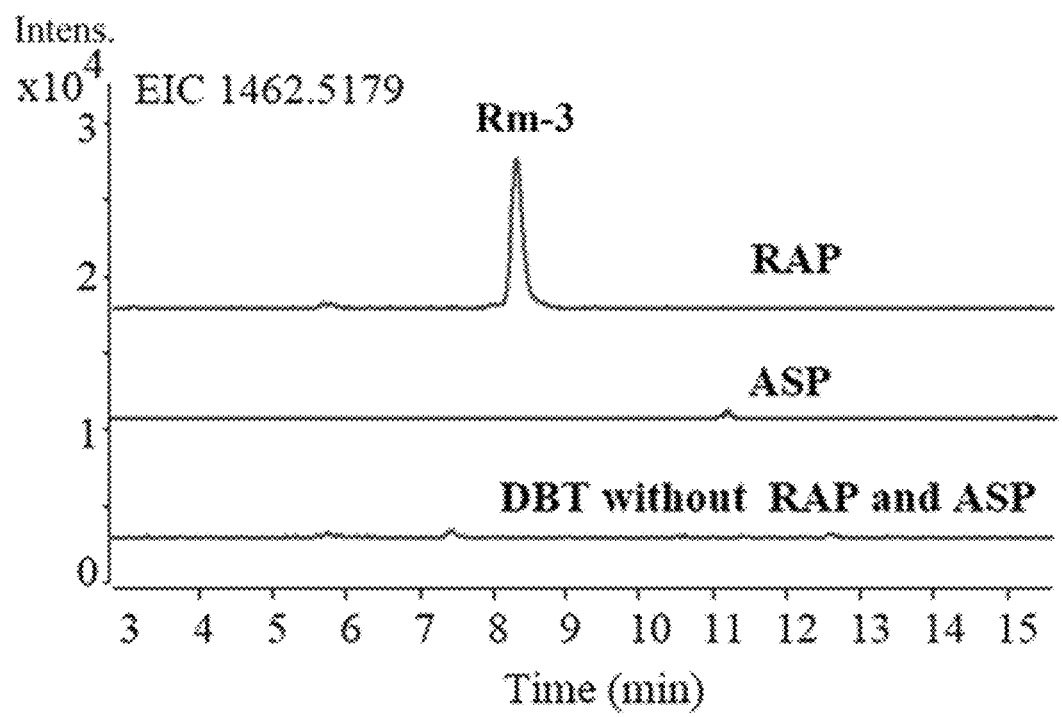
FIG. 20E shows extracted ion chromatograms (EIC) of Rm-3 in hydrolyzed RAP, ASP and DBT without RAP and ASP.
Figure 20F:
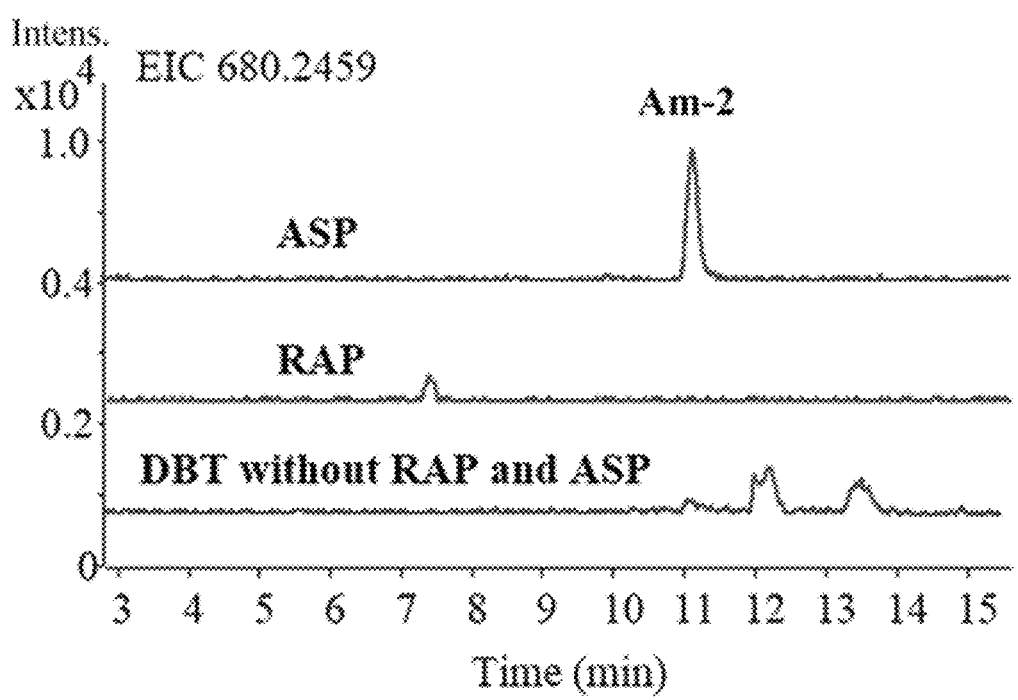
FIG. 20F shows extracted ion chromatograms (EIC) of Am2 in hydrolyzed RAP, ASP and DBT without RAP and ASP.

Further, the polysaccharides were mildly hydrolyzed to release more oligosaccharides. After the ABEE labeling, these polar compounds became easy to be separated and detected. The most important thing was that the saccharide profiles (FIGS. 19A and 19B) showed special profile with self-coded pattern and high consistency. In addition, the retention time and mass the fragmentation between the prepared representative markers and the peaks in the pattern were the same. The result indicated that the oligosaccharide markers and the pattern can be used to identify the Radix Astragali polysaccharides and Radix Angelica Sinensis after partial acid hydrolysis and ABEE (or an analog thereof) derivatization.

Finally, to successfully identify the specific polysaccharides in related herbal formula, the oligosaccharide-marker should be specific enough and highly reproducible. The high specificity means that 1) the marker should not naturally exist in the original water decoction, and 2) the marker should not be produced by polysaccharide of other herb components. As shown in Table 9 (FIG. 30), there are nine ABEE-labeled oligomers for each polysaccharide, with four common peaks. Those uncommon peaks were further checked one by one in the polysaccharide-absent herbal formula (DBT) after this extract was treated with hydrolysis and ABEE-labeling in parallel. Three and five marker candidates were for RAP and ASP, respectively. Theoretically they all could be used as the marker, but finally the identified marker Rm-3 (Rt of 8.23 min and m/z 1462.5179) and Am-2 (the Rt of 11.03 and m/z 680.2459) were selected for RAP and ASP, respectively. These two markers are in high specificity and well separated from other peaks (FIG. 20A-20F). Thus, Rm-3 and Am-2 were used for determining RAP and ASP in individual herbs and related formula.

Basic characterization of standard polysaccharide: For quantitative analysis, the prepared polysaccharide should be standardized to get stable linear relationship between polysaccharide and oligosaccharide markers. The parameters including molecular weight, total sugar content, uronic acid content, protein content and monosaccharide composition were recorded. As shown in the Table 10 (FIG. 31), these data showed that the preparation of standard polysaccharide RAP and ASP was highly repeatable with RSD ≤6.0%, and these standard polysaccharides fulfill the criteria: total sugar and uronic acid content above 90%, protein content below 5.0%.

Figure 21A:
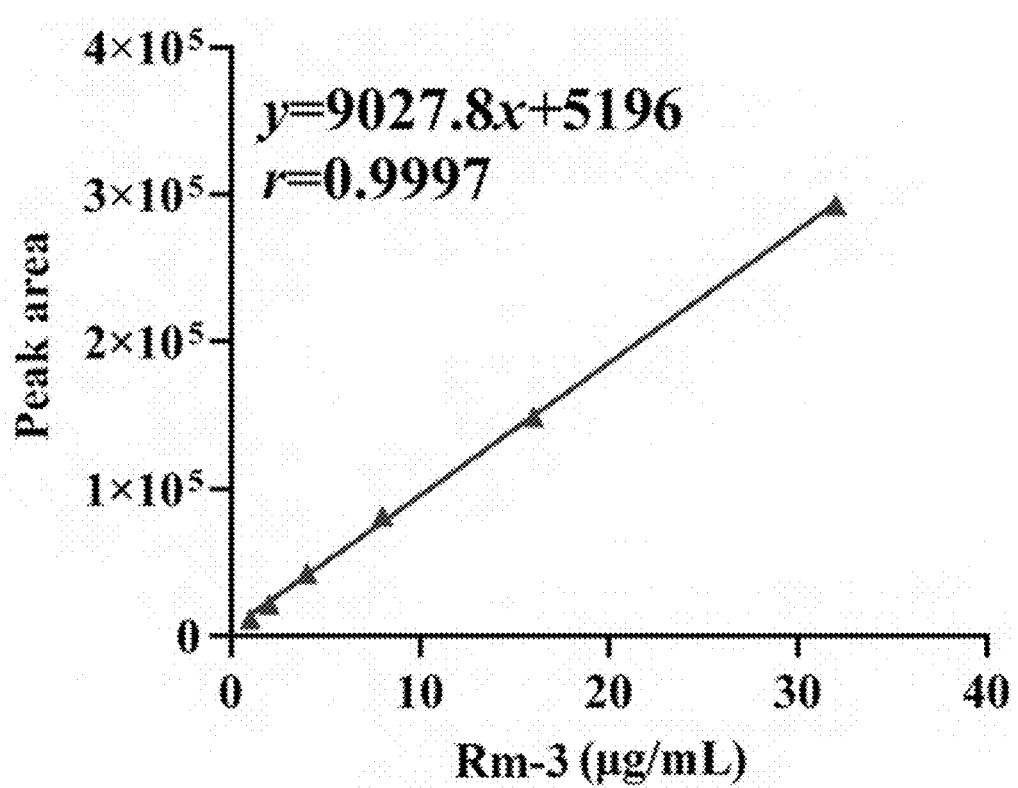
FIG. 21A shows linear relationship between standard polysaccharides and ABEE-labeled oligosaccharide markers. Calibration curves were obtained by marker concentration versus peak area, polysaccharide amount versus marker amount, and polysaccharide amount versus peak area of markers of Rm (linear range from 1.0 to 32.0 μg/mL). Data are shown as mean±SD (n=3).
Figure 21B:
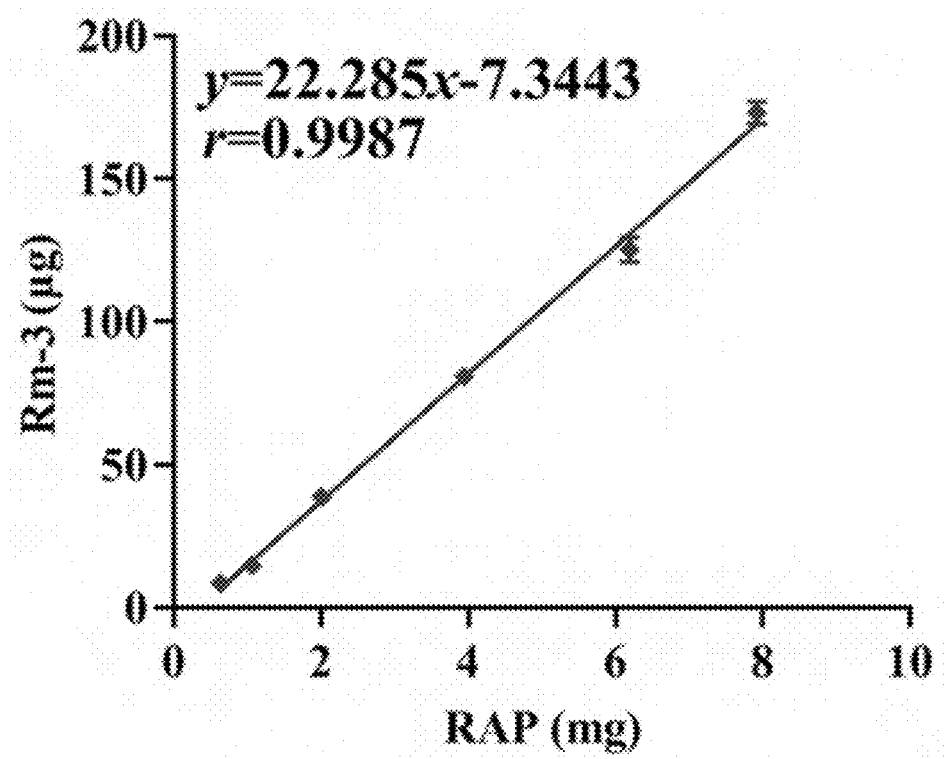
FIG. 21B shows linear relationship between standard polysaccharides and ABEE-labeled oligosaccharide markers. Calibration curves were obtained by marker concentration versus peak area, polysaccharide amount versus marker amount, and polysaccharide amount versus peak area of markers of RAP amount versus Rm-3 amount. Data are shown as mean±SD (n=3).
Figure 21C:
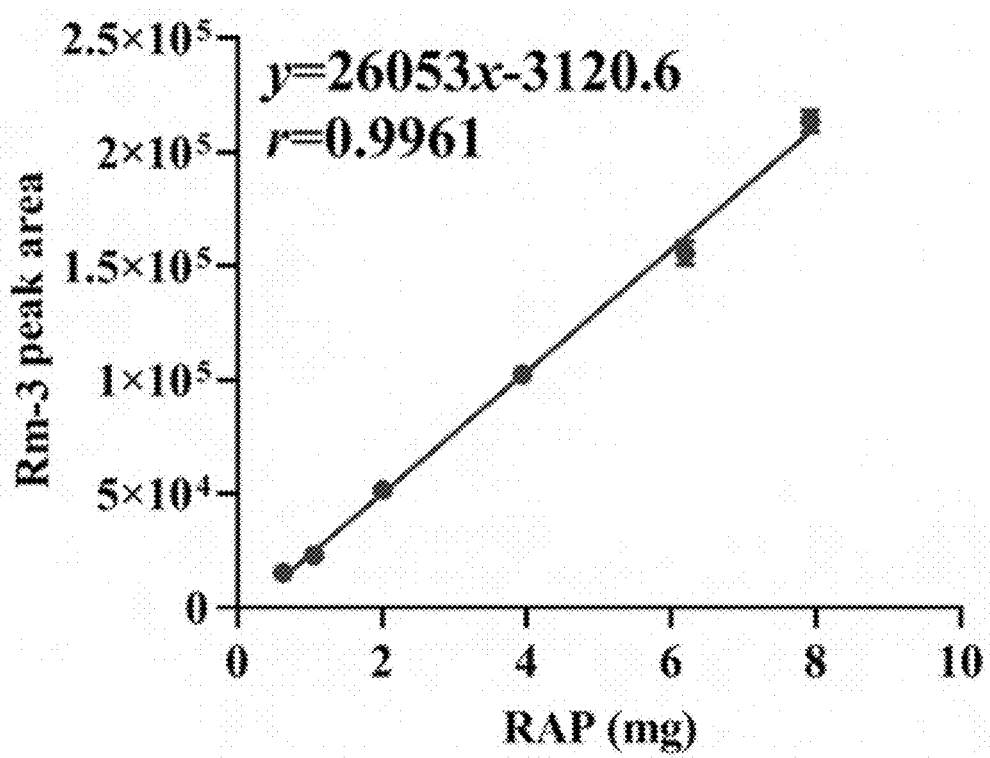
FIG. 21C shows linear relationship between standard polysaccharides and ABEE-labeled oligosaccharide markers. Calibration curves were obtained by marker concentration versus peak area, polysaccharide amount versus marker amount, and polysaccharide amount versus peak area of markers of RAP amount versus peak area of Rm-3. Data are shown as mean±SD (n=3).
Figure 21D:
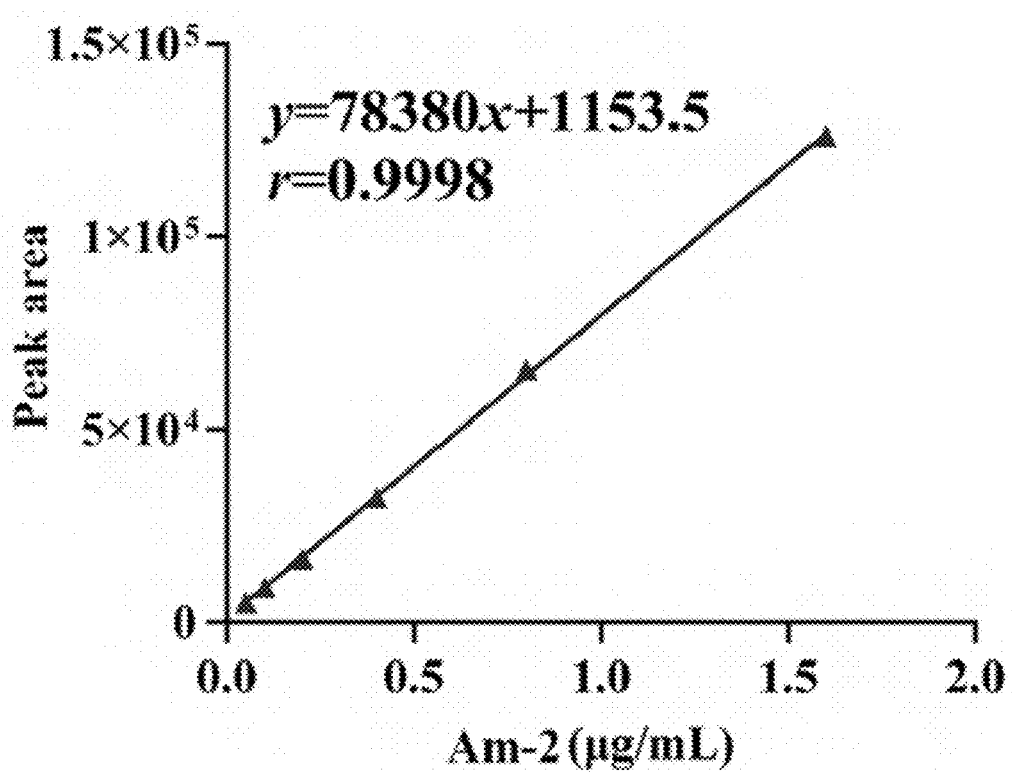
FIG. 21D shows linear relationship between standard polysaccharides and ABEE-labeled oligosaccharide markers. Calibration curves were obtained by marker concentration versus peak area, polysaccharide amount versus marker amount, and polysaccharide amount versus peak area of markers of Am-2 (linear range from 0.05 to 1.6 μg/mL). Data are shown as mean±SD (n=3).
Figure 21E:
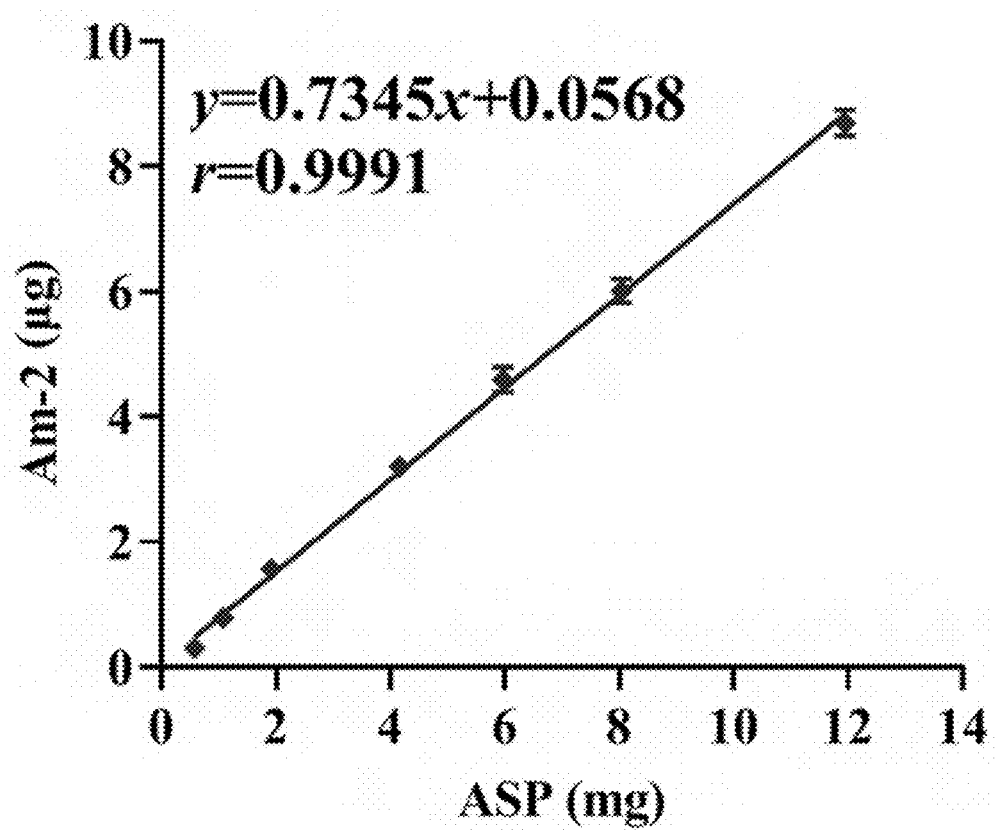
FIG. 21E shows linear relationship between standard polysaccharides and ABEE-labeled oligosaccharide markers. Calibration curves were obtained by marker concentration versus peak area, polysaccharide amount versus marker amount, and polysaccharide amount versus peak area of markers of ASP amount versus Am-2 amount. Data are shown as mean±SD (n=3).
Figure 21F:
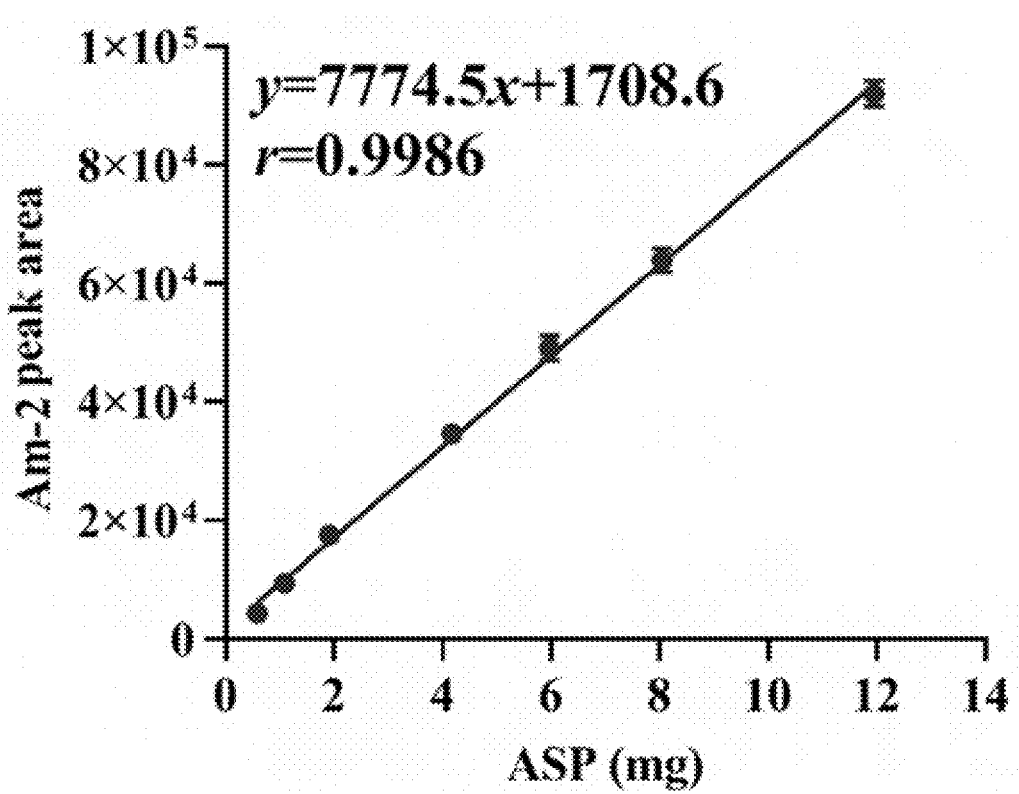
FIG. 21F shows linear relationship between standard polysaccharides and ABEE-labeled oligosaccharide markers. Calibration curves were obtained by marker concentration versus peak area, polysaccharide amount versus marker amount, and polysaccharide amount versus peak area of markers of ASP amount versus peak area of Am-2. The linear range of RAP and ASP was 0.63-7.92 mg and 0.58-11.94 mg. Data are shown as mean±SD (n=3).

Quantitative method development and validation: The inventors hypothesized that there would be a linearity between RAP and Rm-3, and between ASP and Am-2, and in turn using the established linearity, the amount of RAP and ASP in water extracts and DBT can be calculated. The results showed RAP and ASP presented satisfactory linear relationships with their respective markers (r≥0.9987) (FIG. 21A-21D). Therefore, finally in this study, the inventors directly performed linear regressions by plotting the peak areas of markers versus the amounts of RAP and ASP. The calibration curves were adequate in the range of 0.63-7.92 mg, 0.58-11.94 mg, and the coefficients of correlation (r) were beyond 0.9961 (FIG. 21E-21F).

Furthermore, the established method was systematically validated in terms of precision, stability (intra-day and inter-day), sensitivity, and accuracy (expressed as spiked recoveries).

As shown in Table 10 (FIG. 31), the overall intra- and inter-day RSD variations of Rm-3 were about 4.81% and 6.79% in Radix Astragali water extract, and 4.21% and 4.74% in DBT, respectively. The overall intra- and inter-day RSD variations (Table 11, (FIG. 32)) of Am-2 were about 5.24% and 7.39% in Radix Angelica Sinensis water extract, and 5.65% and 8.31% in DBT, respectively. As shown in Table 11 (FIG. 32), the method also showed acceptable accuracy, with RAP's spike recovery of 84.9%-96.2% in Astragalus water extract and 83.3%-87.2% in DBT (1:1), and with ASP's spike recovery of 79.8%-85.9% in Angelica water extract and 81.2%-86.3% in DBT (1:1) at different concentrations, respectively.

In summary, these results displayed that the established method had satisfactory specificity, linearity, precision, and accuracy.

Figure 22A:
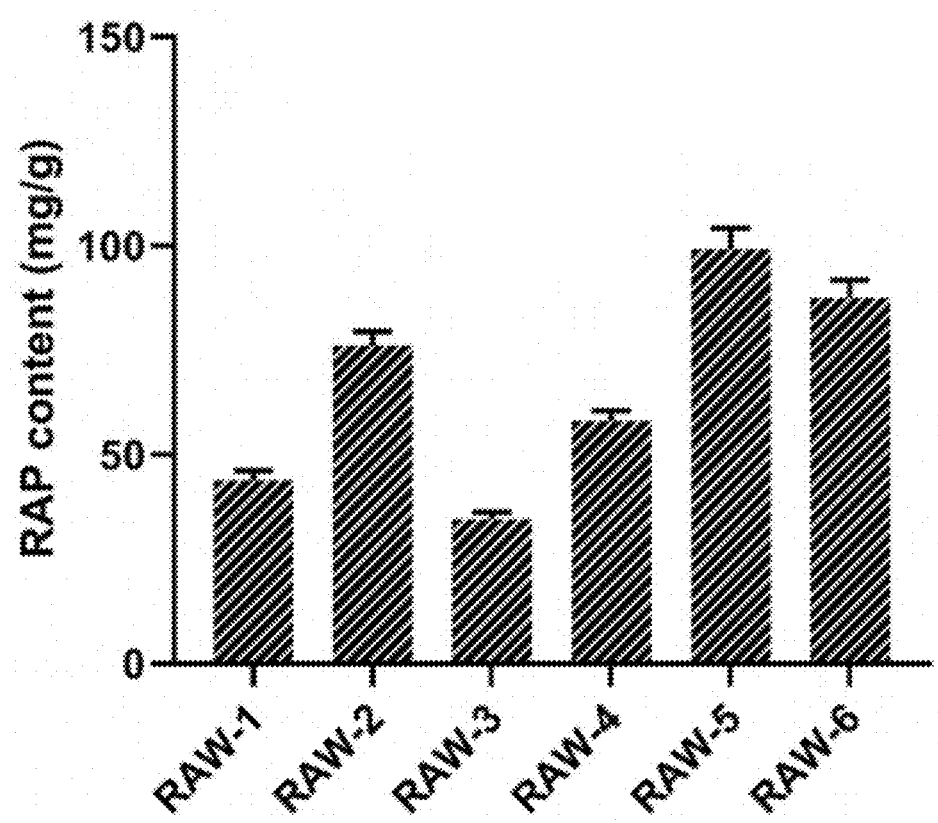
FIG. 22A shows the quantitation of the RAP by the established method with six batches of Radix Astragali water extract (RAW-1~RAW-6)
Figure 22B:
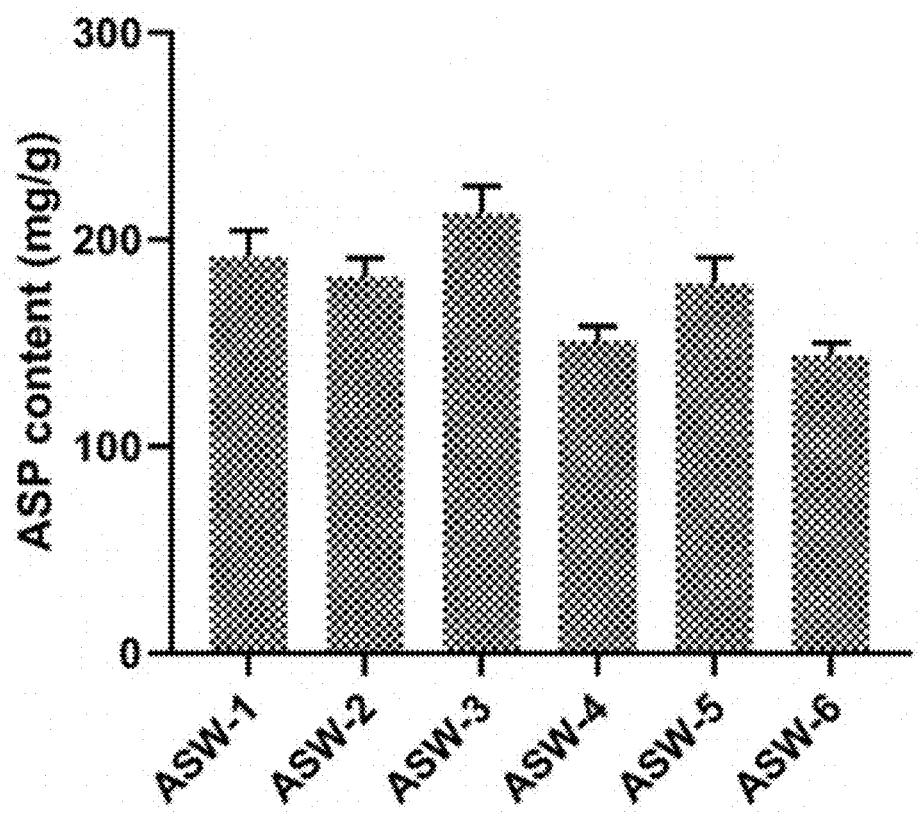
FIG. 22B show the quantitation of the ASP by the established method with six batches of Radix Angelica Sinensis (ASW-1~ASW-6)
Figure 22C:
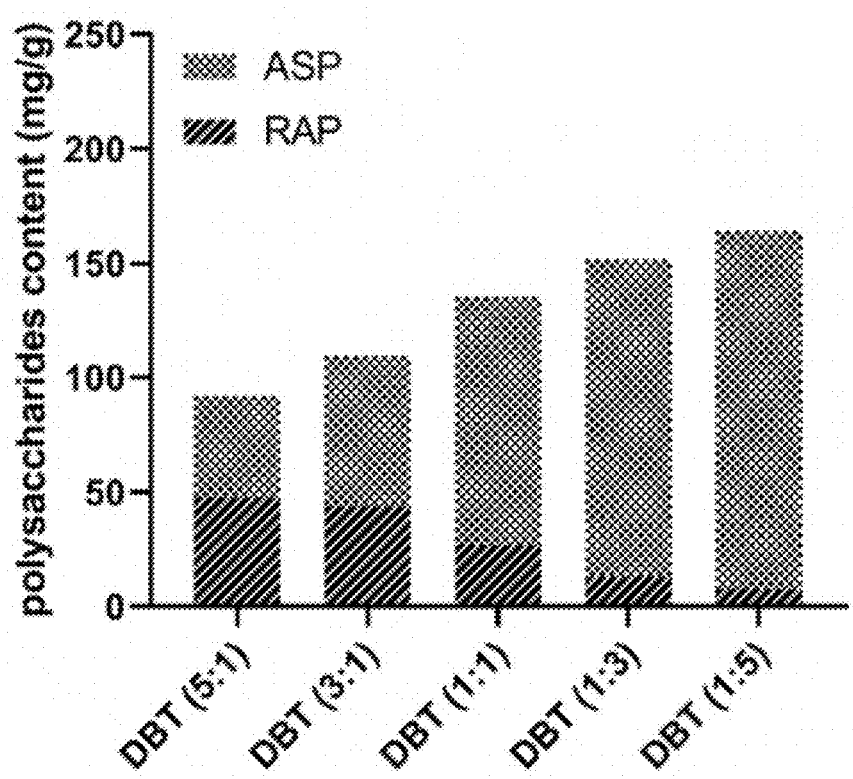
FIG. 22C shows RAP and ASP content in DBT. DBT was prepared by *Radix Astragali* and Radix Angelica Sinensis in a weight ratio of 5:1, 3:1, 1:1, 1:3, 1:5. Data are shown as mean±SD (n=3).

Application in real samples: The validated method was applied to quantitative analysis of RAP and ASP in six batches of individual herbs and DBTs. The quantitative analysis data are showed in FIG. 22A-22C. The amount of RAP accounted for different percentage in Radix Astragali water extract from 34.7 to 99.2 mg/g. While the amount of ASP accounted for similar percentage in Radix Angelica sinensis water extract from 151.02 to 212.75 mg/g.

In the herbal formula-DBT, with reduced ratio of Radix Astragali and increased ratio of Radix Angelica Sinensis, the RAP content contained decreased from 7.79 to 47.71 mg/g and the ASP content contained in DBT also raised from 92.20 to 164.41 mg/g.

Conclusion

By taking *Dendrobium officinale* as a model herb, a novel and accurate UHPLC-qTOF-MS-DAD based method was developed for quality control of the content of polysaccharide of herbal materials in commercial products and Chinese medicine decoction by simultaneously qualitative and quantitative characterization of the oligosaccharide markers which are derived from the polysaccharides itself and are firstly proposed and demonstrated. The constant relationship between the content of oligosaccharide markers and the content of polysaccharides is also firstly employed for quantitative purpose. The experimental results indicated that the newly-established method was more efficient, stable and ground-breaking method that provides qualitative and quantitative evaluation of *Dendrobium officinale* in commercial products and Chinese medicine decoction. Even the evaluation of Chinese medicine decoction, which composes with more than one herbal material, cannot be achieved before, with this invention, it is possible to evaluate the content of carbohydrate-dominant herbal materials mixtures. Though *Dendrobium officinale* has been used as a model herb, it is understandable that the present invention should also be practicable for the quality control of other saccharide-dominant herbal materials and products.

Also provided herein are ABEE (or an analog thereof) labeled oligosaccharide markers. These oligosaccharides were from the polysaccharide in Radix Astragali and Radix Angelica Sinensis after partial acid hydrolysis and ABEE (or an analog thereof) derivatization. The current disclosure further provides qualitative and quantitative methods for specific polysaccharides in individual herbs and related formulas.

In summary, the present disclosure relates to the quality control oligosaccharide markers and method of using these markers in qualitative and quantitative authentication of polysaccharides in herbal material. These markers are highly specific and sensitive as there are derived from the polysaccharide itself. In the present invention, the oligosaccharide markers were isolated based on *Dendrobium officinale* and they were proved to be the specific markers that can be utilized distinguish the presence of DOP in the commercial products and Chinese medicine decoction. The compositions and methods described herein can be widely applied for authentication of *Dendrobium officinale* by testing laboratories, pharmaceutical industries and research institutions.

INDUSTRIAL APPLICABILITY

The present disclosure relates to a series of chemically produced quality control markers derived from the partial acid hydrolysis of polysaccharides present in herbs, such as DOP, ROP, or ASP and the method of using these markers in qualitative and quantitative authentication of *Dendrobium officinale*, Radix Astragali and Radix Angelica Sinensis, and related herbal products.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

What is claimed is:

1. A method for analyzing polysaccharide content in a test sample comprising at least one herb selected from the group consisting of *Dendrobium officinale*, Radix Astragali, and Radix Angelica Sinensis, the method comprising:
   contacting the test sample with a solvent comprising water thereby forming a polysaccharide sample;
   contacting the polysaccharide sample with a trifluoroacetic acid and water thereby forming a saccharide sample comprising oligosaccharides and monosaccharides;
   contacting the saccharide sample with 4-aminobenzoic acid ethyl ester (ABEE) and a reducing agent selected from the group consisting of $NaBH_4$ and $NaBH_3CN$ thereby forming an ABEE labeled saccharide sample comprising one or more ABEE labeled saccharides selected from the group consisting of:

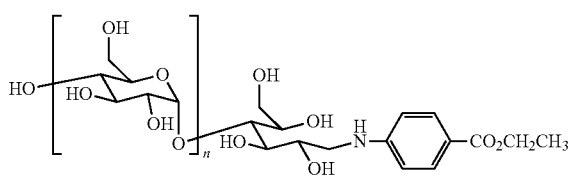

wherein n is 7;

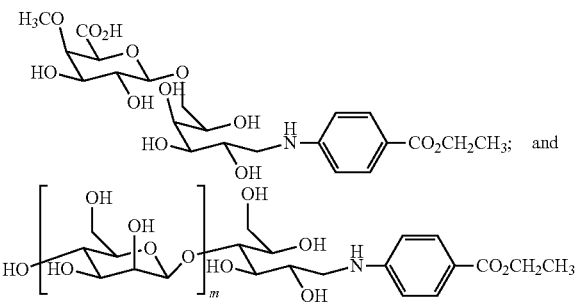

wherein m is a whole number selected from 3 or 4; and analyzing the ABEE labeled saccharide sample using at least one analytical method selected from the group consisting of liquid chromatography-mass spectrometry (LC-MS) and high-performance gel permeation chromatography (HPGPC) thereby providing test sample polysaccharide content related data.

2. The method of claim 1, wherein at least 10% of the polysaccharides in the test sample are partially hydrolyzed.

3. The method of claim 1, wherein the at least one herb is *Dendrobium officinale* and the one or more ABEE labeled saccharides is:

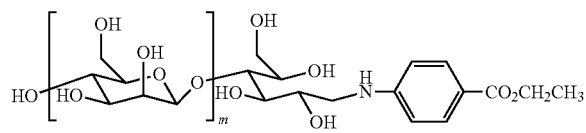

wherein m is a whole number selected from 3 or 4; or the at least one herb is selected from the group consisting of Radix Astragali, Radix Angelica Sinensis, and combinations thereof; and the one or more ABEE labeled saccharides is selected from the group consisting of:

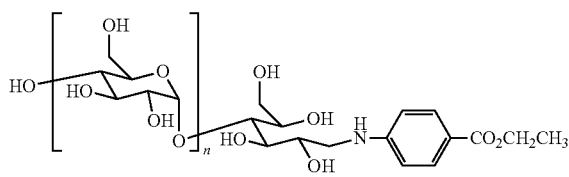

wherein n is 7; and

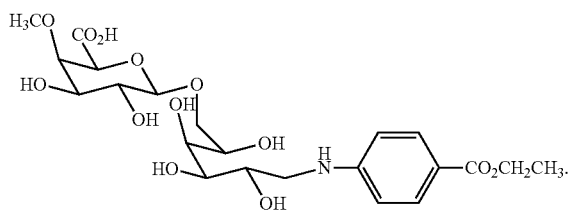

4. The method of claim 1 further comprising the step of comparing the test sample polysaccharide content related data with one or more calibration curves prepared by using the interrelation between known concentrations of the one or more ABEE labeled saccharides in standard samples; and determining the concentration of at least one polysaccharide in the test sample.

5. The method of claim 1, wherein the polysaccharide content related data is used to authenticate the quality or the identity of the at least one herb.

* * * * *